(12) United States Patent
Burford et al.

(10) Patent No.: US 7,396,663 B2
(45) Date of Patent: Jul. 8, 2008

(54) ISOLATED POLYNUCLEOTIDE ENCODING A G-PROTEIN COUPLED RECEPTOR

(75) Inventors: Neil Burford, Durham, CT (US); Mariah R. Baughn, San Leandro, CA (US); Janice K. Au-Young, Brisbane, CA (US); Junming Yang, San Jose, CA (US); Dyung Aina M. Lu, San Jose, CA (US); Roopa M. Reddy, Sunnyvale, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 11/429,430

(22) Filed: May 8, 2006

(65) Prior Publication Data

US 2006/0257911 A1 Nov. 16, 2006

Related U.S. Application Data

(62) Division of application No. 10/149,826, filed as application No. PCT/US2000/33382 on Dec. 7, 2000, now abandoned.

(60) Provisional application No. 60/172,852, filed on Dec. 10, 1999, provisional application No. 60/171,732, filed on Dec. 22, 1999, provisional application No. 60/176,148, filed on Jan. 14, 2000, provisional application No. 60/177,331, filed on Jan. 21, 2000.

(51) Int. Cl.
*C12N 15/12* (2006.01)

(52) U.S. Cl. .............. 435/69.1; 435/252.3; 435/320.1; 536/23.5

(58) Field of Classification Search ................. None
See application file for complete search history.

(56) References Cited

U.S. PATENT DOCUMENTS 6,465,212 B1 * 10/2002 Wang et al. ................ 435/69.1
6,939,953 B2 * 9/2005 Wang et al. ................. 530/350

FOREIGN PATENT DOCUMENTS

WO   WO 92/17585 A   10/1992

OTHER PUBLICATIONS

Bowie et al., 1990, Science 247:1306-1310.*
Guo-HH et al. PNAS 101(25)9205-9210, 2004.*
Alexander et al., Proc. Natl. Acad. Sci. 89(3352-3356)1992.*
Buck, et al., "A Novel Multigene Family May Encode Odorant Receptors: A Molecular Basis For Odor Recognition", Cell, US, Cell Press, XP002029935, vol. 65, pp. 175-187 (1991).
McDonald, et al., "Identification and cloning of an orphan G protein-coupled receptor of the glycoprotein hormone receptor subfamily", Biochemical and Biophysical Research, XP000999191, vol. 247, No. 2, pp. 266-270 (1998).
Gong, et al., "Rapid identification and isolation of zebrafish cDNA clones", Gene: An International Journal on Genes and Genomes, GB, Elsevier Science Publishers, Barking, XP004126460, vol. 201, No. 1-2, pp. 87-98 (1997).
Stadel, et al., "Orphan G protein-coupled receptors: a neglected opportunity for pioneer drug discovery", Trends in Pharmacological Sciences, GB, Elsevier Trends Journal, Cambridge, XP004099345, vol. 18, No. 11, pp. 430-437 (1997).
O'Dowd, et al., "Discovery of three Novel G-Protein-Coupled Receptor Genes", Genomics, Academic Press, XP000863786, vol. 47, No. 2, pp. 310-313 (1998).
Marchese, et al., "Novel GPCRs and their endogenous ligands: expanding the boundaries of physiology and pharmacology", Trends in Pharmacological Sciences, GB, Elsevier Trends Journal, XP004178194, vol. 20, No. 9, pp. 370-375 (1999).
Lee, et al., "Cloning and characterization of additional members of the G protein-coupled receptor family", Biochimica Et Biophysica Acta., XP000999198, vol. 1490, No. 3, pp. 311-323 (2000).
Rouquier, et al., "The olfactory receptor gene repertoire in primates and mouse: Evidence for reduction of the functional fraction in primates", Proceedings of the National Academy of Sciences of the United States, XP002168634, vol. 97, No. 6, pp. 2870-2874 (2000).
Genbank accession No. AC006313, Birren, B., et al., Homo Sapiens Chromosome 9 clone hRPK.465_F_21, Jan. 26, 1999.
Bowie et al., 1990, Science 247:1306-1310, especially p. 1306.
Guo-HH et al., PNAS 101(25)9205-9210, 2004.
Alexander et al., Proc. Natl. Acad. Sci. 89 (3352-3356) 1992.

* cited by examiner

*Primary Examiner*—John Ulm
(74) *Attorney, Agent, or Firm*—Foley & Lardner LLP

(57) ABSTRACT

The invention provides human G-protein coupled receptors (GCREC) and polynucleotides which identify and encode GCREC. The invention also provides expression vectors, host, cells, antibodies, agonists, and antagonists. The invention also provides methods for diagnosing, treating, or preventing disorders associated with aberrant expression of GCREC.

4 Claims, 9 Drawing Sheets

SEQ ID NO:1
(Incyte ID No. 104941CD1)

SEQ ID NO:3
(Incyte ID No. 3168839CD1)

SEQ ID NO:4
(Incyte ID No. 3291235CD1)

SEQ ID NO:5
(Incyte ID No. 7472001CD1)

SEQ ID NO:6
(Incyte ID No. 7472003CD1)

SEQ ID NO:7
(Incyte ID No. 7472004CD1)

SEQ ID NO:19
(Incyte ID No. 3068234CD1)

SEQ ID NO:20
(Incyte ID No. 5029478CD1)

SEQ ID NO:21
(Incyte ID No. 5102576CD1)

ISOLATED POLYNUCLEOTIDE ENCODING A G-PROTEIN COUPLED RECEPTOR

CROSS REFERENCE TO RELATED APPLICATIONS

This application is a Divisional of U.S. patent application Ser. No. 10/149,826, filed Jun. 10, 2002, now abandoned, which is the National Phase of International Patent Application No. PCT/US2000/33382, filed Dec. 7, 2000, and published as WO 01/42288, which claims priority to Provisional Patent Application Nos. 60/172,852, filed Dec. 10, 1999, 60/171,732, filed Dec. 22, 1999, 60/176,148, filed Jan. 14, 2000, and 60/177,331, filed Jan. 21, 2000, the contents of all of which are incorporated herein by reference.

TECHNICAL FIELD

This invention relates to nucleic acid and amino add sequences of G-protein coupled receptors and to the use of these sequences in the diagnosis, treatment, and prevention of cell proliferative, neurological, cardiovascular, gastrointestinal, autoimmune/inflammatory, and metabolic disorders, and viral infections, and in the assessment of the effects of exogenous compounds on the expression of nucleic add and amino acid sequences of G-protein coupled receptors.

BACKGROUND OF THE INVENTION

Signal transduction is the general process by which cells respond to extracellular signals. Signal transduction across the plasma membrane begins with the binding of a signal molecule, e.g., a hormone, neurotransmitter, or growth factor, to a cell membrane receptor. The receptor, thus activated, triggers an intracellular biochemical cascade that ends with the activation of an intracellular target molecule, such as a transcription factor. This process of signal transduction regulates all types of cell functions including cell proliferation, differentiation, and gene transcription. The G-protein coupled receptors (GPCRs), encoded by one of the largest families of genes yet identified, play a central role in the transduction of extracellular signals across the plasma membrane. GPCRs have a proven history of being successful therapeutic targets.

GPCRs are integral membrane proteins characterized by the presence of seven hydrophobic transmembrane domains which together form a bundle of antiparallel alpha ($\alpha$) helices. GPCRs range in size from under 400 to over 1000 amino acids (Strosberg, A. D. (1991) Eur. J. Biochem. 196:1-10; Coughlin, S. R. (1994) Curr. Opin. Cell Biol. 6:191-197). The amino-terminus of a GPCR is extracellular, is of variable length, and is often glycosylated. The carboxy-terminus is cytoplasmic and generally phosphorylated. Extracellular loops alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account, in part, for structural and functional features of the receptor. In most cases, the bundle of a helices forms a ligand-binding pocket. The extracellular N-terminal segment, or one or more of the three extracellular loops, may also participate in ligand binding. Ligand binding activates the receptor by inducing a conformational change in intracellular portions of the receptor. In turn, the large, third intracellular loop of the activated receptor interacts with a heterotrimeric guanine nucleotide binding (G) protein complex which mediates further intracellular signaling activities, including the activation of second messengers such as cyclic AMP (cAMP), phospholipase C, and inositol triphosphate, and the interaction of the activated GPCR with ion channel proteins. (See, e.g., Watson, S. and S. Arkinstall (1994) *The G-protein Linked Receptor Facts Book*, Academic Press, San Diego Calif., pp. 2-6; Bolander, F. F. (1994) *Molecular Endocrinology*, Academic Press, San Diego Calif., pp. 162-176; Baldwin, J. M. (1994) Curr. Opin. Cell Biol. 6:180-190.)

GPCRs include receptors for sensory signal mediators (e.g., light and olfactory stimulatory molecules); adenosine, γ-aminobutyric acid (GABA), hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine and norepinephrine, histamine, glutamate (metabotropic effect), acetylcholine (muscarinic effect), and serotonin); chemokines; lipid mediators of inflammation (e.g., prostaglandins and prostanoids, platelet activating factor, and leukotrienes); and peptide hormones (e.g., bombesin, bradykinin, calcitonin, C5a anaphylatoxin, endothelin, follicle-stimulating hormone (FSH), gonadotropic-releasing hormone (GnRH), neurokinin, and thyrotropin-releasing hormone (TRH), and oxytocin). GPCRs which act as receptors for stimuli that have yet to be identified are known as orphan receptors.

The diversity of the GPCR family is further increased by alternative splicing. Many GPCR genes contain introns, and there are currently over 30 such receptors for which splice variants have been identified. The largest number of variations are at the protein C-terminus. N-terminal and cytoplasmic loop variants are also frequent, while variants in the extracellular loops or transmembrane domains are less common. Some receptors have more than one site at which variance can occur. The splicing variants appear to be functionally distinct, based upon observed differences in distribution, signaling, coupling, regulation, and ligand binding profiles (Kilpatrick, G. J. et al. (1999) Trends Pharmacol. Sci. 20:294-301).

GPCRs can be divided into three major subfamilies: the rhodopsin-like, secretin-like, and metabotropic glutamate receptor subfamilies. Members of these GPCR subfamilies share similar functions and the characteristic seven transmembrane structure, but have divergent amino acid sequences. The largest family consists of the rhodopsin-like GPCRs, which transmit diverse extracellular signals including hormones, neurotransmitters, and light. Rhodopsin is a photosensitive GPCR found in animal retinas. In vertebrates, rhodopsin molecules are embedded in membranous stacks found in photoreceptor (rod) cells. Each rhodopsin molecule responds to a photon of light by triggering a decrease in cGMP levels which leads to the closure of plasma membrane sodium channels. In this manner, a visual signal is converted to a neural impulse. Other rhodopsin-like GPCRs are directly involved in responding to neurotransmitters. These GPCRs include the receptors for adrenaline (adrenergic receptors), acetylcholine (muscarinic receptors), adenosine, galanin, and glutamate (N-methyl-D-aspartate/NMDA receptors). (Reviewed in Watson, S. and S. Arkinstall (1994) *The G-Protein Linked Receptor Facts Book*, Academic Press, San Diego Calif., pp. 7-9, 19-22, 32-35, 130-131, 214-216, 221-222; Habert-Ortoli, E. et al. (1994) Proc. Natl. Acad. Sci. USA 91:9780-9783.)

The galanin receptors mediate the activity of the neuroendocrine peptide galanin, which inhibits secretion of insulin, acetylcholine, serotonin and noradrenaline, and stimulates prolactin and growth hormone release. Galanin receptors are involved in feeding disorders, pain, depression, and Alzheimer's disease (Kask, K. et al. (1997) Life Sci. 60:1523-1533). Other nervous system rhodopsin-like GPCRs include a growing family of receptors for lysophosphatidic acid and other lysophospholipids, which appear to have roles in development and neuropathology (Chun, J. et al. (1999) Cell Biochem. Biophys. 30:213-242).

The largest subfamily of GPCRs, the olfactory receptors, are also members of the rhodopsin-like GPCR family. These receptors function by transducing odorant signals. Numerous distinct olfactory receptors are required to distinguish different odors. Each olfactory sensory neuron expresses only one type of olfactory receptor, and distinct spatial zones of neurons expressing distinct receptors are found in nasal passages. For example, the RA1c receptor which was isolated from a rat brain library, has been shown to be limited in expression to very distinct regions of the brain and a defined zone of the olfactory epithelium (Raming, K. et al. (1998) Receptors Channels 6:141-151). However, the expression of olfactory-like receptors is not confined to olfactory tissues. For example, three rat genes encoding olfactory-like receptors having typical GPCR characteristics showed expression patterns not only in taste and olfactory tissue, but also in male reproductive tissue (Thomas, M. B. et al. (1996) Gene 178: 1-5).

Members of the secretin-like GPCR subfamily have as their ligands peptide hormones such as secretin, calcitonin, glucagon, growth hormone-releasing hormone, parathyroid hormone, and vasoactive intestinal peptide. For example, the secretin receptor responds to secretin, a peptide hormone that stimulates the secretion of enzymes and ions in the pancreas and small intestine (Watson, supra, pp. 278-283). Secretin receptors are about 450 amino acids in length and are found in the plasma membrane of gastrointestinal cells. Binding of secretin to its receptor stimulates the production of cAMP.

Examples of secretin-like GPCRs implicated in inflammation and the immune response include the EGF module-containing, mucin-like hormone receptor (Emr1) and CD97 receptor proteins. These GPCRs are members of the recently characterized EGF-TM7 receptors subfamily. These seven transmembrane hormone receptors exist as heterodimers in vivo and contain between three and seven potential calcium-binding EGF-like motifs. CD97 is predominantly expressed in leukocytes and is markedly upregulated on activated B and T cells (McKnight, A. J. and S. Gordon (1998) J. Leukoc. Biol. 63:271-280).

The third GPCR subfamily is the metabotropic glutamate receptor family. Glutamate is the major excitatory neurotransmitter in the central nervous system. The metabotropic glutamate receptors modulate the activity of intracellular effectors, and are involved in long-term potentiation (Watson, supra, p. 130). The $Ca^{2+}$-sensing receptor, which senses changes in the extracellular concentration of calcium ions, has a large extracellular domain including clusters of acidic amino acids which may be involved in calcium binding. The metabotropic glutamate receptor family also includes pheromone receptors, the $GABA_B$ receptors, and the taste receptors.

Other subfamilies of GPCRs include two groups of chemoreceptor genes found in the nematodes *Caenorhabditis elegans* and *Caenorhabditis briggsae*, which are distantly related to the mammalian olfactory receptor genes. The yeast pheromone receptors STE2 and STE3, involved in the response to mating factors on the cell membrane, have their own seven-transmembrane signature, as do the cAMP receptors from the slime mold *Dictyostelium discoideum*, which are thought to regulate the aggregation of individual cells and control the expression of numerous developmentally-regulated genes.

GPCR mutations, which may cause loss of function or constitutive activation, have been associated with numerous human diseases (Coughlin, supra). For instance, retinitis pigmentosa may arise from mutations in the rhodopsin gene. Furthermore, somatic activating mutations in the thyrotropin receptor have been reported to cause hyperfunctioning thyroid adenomas, suggesting that certain GPCRs susceptible to constitutive activation may behave as protooncogenes (Parma, J. et al. (1993) Nature 365:649-651). GPCR receptors for the following ligands also contain mutations associated with human disease: luteinizing hormone (precocious puberty); vasopressin $V_2$ (X-linked nephrogenic diabetes); glucagon (diabetes and hypertension); calcium (hyperparathyroidism, hypocalcuria, hypercalcemia); parathyroid hormone (short limbed dwarfism); $\beta_3$-adrenoceptor (obesity, non-insulin-dependent diabetes mellitus); growth hormone releasing hormone (dwarfism); and adrenocorticotropin (glucocorticoid deficiency) (Wilson, S. et al. (1998) Br. J. Pharmocol. 125:1387-1392; Stadel, J. M. et al. (1997) Trends Pharmacol. Sci. 18:430-437). GPCRs are also involved in depression, schizophrenia, sleeplessness, hypertension, anxiety, stress, renal failure, and several cardiovascular disorders (Horn, F. and G. Vriend (1998) J. Mol. Med. 76:464-468).

In addition, within the past 20 years several hundred new drugs have been recognized that are directed towards activating or inhibiting GPCRs. The therapeutic targets of these drugs span a wide range of diseases and disorders, including cardiovascular, gastrointestinal, and central nervous system disorders as well as cancer, osteoporosis and endometriosis (Wilson, supra; Stadel, supra). For example, the dopamine agonist L-dopa is used to treat Parkinson's disease, while a dopamine antagonist is used to treat schizophrenia and the early stages of Huntington's disease. Agonists and antagonists of adrenoceptors have been used for the treatment of asthma, high blood pressure, other cardiovascular disorders, and anxiety; muscarinic agonists are used in the treatment of glaucoma and tachycardia; serotonin 5HT1D antagonists are used against migraine; and histamine H1 antagonists are used against allergic and anaphylactic reactions, hay fever, itching, and motion sickness (Horn, supra).

Recent research suggests potential future therapeutic uses for GPCRs in the treatment of metabolic disorders including diabetes, obesity, and osteoporosis. For example, mutant V2 vasopressin receptors causing nephrogenic diabetes could be functionally rescued in vitro by co-expression of a C-terminal V2 receptor peptide spanning the region containing the mutations. This result suggests a possible novel strategy for disease treatment (Schöneberg, T. et al. (1996) EMBO J. 15:1283-1291). Mutations in melanocortin-4 receptor (MC4R) are implicated in human weight regulation and obesity. As with the vasopressin V2 receptor mutants, these MC4R mutants are defective in trafficking to the plasma membrane (Ho, G. and R. G. MacKenzie (1999) J. Biol. Chem. 274:35816-35822), and thus might be treated with a similar strategy. The type 1 receptor for parathyroid hormone (PTH) is a GPCR that mediates the PTH-dependent regulation of calcium homeostasis in the bloodstream. Study of PTH/receptor interactions may enable the development of novel PTH receptor ligands for the treatment of osteoporosis (Mannstadt, M. et al. (1999) Am. J. Physiol. 277:F665-F675).

The chemokine receptor group of GPCRs have potential therapeutic utility in inflammation and infectious disease. (For review, see Locati, M. and P. M. Murphy (1999) Annu. Rev. Med. 50:425-440.) Chemokines are small polypeptides that act as intracellular signals in the regulation of leukocyte trafficking, hematopoiesis, and angiogenesis. Targeted disruption of various chemokine receptors in mice indicates that these receptors play roles in pathologic inflammation and in autoimmune disorders such as multiple sclerosis. Chemokine receptors are also exploited by infectious agents, including herpesviruses and the human immunodeficiency virus (HIV-1) to facilitate infection. A truncated version of chemokine receptor CCR5, which acts as a coreceptor for infection of T-cells by HIV-1, results in resistance to AIDS, suggesting that CCR5 antagonists could be useful in preventing the development of AIDS.

The discovery of new G-protein coupled receptors and the polynucleotides encoding them satisfies a need in the art by providing new compositions which are useful in the diagnosis, prevention, and treatment of cell proliferative, neurological, cardiovascular, gastrointestinal, autoimmune/inflammatory, and metabolic disorders, and viral infections, and in the assessment of the effects of exogenous compounds on the expression of nucleic acid and amino acid sequences of G-protein coupled receptors.

SUMMARY OF THE INVENTION

The invention features purified polypeptides, G-protein coupled receptors, referred to collectively as "GCREC" and individually as "GCREC-1," "GCREC-2," "GCREC-3," "GCREC-4," "GCREC-5," "GCREC-6," "GCREC-7," "GCREC-8," "GCREC-9," "GCREC-10," "GCREC-11," "GCREC-12," "GCREC-13," "GCREC-14," "GCREC-15," "GCREC-16," "GCREC-17," "GCREC-18," "GCREC-19," "GCREC-20," "GCREC-21," "GCREC-22," "GCREC-23," "GCREC-24," "GCREC-25," "GCREC-26," "GCREC-27," "GCREC-28," "GCREC-29," "GCREC-30," "GCREC-31," "GCREC-32," "GCREC-33," "GCREC-34," "GCREC-35," "GCREC-36," "GCREC-37," "GCREC-38," and "GCREC-39." In one aspect, the invention provides an isolated polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. In one alternative, the invention provides an isolated polypeptide comprising the amino acid sequence of SEQ ID NO:1-39.

The invention further provides an isolated polynucleotide encoding a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. In one alternative, the polynucleotide encodes a polypeptide selected from the group consisting of SEQ ID NO:1-39. In another alternative, the polynucleotide is selected from the group consisting of SEQ ID NO:40-78.

Additionally, the invention provides a recombinant polynucleotide comprising a promoter sequence operably linked to a polynucleotide encoding a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. In one alternative, the invention provides a cell transformed with the recombinant polynucleotide. In another alternative, the invention provides a transgenic organism comprising the recombinant polynucleotide.

The invention also provides a method for producing a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Additionally, the invention provides an isolated antibody which specifically binds to a polypeptide comprising an amino add sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39.

The invention further provides an isolated polynucleotide comprising a polynucleotide sequence selected from the group consisting of a) a polynucleotide sequence selected from the group consisting of SEQ ID NO:40-78, b) a naturally occurring polynucleotide sequence having at least 90% sequence identity to a polynucleotide sequence selected from the group consisting of SEQ ID NO:40-78, c) a polynucleotide sequence complementary to a), d) a polynucleotide sequence complementary to b), and e) an RNA equivalent of a)-d). In one alternative, the polynucleotide comprises at least 60 contiguous nucleotides.

Additionally, the invention provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:40-78, b) a naturally occurring polynucleotide sequence having at least 90% sequence identity to a polynucleotide sequence selected from the group consisting of SEQ ID NO:40-78, c) a polynucleotide sequence complementary to a), d) a polynucleotide sequence complementary to b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex, and optionally, if present, the amount thereof. In one alternative, the probe comprises at least 60 contiguous nucleotides.

The invention further provides a method for detecting a target polynucleotide in a sample, said target polynucleotide having a sequence of a polynucleotide comprising a polynucleotide sequence selected from the group consisting of a) a polynucleotide sequence selected from the group consisting of SEQ ID NO:40-78, b) a naturally occurring polynucleotide sequence having at least 90% sequence identity to a polynucleotide sequence selected from the group consisting of SEQ ID NO:40-78, c) a polynucleotide sequence complementary to a), d) a polynucleotide sequence complementary to b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof, and, optionally, if present, the amount thereof.

The invention further provides a composition comprising an effective amount of a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39, and a pharmaceutically acceptable excipient. In one embodiment, the composition comprises an amino acid sequence selected from the group consisting of SEQ ID NO:1-39. The invention additionally provides a method of treating a disease or condition associated with decreased expression of functional GCREC, comprising administering to a patient in need of such treatment the composition.

The invention also provides a method for screening a compound for effectiveness as an agonist of a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. The method comprises a) exposing a sample comprising the polypeptide to a compound, and b) detecting agonist activity in the sample. In one alternative, the invention provides a composition comprising an agonist compound identified by the method and a pharmaceutically acceptable excipient. In another alternative, the invention provides a method of treating a disease or condition associated with decreased expression of functional GCREC, comprising administering to a patient in need of such treatment the composition.

Additionally, the invention provides a method for screening a compound for effectiveness as an antagonist of a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. The method comprises a) exposing a sample comprising the polypeptide to a compound, and b) detecting antagonist activity in the sample. In one alternative, the invention provides a composition comprising an antagonist compound identified by the method and a pharmaceutically acceptable excipient. In another alternative, the invention provides a method of treating a disease or condition associated with overexpression of functional GCREC, comprising administering to a patient in need of such treatment the composition.

The invention further provides a method of screening for a compound that specifically binds to a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. The method comprises a) combining the polypeptide with at least one test compound under suitable conditions, and b) detecting binding of the polypeptide to the test compound, thereby identifying a compound that specifically binds to the polypeptide.

The invention further provides a method of screening for a compound that modulates the activity of a polypeptide comprising an amino acid sequence selected from the group consisting of a) an amino acid sequence selected from the group consisting of SEQ ID NO:1-39, b) a naturally occurring amino acid sequence having at least 90% sequence identity to an amino acid sequence selected from the group consisting of SEQ ID NO:1-39, c) a biologically active fragment of an amino acid sequence selected from the group consisting of SEQ ID NO:1-39, and d) an immunogenic fragment of an amino acid sequence selected from the group consisting of SEQ ID NO:1-39. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

The invention further provides a method for screening a compound for effectiveness in altering expression of a target polynucleotide, wherein said target polynucleotide comprises a sequence selected from the group consisting of SEQ ID NO:40-78, the method comprising a) exposing a sample comprising the target polynucleotide to a compound, and b) detecting altered expression of the target polynucleotide.

The invention further provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide comprising a polynucleotide sequence selected from the group consisting of i) a polynucleotide sequence selected from the group consisting of SEQ ID NO:40-78, ii) a naturally occurring polynucleotide sequence having at least 90% sequence identity to a polynucleotide sequence selected from the group consisting of SEQ ID NO:40-78, iii) a polynucleotide sequence complementary to i), iv) a polynucleotide sequence complementary to ii), and v) an RNA equivalent of i)-iv). Hybridization occurs under conditions whereby a specific hybridization complex is formed between said probe and a target polynucleotide in the biological sample, said target polynucleotide comprising a polynucleotide sequence selected from the group consisting of i) a polynucleotide sequence selected from the group consisting of SEQ ID NO:40-78, ii) a naturally occurring polynucleotide sequence having at least 90% sequence identity to a polynucleotide sequence selected from the group consisting of SEQ ID NO:40-78, iii) a polynucleotide sequence complementary to i), iv) a polynucleotide sequence complementary to ii), and v) an RNA equivalent of i)-iv). Alternatively, the target polynucleotide comprises a fragment of a polynucleotide sequence selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

BRIEF DESCRIPTION OF THE FIGURES AND TABLES

FIG. 1 shows the hydrophobicity plot for GCREC-1 (SEQ ID NO:1; Incyte ID number 104941CD1). The hydrophobicity plot was generated using the MacDNASIS Pro software. The positive X axis reflects amino acid position, and the negative Y axis, hydrophobicity. The numbers indicate the positions of predicted transmembrane domains.

Figure 1:
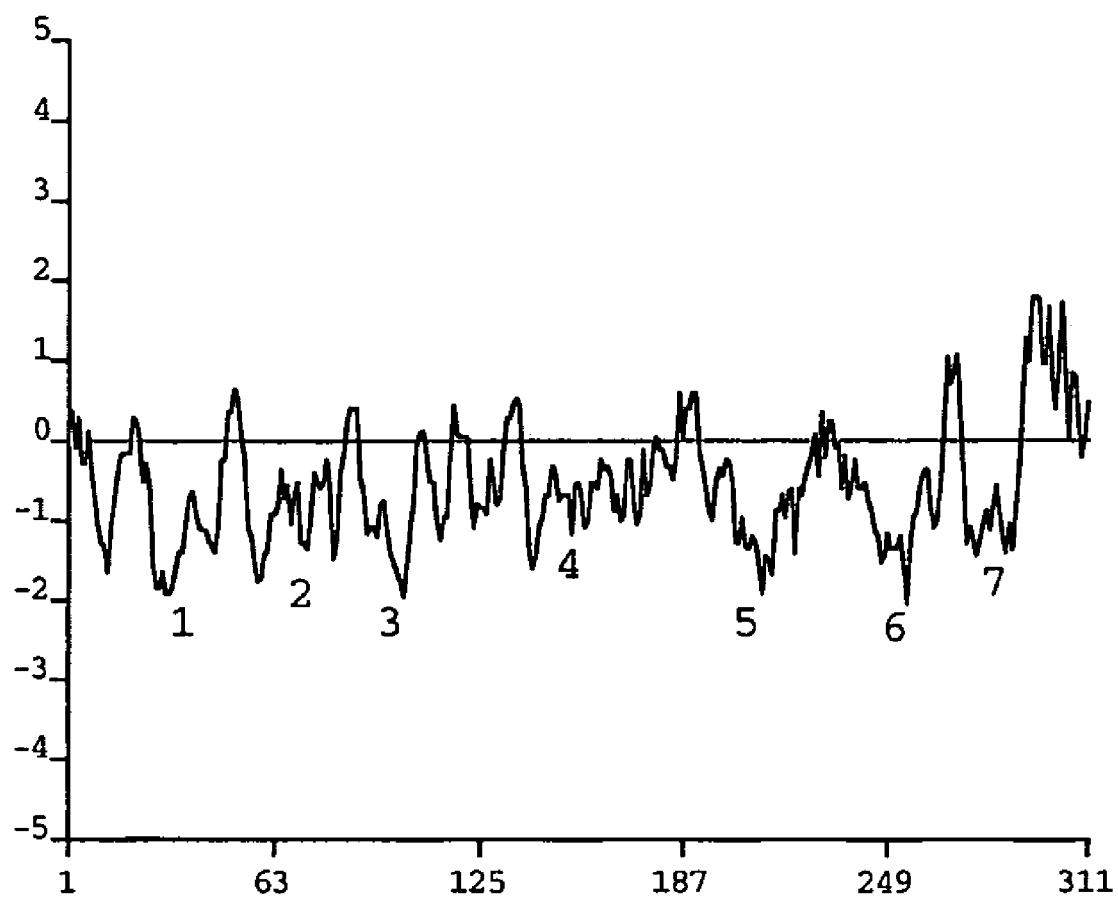
Figure 2:
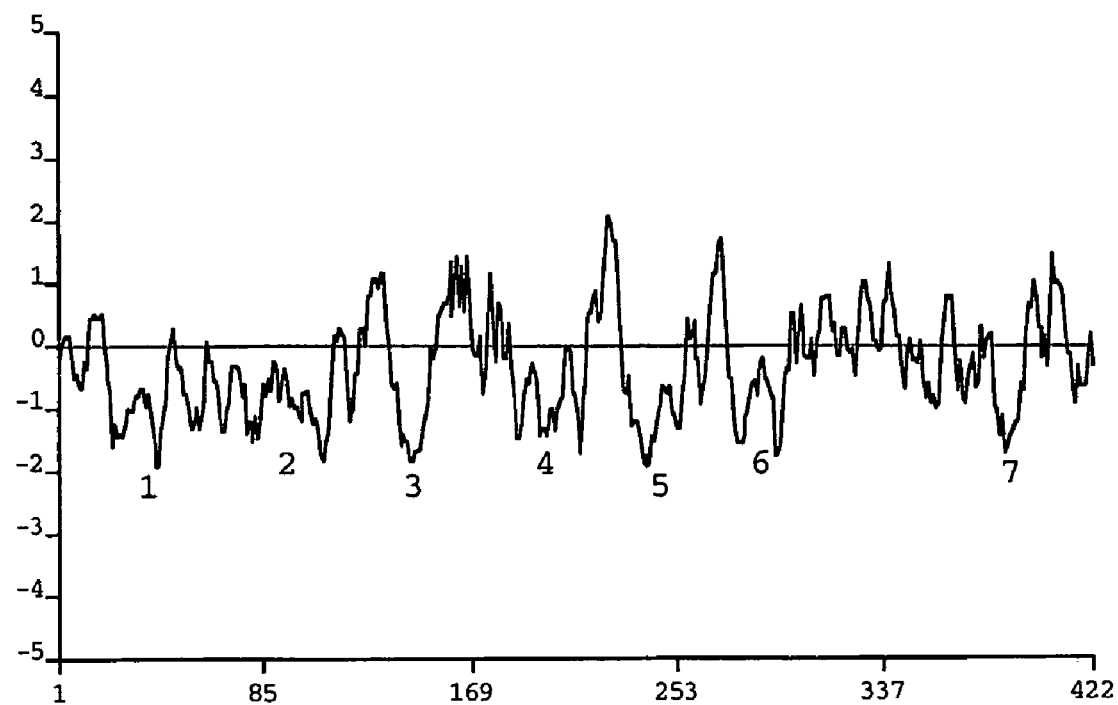
FIG. 2 shows the hydrophobicity plot for GCREC-3 (SEQ ID NO:3; Incyte ID number 3168839CD1).
Figure 3:
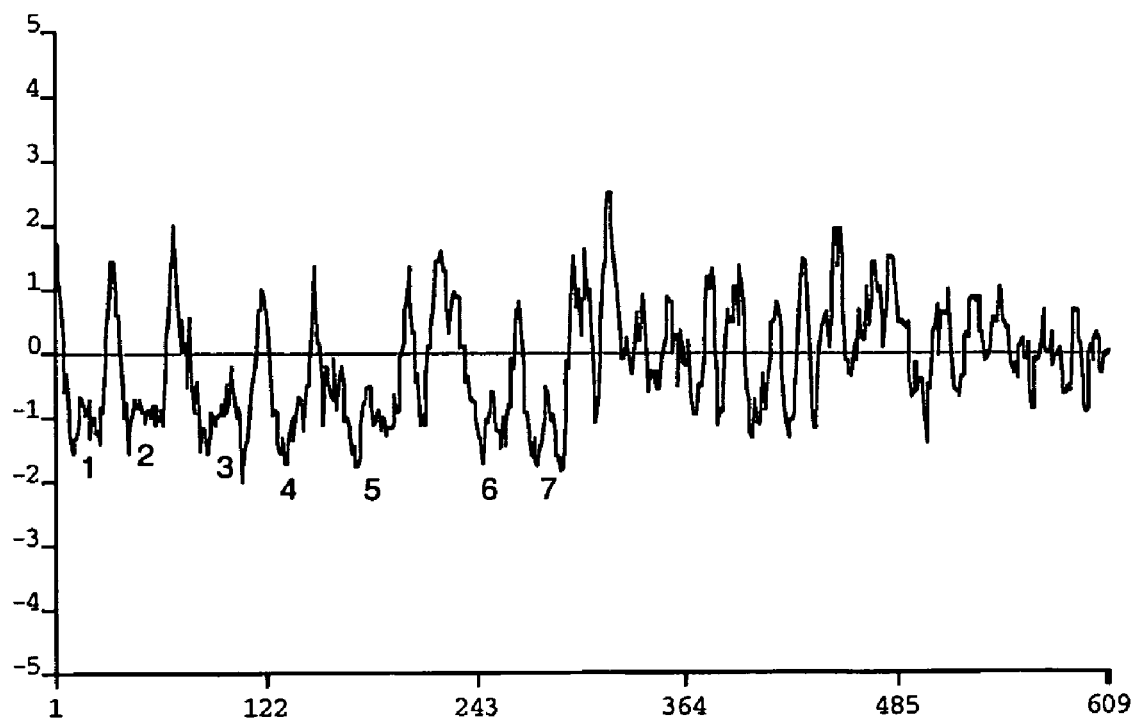
FIG. 3 shows the hydrophobicity plot for GCREC-4 (SEQ ID NO:4; Incyte ID number 3291235CD1).
Figure 4:
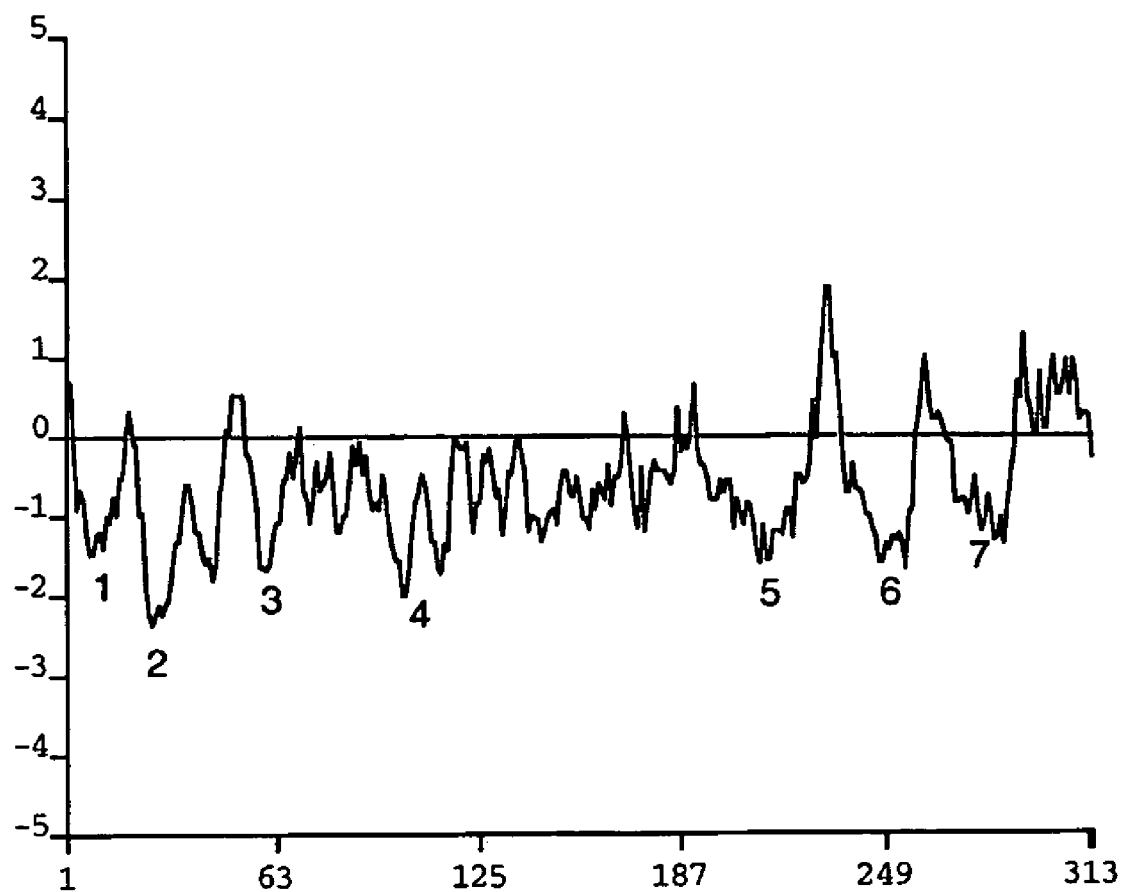
FIG. 4 shows the hydrophobicity plot for GCREC-5 (SEQ ID NO:5; Incyte ID number 7472001CD1).
Figure 5:
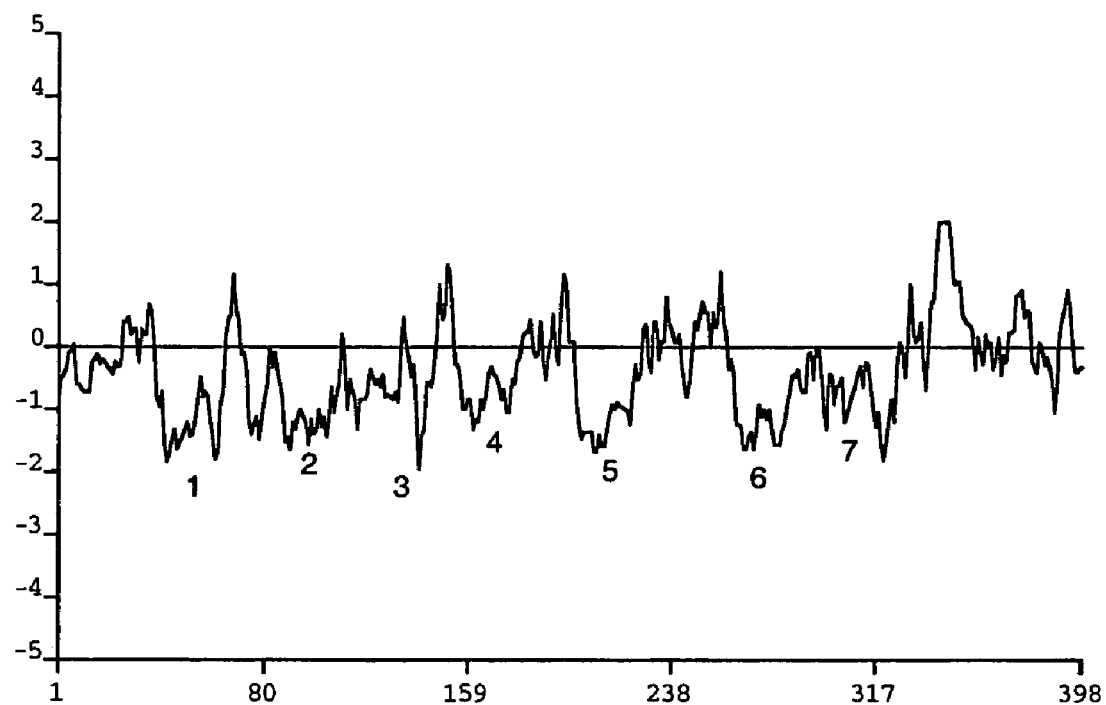
FIG. 5 shows the hydrophobicity plot for GCREC-6 (SEQ ID NO:6; Incyte ID number 7472003CD1).
Figure 6:
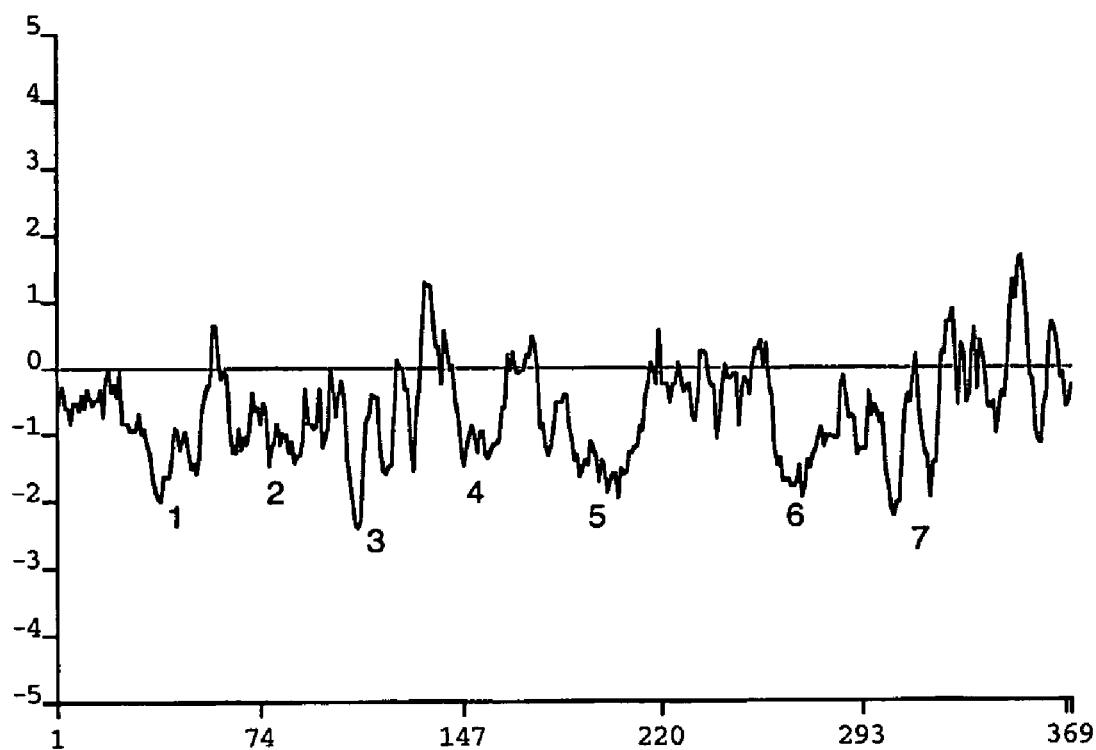
FIG. 6 shows the hydrophobicity plot for GCREC-7 (SEQ ID NO:7; Incyte ID number 7472004CD1).
Figure 7:
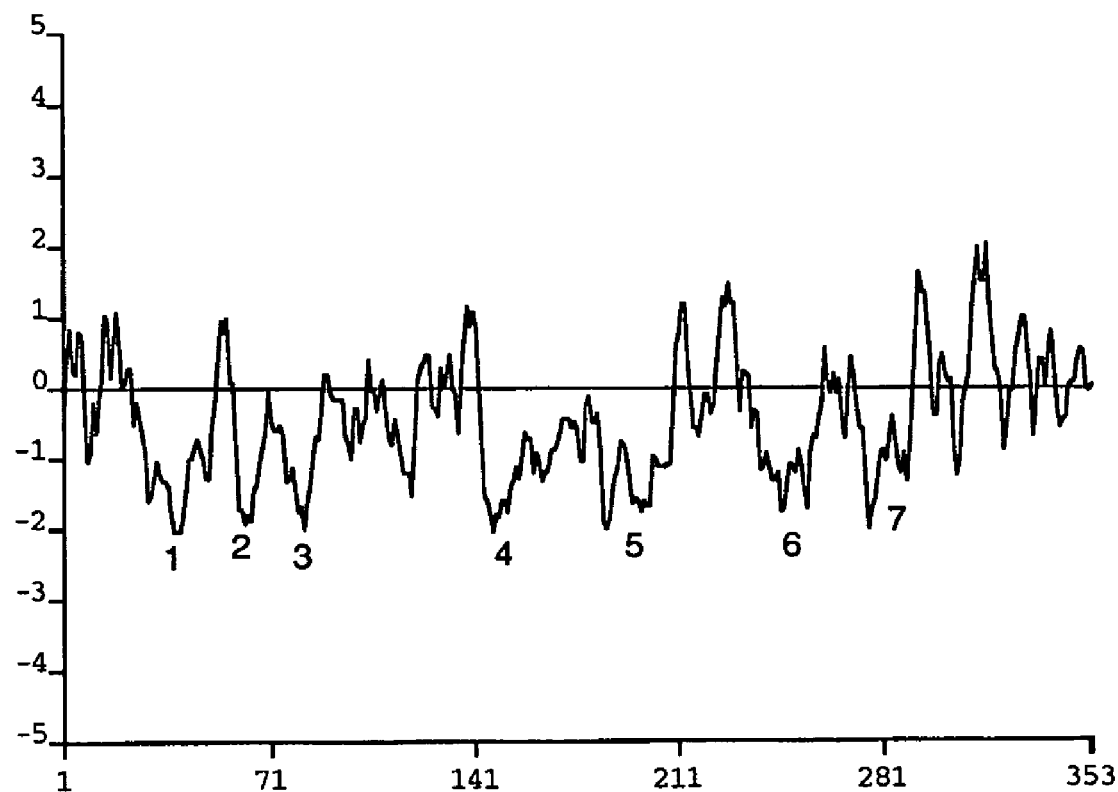
FIG. 7 shows the hydrophobicity plot for GCREC-19 (SEQ ID NO:19; Incyte ID number 3068234CD1).
Figure 8:
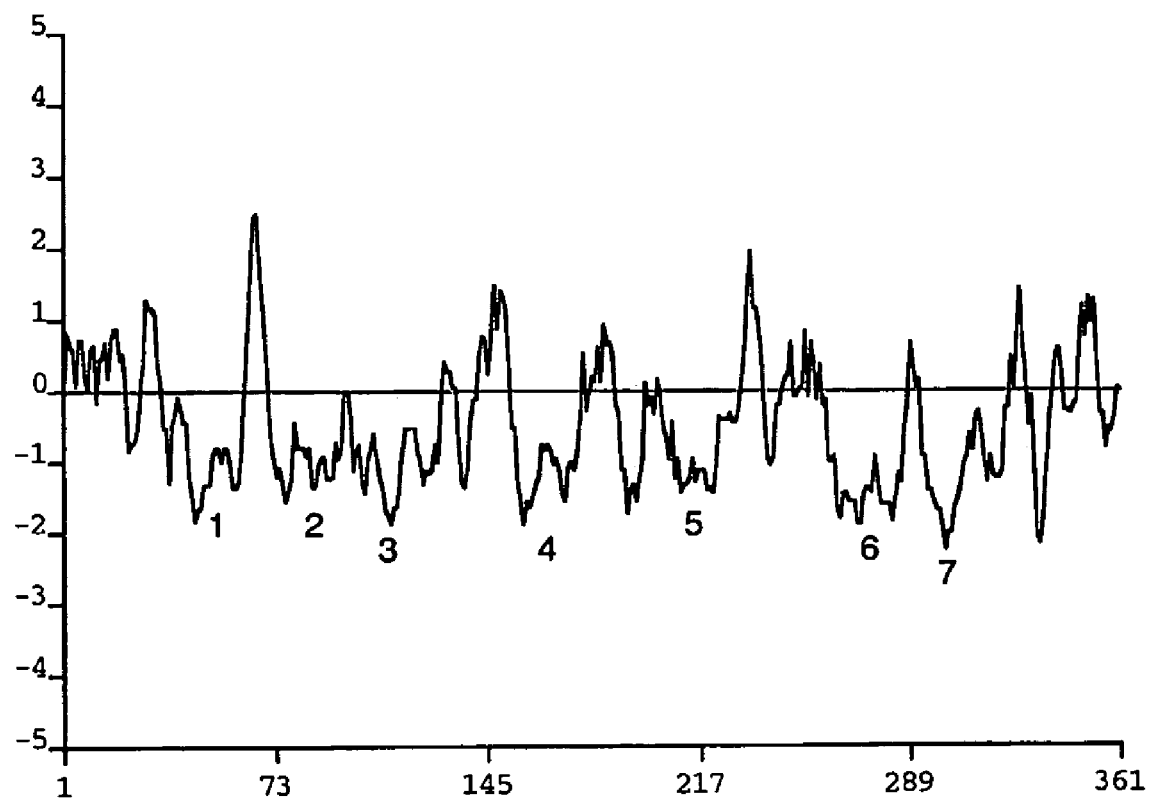
FIG. 8 shows the hydrophobicity plot for GCREC-20 (SEQ ID NO:20; Incyte ID number 5029478CD1).
Figure 9:
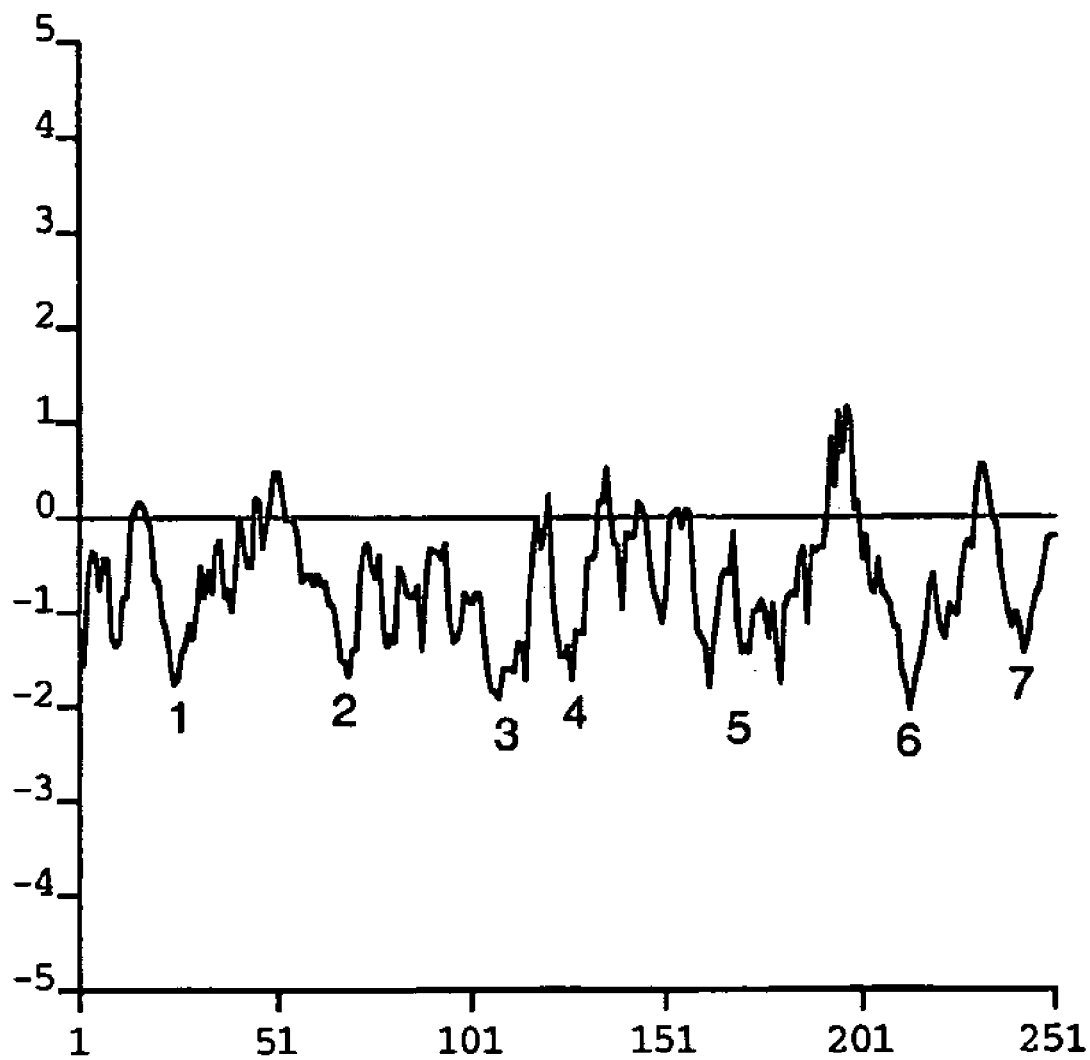
FIG. 9 shows the hydrophobicity plot for GCREC-21 (SEQ ID NO:21; Incyte ID number 5102576CD1).

Table 1 summarizes the nomenclature for the polynucleotide and polypeptide sequences of the present invention.

Table 2 shows the GenBank identification number and annotation of the nearest GenBank homolog for each polypeptide of the invention. The probability score for the match between each polypeptide and its GenBank homolog is also shown.

Table 3 shows structural features of each polypeptide sequence, including predicted motifs and domains, along with the methods, algorithms, and searchable databases used for analysis of each polypeptide.

Table 4 lists the cDNA and genomic DNA fragments which were used to assemble each polynucleotide sequence, along with selected fragments of the polynucleotide sequences.

Table 5 shows the representative cDNA library for each polynucleotide of the invention.

Table 6 provides an appendix which describes the tissues and vectors used for construction of the cDNA libraries shown in Table 5.

Table 7 shows the tools, programs, and algorithms used to analyze the polynucleotides and polypeptides of the invention, along with applicable descriptions, references, and threshold parameters.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"GCREC" refers to the amino acid sequences of substantially purified GCREC obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of GCREC. Agonists may include proteins, nucleic acids, carbohydrates, small molecules, or any other compound or composition which modulates the activity of GCREC either by directly interacting with GCREC or by acting on components of the biological pathway in which GCREC participates.

An "allelic variant" is an alternative form of the gene encoding GCREC. Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding GCREC include those sequences with deletions, insertions, or substitutions of different nucleotides, resulting in a polypeptide the same as GCREC or a polypeptide with at least one functional characteristic of GCREC. Included within this definition are polymorphisms which may or may not be readily detectable using a particular oligonucleotide probe of the polynucleotide encoding GCREC, and improper or unexpected hybridization to allelic variants, with a locus other than the normal chromosomal locus for the polynucleotide sequence encoding GCREC. The encoded protein may also be "altered" and may contain deletions, insertions, or substitutions of amino acid residues which produce a silent change and result in a functionally equivalent GCREC. Deliberate amino acid substitutions may be made on the basis of similarity in polarity, charge, solubility, hydrophobicity, hydrophilicity, and/or the amphipathic nature of the residues, as long as the biological or immunological activity of GCREC is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" refer to an oligopeptide, peptide, polypeptide, or protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which inhibits or attenuates the biological activity of GCREC. Antagonists may include proteins such as antibodies, nucleic acids, carbohydrates, small molecules, or any other compound or composition which modulates the activity of GCREC either by directly interacting with GCREC or by acting on components of the biological pathway in which GCREC participates.

The term "antibody" refers to intact immunoglobulin molecules as well as to fragments thereof, such as Fab, F(ab')$_2$, and Fv fragments, which are capable of binding an epitopic determinant. Antibodies that bind GCREC polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "antisense" refers to any composition capable of base-pairing with the "sense" (coding) strand of a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic GCREC, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide sequence" and a "composition comprising a given amino acid sequence" refer broadly to any composition containing the given polynucleotide or amino acid sequence. The composition may comprise a dry formulation or an aqueous solution. Compositions comprising polynucleotide sequences encoding GCREC or fragments of GCREC may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (GCG, Madison Wis.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

A "fragment" is a unique portion of GCREC or the polynucleotide encoding GCREC which is identical in sequence to but shorter in length than the parent sequence. A fragment may comprise up to the entire length of the defined sequence, minus one nucleotide/amino acid residue. For example, a fragment may comprise from 5 to 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:40-78 comprises a region of unique polynucleotide sequence that specifically identifies SEQ ID NO:40-78, for example, as distinct from any other sequence in the genome from which the fragment was obtained. A fragment of SEQ ID NO:40-78 is useful, for example, in hybridization and amplification technologies and in analogous methods that distinguish SEQ ID NO:40-78 from related polynucleotide sequences. The precise length of a fragment of SEQ ID NO:40-78 and the region of SEQ ID NO:40-78 to which the fragment corresponds are routinely determinable by one of ordinary skill in the art based on the intended purpose for the fragment.

A fragment of SEQ ID NO:1-39 is encoded by a fragment of SEQ ID NO:40-78. A fragment of SEQ ID NO:1-39 comprises a region of unique amino acid sequence that specifically identifies SEQ ID NO:1-39. For example, a fragment of SEQ ID NO:1-39 is useful as an immunogenic peptide The terms "percent identity" and "% identity," as applied to polynucleotide sequences, refer to the percentage of residue matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989) CABIOS 5:151-153 and in Higgins, D. G. et al. (1992) CABIOS 8:189-191. For pairwise alignments of polynucleotide sequences, the default parameters are set as follows: Ktuple=2, gap penalty=5, window=4, and "diagonals saved"=4. The "weighted" residue weight table is selected as the default. Percent identity is reported by CLUSTAL V as the "percent similarity" between aligned polynucleotide sequences.

Alternatively, a suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403-410), which is available from several sources, including the NCBI, Bethesda, Md., and on the Internet at http://www.ncbi.nlm.nih.gov/BLAST/. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively at http://www.ncbi.nlm.nih.gov/gorf/bl2.html. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table. As with polynucleotide alignments, the percent identity is reported by CLUSTAL V as the "percent similarity" between aligned polypeptide sequence pairs.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 µg/ml sheared, denatured salmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. et al. (1989) *Molecular Cloning: A Laboratory Manual*, $2^{nd}$ ed., vol. 1-3, Cold Spring Harbor Press, Plainview N.Y.; specifically see volume 2, chapter 9.

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block nonspecific hybridization. Such blocking reagents include, for instance, sheared and denatured salmon sperm DNA at about 100-200 µg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" and "addition" refer to changes in an amino acid or nucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of GCREC which is capable of eliciting an immune response when introduced into a living organism, for example, a mammal. The term "immunogenic fragment" also includes any polypeptide or oligopeptide fragment of GCREC which is useful in any of the antibody production methods disclosed herein or known in the art.

The term "microarray" refers to an arrangement of a plurality of polynucleotides, polypeptides, or other chemical compounds on a substrate.

The terms "element" and "array element" refer to a polynucleotide, polypeptide, or other chemical compound having a unique and defined position on a microarray.

The term "modulate" refers to a change in the activity of GCREC. For example, modulation may cause an increase or a decrease in protein activity, binding characteristics, or any other biological, functional, or immunological properties of GCREC.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation and may be pegylated to extend their lifespan in the cell.

"Post-translational modification" of an GCREC may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of GCREC.

"Probe" refers to nucleic acid sequences encoding GCREC, their complements, or fragments thereof, which are used to detect identical, allelic or related nucleic acid sequences. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid sequence, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in the references, for example Sambrook, J. et al. (1989) *Molecular Cloning: A Laboratory Manual*, $2^{nd}$ ed., vol. 1-3, Cold Spring Harbor Press, Plainview N.Y.; Ausubel, F. M. et al. (1987) *Current Protocols in Molecular Biology*, Greene Publ. Assoc. & Wiley-Intersciences, New York N.Y.; Innis, M. et al. (1990) *PCR Protocols, A Guide to Methods and Applications*, Academic Press, San Diego Calif. PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook, supra. The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA sequence, is composed of the same linear sequence of nucleotides as the reference DNA sequence with the exception that all occurrences of the nitrogenous base thymine are replaced with uracil, and the sugar backbone is composed of ribose instead of deoxyribose.

The term "sample" is used in its broadest sense. A sample suspected of containing GCREC, nucleic acids encoding GCREC, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least 60% free, preferably at least 75% free, and most preferably at least 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook et al. (1989), supra.

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 95% or at least 98% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternative splicing of exons during mRNA processing. The corresponding polypeptide may possess additional functional domains or lack domains that are present in the reference molecule. Species variants are polynucleotide sequences that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity to the particular polypeptide sequence over a certain length of one of the polypeptide sequences using blastp with the "BLAST 2 Sequences" tool Version 2.0.9 (May 7, 1999)

set at default parameters. Such a pair of polypeptides may show, for example, at least 50%, at least 60%, at least 70%, at least 80%, at least 90%, at least 95%, or at least 98% or greater sequence identity over a certain defined length of one of the polypeptides.

The Invention

The invention is based on the discovery of new human G-protein coupled receptors (GCREC), the polynucleotides encoding GCREC, and the use of these compositions for the diagnosis, treatment, or prevention of cell proliferative, neurological, cardiovascular, gastrointestinal, autoimmune/inflammatory, and metabolic disorders, and viral infections.

Table 1 summarizes the nomenclature for the polynucleotide and polypeptide sequences of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown.

Table 2 shows sequences with homology to the polypeptides of the invention as identified by BLAST analysis against the GenBank protein (genpept) database. Columns 1 and 2 show the polypeptide sequence identification number (Polypeptide SEQ ID NO:) and the corresponding Incyte polypeptide sequence number (Incyte Polypeptide ID) for each polypeptide of the invention. Column 3 shows the GenBank identification number (Genbank ID NO:) of the nearest GenBank homolog. Column 4 shows the probability score for the match between each polypeptide and its GenBank homolog. Column 5 shows the annotation of the GenBank homolog along with relevant citations where applicable, all of which are expressly incorporated by reference herein.

Table 3 shows various structural features of each of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Genetics Computer Group, Madison Wis.). Column 6 shows amino acid residues comprising signature sequences, domains, and motifs. Column 7 shows analytical methods for protein structure/function analysis and in some cases, searchable databases to which the analytical methods were applied.

As shown in Table 4, the polynucleotide sequences of the present invention were assembled using cDNA sequences or coding (exon) sequences derived from genomic DNA, or any combination of these two types of sequences. Columns 1 and 2 list the polynucleotide sequence identification number (Polynucleotide SEQ ID NO:) and the corresponding Incyte polynucleotide consensus sequence number (Incyte Polynucleotide ID) for each polynucleotide of the invention. Column 3 shows the length of each polynucleotide sequence in basepairs. Column 4 lists fragments of the polynucleotide sequences which are useful, for example, in hybridization or amplification technologies that identify SEQ ID NO:40-78 or that distinguish between SEQ ID NO:40-78 and related polynucleotide sequences. Column 5 shows identification numbers corresponding to cDNA sequences, coding sequences (exons) predicted from genomic DNA, and/or sequence assemblages comprised of both cDNA and genomic DNA. These sequences were used to assemble the polynucleotide sequences of the invention. Columns 6 and 7 of Table 4 show the nucleotide start (5') and stop (3') positions of the cDNA and genomic sequences in column 5 relative to their respective sequences.

The identification numbers in Column 5 of Table 4 may refer specifically, for example, to Incyte cDNAs along with their corresponding cDNA libraries. For example, 927003T6 is the identification number of an Incyte cDNA sequence, and BRAINOT04 is the cDNA library from which it is derived. Incyte cDNAs for which cDNA libraries are not indicated were derived from pooled cDNA libraries (e.g., 70489898V1). Alternatively, the identification numbers in column 5 may refer to GenBank cDNAs or ESTs (e.g., g835247) which contributed to the assembly of the polynucleotide sequences. Alternatively, the identification numbers in column 5 may refer to coding regions predicted by Genscan analysis of genomic DNA. For example, g4190944.v113.gs_10.edit is the identification number of a Genscan-predicted coding sequence, with g4190944 being the GenBank identification number of the sequence to which Genscan was applied. The Genscan-predicted coding sequences may have been edited prior to assembly. (See Example IV.) Alternatively, the identification numbers in column 5 may refer to assemblages of both cDNA and Genscan-predicted exons brought together by an "exon stitching" algorithm. (See Example V.) Alternatively, the identification numbers in column 5 may refer to assemblages of both cDNA and Genscan-predicted exons brought together by an "exon-stretching" algorithm. (See Example V.) In some cases, Incyte cDNA coverage redundant with the sequence coverage shown in column 5 was obtained to confirm the final consensus polynucleotide sequence, but the relevant Incyte cDNA identification numbers are not shown.

Table 5 shows the representative cDNA libraries for those polynucleotide sequences which were assembled using Incyte cDNA sequences. The representative cDNA library is the Incyte cDNA library which is most frequently represented by the Incyte cDNA sequences which were used to assemble and confirm the above polynucleotide sequences. The tissues and vectors which were used to construct the cDNA libraries shown in Table 5 are described in Table 6.

The invention also encompasses GCREC variants. A preferred GCREC variant is one which has at least about 80%, or alternatively at least about 90%, or even at least about 95% amino acid sequence identity to the GCREC amino add sequence, and which contains at least one functional or structural characteristic of GCREC.

The invention also encompasses polynucleotides which encode GCREC. In a particular embodiment, the invention encompasses a polynucleotide sequence comprising a sequence selected from the group consisting of SEQ ID NO:40-78, which encodes GCREC. The polynucleotide sequences of SEQ ID NO:40-78, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses a variant of a polynucleotide sequence encoding GCREC. In particular, such a variant polynucleotide sequence will have at least about 70%, or alternatively at least about 85%, or even at least about 95% polynucleotide sequence identity to the polynucleotide sequence encoding GCREC. A particular aspect of the invention encompasses a variant of a polynucleotide sequence comprising a sequence selected from the group consisting of SEQ ID NO:40-78 which has at least about 70%, or alternatively at least about 85%, or even at least about 95% polynucleotide sequence identity to a nucleic acid sequence selected from the group consisting of SEQ ID NO:40-78. Any one of the polynucleotide variants described above can encode an amino acid sequence which contains at least one functional or structural characteristic of GCREC.

It will be appreciated by those skilled in the art that as a result of the degeneracy of the genetic code, a multitude of polynucleotide sequences encoding GCREC, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring GCREC, and all such variations are to be considered as being specifically disclosed.

Although nucleotide sequences which encode GCREC and its variants are generally capable of hybridizing to the nucleotide sequence of the naturally occurring GCREC under appropriately selected conditions of stringency, it may be advantageous to produce nucleotide sequences encoding GCREC or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding GCREC and its derivatives without altering the encoded amino acid sequences include the production of RNA transcripts having more desirable properties, such as a greater half-life, than transcripts produced from the naturally occurring sequence.

The invention also encompasses production of DNA sequences which encode GCREC and GCREC derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding GCREC or any fragment thereof.

Also encompassed by the invention are polynucleotide sequences that are capable of hybridizing to the claimed polynucleotide sequences, and, in particular, to those shown in SEQ ID NO:40-78 and fragments thereof under various conditions of stringency. (See, e.g., Wahl, G. M. and S. L. Berger (1987) Methods Enzymol. 152:399-407; Kimmel, A. R. (1987) Methods Enzymol. 152:507-511.) Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 liquid transfer system (Hamilton Reno Nev.), PTC200 thermal cycler (MJ Research Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Molecular Dynamics, Sunnyvale Calif.), or other systems known in the art. The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biology and Biotechnology*, Wiley V C H, New York N.Y., pp. 856-853.)

The nucleic acid sequences encoding GCREC may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318-322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111-119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055-3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode GCREC may be cloned in recombinant DNA molecules that direct expression of GCREC, or fragments or functional equivalents thereof, in appropriate host cells. Due to the inherent degeneracy of the genetic code, other DNA sequences which encode substantially the same or a functionally equivalent amino acid sequence may be produced and used to express GCREC.

The nucleotide sequences of the present invention can be engineered using methods generally known in the art in order to alter GCREC-encoding sequences for a variety of purposes including, but not limited to, modification of the cloning, processing, and/or expression of the gene product DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULAR-BREEDING (Maxygen Inc., Santa Clara Calif.; described in U.S. Pat. No. 5,837,458; Chang, C.-C. et al. (1999) Nat. Biotechnol. 17:793-797; Christians, F. C. et al. (1999) Nat. Biotechnol. 17:259-264; and Crameri, A. et al. (1996) Nat. Biotechnol. 14:315-319) to alter or improve the biological properties of GCREC, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, sequences encoding GCREC may be synthesized in whole or in part, using chemical methods well known in the art. (See, e.g., Caruthers, M. H. et al. (1980) Nucleic Acids Symp. Ser. 7:215-223; and Horn, T. et al. (1980) Nucleic Acids Symp. Ser. 7:225-232.) Alternatively, GCREC itself or a fragment thereof may be synthesized using chemical methods. For example, peptide synthesis can be performed using various solution-phase or solid-phase techniques. (See, e.g., Creighton, T. (1984) *Proteins, Structures and Molecular Properties*, WH Freeman, New York N.Y., pp. 55-60; and Roberge, J. Y. et al. (1995) Science 269:202-204.) Automated synthesis may be achieved using the ABI 431A peptide synthesizer (Applied Biosystems). Additionally, the amino acid sequence of GCREC, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography. (See, e.g., Chiez, R. M. and F. Z. Regnier (1990) Methods Enzymol. 182:392-421.) The composition of the synthetic peptides may be confirmed by amino acid analysis or by sequencing. (See, e.g., Creighton, supra, pp. 28-53.)

In order to express a biologically active GCREC, the nucleotide sequences encoding GCREC or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding GCREC. Such elements may vary in their strength and specificity. Specific initiation signals may also be used to achieve more efficient translation of sequences encoding GCREC. Such signals include the ATG initiation codon and adjacent sequences, e.g. the Kozak sequence. In cases where sequences encoding GCREC and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125-162.)

Methods which are well known to those skilled in the art may be used to construct expression vectors containing sequences encoding GCREC and appropriate transcriptional and translational control elements. These methods include in vitro recombinant DNA techniques, synthetic techniques, and in vivo genetic recombination. (See, e.g., Sambrcok, J. et al. (1989) *Molecular Cloning, A Laboratory Manual*, Cold Spring Harbor Press, Plainview N.Y., ch. 4, 8, and 16-17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding GCREC. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. (See, e.g., Sambrook, supra; Ausubel, supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; *The McGraw Hill Yearbook of Science and Technology* (1992) McGraw Hill, New York N.Y., pp. 191-196; Logan, J. and T. Shenk (1984) Proc. Natl. Acad. Sci. USA 81:3655-3659; and Harrington, J. J. et al. (1997) Nat. Genet. 15:345-355.) Expression vectors derived from retroviruses, adenoviruses, or herpes or vaccinia viruses, or from various bacterial plasmids, may be used for delivery of nucleotide sequences to the targeted organ, tissue, or cell population. (See, e.g., Di Nicola, M. et al. (1998) Cancer Gen. Ther.

5(6):350-356; Yu, M. et al. (1993) Proc. Natl. Acad. Sci. USA 90(13):6340-6344; Buller, R. M. et al. (1985) Nature 317 (6040):813-815; McGregor, D. P. et al. (1994) Mol. Immunol. 31(3):219-226; and Verma, I. M. and N. Somia (1997) Nature 389:239-242.) The invention is not limited by the host cell employed.

In bacterial systems, a number of cloning and expression vectors may be selected depending upon the use intended for polynucleotide sequences encoding GCREC. For example, routine cloning, subcloning, and propagation of polynucleotide sequences encoding GCREC can be achieved using a multifunctional E. coli vector such as PBLUESCRIPT (Stratagene, La Jolla Calif.) or PSPORT1 plasmid (Life Technologies). Ligation of sequences encoding GCREC into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503-5509.) When large quantities of GCREC are needed, e.g. for the production of antibodies, vectors which direct high level expression of GCREC may be used. For example, vectors containing the strong, inducible SP6 or T7 bacteriophage promoter may be used.

Yeast expression systems may be used for production of GCREC. A number of vectors containing constitutive or inducible promoters, such as alpha factor, alcohol oxidase, and PGH promoters, may be used in the yeast Saccharomyces cerevisiae or Pichia pastoris. In addition, such vectors direct either the secretion or intracellular retention of expressed proteins and enable integration of foreign sequences into the host genome for stable propagation. (See, e.g., Ausubel, 1995, supra; Bitter, G. A. et al. (1987) Methods Enzymol. 153:516-544; and Scorer, C. A. et al. (1994) Bio/Technology 12:181-184.)

Plant systems may also be used for expression of GCREC. Transcription of sequences encoding GCREC may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used. (See, e.g., Coruzzi, G. et al. (1984) EMBO J. 3:1671-1680; Broglie, R. et al. (1984) Science 224:838-843; and Winter, J. et al. (1991) Results Probl. Cell Differ. 17:85-105.) These constructs can be introduced into plant cells by direct DNA transformation or pathogen-mediated transfection. (See, e.g., The McGraw Hill Yearbook of Science and Technology (1992) McGraw Hill, New York N.Y., pp. 191-196.)

In mammalian cells, a number of viral-based expression systems may be utilized. In cases where an adenovirus is used as an expression vector, sequences encoding GCREC may be ligated into an adenovirus transcription/translation complex consisting of the late promoter and tripartite leader sequence. Insertion in a non-essential E1 or E3 region of the viral genome may be used to obtain infective virus which expresses GCREC in host cells. (See, e.g., Logan, J. and T. Shenk (1984) Proc. Natl. Acad. Sci. USA 81:3655-3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat. Genet. 15:345-355.)

For long term production of recombinant proteins in mammalian systems, stable expression of GCREC in cell lines is preferred. For example, sequences encoding GCREC can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk$^-$ and apr$^-$ cells, respectively. (See, e.g., Wigler, M. et al. (1977) Cell 11:223-232; Lowy, I. et al. (1980) Cell 22:817-823.) Also, antimetabolite, antibiotic, or herbicide resistance can be used as the basis for selection. For example, dhfr confers resistance to methotrexate; neo confers resistance to the aminoglycosides neomycin and G-418; and als and pat confer resistance to chlorsulfuron and phosphinotricin acetyltransferase, respectively. (See, e.g., Wigler, M. et al. (1980) Proc. Natl. Acad. Sci. USA 77:3567-3570; Colbere-Garapin, F. et al. (1981) J. Mol. Biol. 150:1-14.) Additional selectable genes have been described, e.g., trpB and hisD, which alter cellular requirements for metabolites. (See, e.g., Hartman, S. C. and R. C. Mulligan (1988) Proc. Natl. Acad. Sci. USA 85:8047-8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121-131.)

Although the presence/absence of marker gene expression suggests that the gene of interest is also present, the presence and expression of the gene may need to be confirmed. For example, if the sequence encoding GCREC is inserted within a marker gene sequence, transformed cells containing sequences encoding GCREC can be identified by the absence of marker gene function. Alternatively, a marker gene can be placed in tandem with a sequence encoding GCREC under the control of a single promoter. Expression of the marker gene in response to induction or selection usually indicates expression of the tandem gene as well.

In general, host cells that contain the nucleic acid sequence encoding GCREC and that express GCREC may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of GCREC using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on GCREC is preferred, but a competitive binding assay may be employed. These and other assays are well known in the art. (See, e.g., Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; and Pound, J. D. (1998) *Immunochemical Protocols*, Humana Press, Totowa N.J.)

A wide variety of labels and conjugation techniques are known by those skilled in the art and may be used in various nucleic acid and amino add assays. Means for producing labeled hybridization or PCR probes for detecting sequences related to polynucleotides encoding GCREC include oligo-labeling, nick translation, end-labeling, or PCR amplification using a labeled nucleotide. Alternatively, the sequences encoding GCREC, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding GCREC may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode GCREC may be designed to contain signal sequences which direct secretion of GCREC through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and W138) are available from the American Type Culture Collection (ATCC, Manassas Va.) and may be chosen to ensure the correct modification and processing of the foreign protein.

In another embodiment of the invention, natural, modified, or recombinant nucleic acid sequences encoding GCREC may be ligated to a heterologous sequence resulting in translation of a fusion protein in any of the aforementioned host systems. For example, a chimeric GCREC protein containing a heterologous moiety that can be recognized by a commercially available antibody may facilitate the screening of peptide libraries for inhibitors of GCREC activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the GCREC encoding sequence and the heterologous protein sequence, so that GCREC may be cleaved away from the heterologous moiety following purification. Methods for fusion protein expression and purification are discussed in Ausubel (1995, supra, ch. 10). A variety of commercially available kits may also be used to facilitate expression and purification of fusion proteins.

In a further embodiment of the invention, synthesis of radiolabeled GCREC may be achieved in vitro using the TNT rabbit reticulocyte lysate or wheat germ extract system (Promega). These systems couple transcription and translation of protein-coding sequences operably associated with the T7, T3, or SP6 promoters. Translation takes place in the presence of a radiolabeled amino acid precursor, for example, $^{35}$S-methionine.

GCREC of the present invention or fragments thereof may be used to screen for compounds that specifically bind to GCREC. At least one and up to a plurality of test compounds may be screened for specific binding to GCREC. Examples of test compounds include antibodies, oligonucleotides, proteins (e.g., receptors), or small molecules.

In one embodiment, the compound thus identified is closely related to the natural ligand of GCREC, e.g., a ligand or fragment thereof, a natural substrate, a structural or functional mimetic, or a natural binding partner. (See, e.g., Coligan, J. E. et al. (1991) *Current Protocols in Immunology* 1(2): Chapter 5.) Similarly, the compound can be closely related to the natural receptor to which GCREC binds, or to at least a fragment of the receptor, e.g., the ligand binding site. In either case, the compound can be rationally designed using known techniques. In one embodiment, screening for these compounds involves producing appropriate cells which express GCREC, either as a secreted protein or on the cell membrane. Preferred cells include cells from mammals, yeast, *Drosophila*, or *E. coli*. Cells expressing GCREC or cell membrane fractions which contain GCREC are then contacted with a test compound and binding, stimulation, or inhibition of activity of either GCREC or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with GCREC, either in solution or affixed to a solid support, and detecting the binding of GCREC to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

GCREC of the present invention or fragments thereof may be used to screen for compounds that modulate the activity of GCREC. Such compounds may include agonists, antagonists, or partial or inverse agonists. In one embodiment, an assay is performed under conditions permissive for GCREC activity, wherein GCREC is combined with at least one test compound, and the activity of GCREC in the presence of a test compound is compared with the activity of GCREC in the absence of the test compound. A change in the activity of GCREC in the presence of the test compound is indicative of a compound that modulates the activity of GCREC. Alternatively, a test compound is combined with an in vitro or cell-free system comprising GCREC under conditions suitable for GCREC activity, and the assay is performed. In either of these assays, a test compound which modulates the activity of GCREC may do so indirectly and need not come in direct contact with the test compound. At least one and up to a plurality of test compounds may be screened.

In another embodiment, polynucleotides encoding GCREC or their mammalian homologs may be "knocked out" in an animal model system using homologous recombination in embryonic stem (ES) cells. Such techniques are well known in the art and are useful for the generation of animal models of human disease. (See, e.g., U.S. Pat. No. 5,175,383 and U.S. Pat. No. 5,767,337.) For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288-1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999-2002; Wagner, K. U. et al. (1997) Nucleic Acids Res. 25:4323-4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding GCREC may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282: 1145-1147).

Polynucleotides encoding GCREC can also be used to create "knockin" humanized animals (pigs) or transgenic animals (mice or rats) to model human disease. With knockin technology, a region of a polynucleotide encoding GCREC is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress GCREC, e.g., by secreting GCREC in its milk, may also serve as a convenient source of that protein (Janne, J. et al. (1998) Biotechnol. Annu. Rev. 4:55-74).

Therapeutics

Chemical and structural similarity, e.g., in the context of sequences and motifs, exists between regions of GCREC and G-protein coupled receptors. In addition, the expression of GCREC is closely associated with cancerous, neurological, gastrointestinal, and lung tissue. Therefore, GCREC appears to play a role in cell proliferative, neurological, cardiovascular, gastrointestinal, autoimmune/inflammatory, and metabolic disorders, and viral infections. In the treatment of disorders associated with increased GCREC expression or activity, it is desirable to decrease the expression or activity of GCREC. In the treatment of disorders associated with decreased GCREC expression or activity, it is desirable to increase the expression or activity of GCREC.

Therefore, in one embodiment, GCREC or a fragment or derivative thereof may be administered to a subject to treat or prevent a disorder associated with decreased expression or activity of GCREC. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation; a gastrointestinal disorder such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, $alpha_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a metabolic disorder such as diabetes, obesity, and osteoporosis; and an infection by a viral agent classified as adenovirus, arenavirus, bunyavirus, calicivirus, coronavirus, filovirus, hepadnavirus, herpesvirus, flavivirus, orthomyxovirus, parvovirus, papovavirus, paramyxovirus, picornavirus, poxvirus, reovirus, retrovirus, rhabdovirus, and togavirus.

In another embodiment, a vector capable of expressing GCREC or a fragment or derivative thereof may be administered to a subject to treat or prevent a disorder associated with decreased expression or activity of GCREC including, but not limited to, those described above.

In a further embodiment, a composition comprising a substantially purified GCREC in conjunction with a suitable pharmaceutical carrier may be administered to a subject to treat or prevent a disorder associated with decreased expression or activity of GCREC including, but not limited to, those provided above.

In still another embodiment, an agonist which modulates the activity of GCREC may be administered to a subject to treat or prevent a disorder associated with decreased expression or activity of GCREC including, but not limited to, those listed above.

In a further embodiment, an antagonist of GCREC may be administered to a subject to treat or prevent a disorder associated with increased expression or activity of GCREC. Examples of such disorders include, but are not limited to, those cell proliferative, neurological, cardiovascular, gastrointestinal, autoimmune/inflammatory, and metabolic disorders, and viral infections, described above. In one aspect, an antibody which specifically binds GCREC may be used directly as an antagonist or indirectly as a targeting or delivery mechanism for bringing a pharmaceutical agent to cells or tissues which express GCREC.

In an additional embodiment, a vector expressing the complement of the polynucleotide encoding GCREC may be administered to a subject to treat or prevent a disorder associated with increased expression or activity of GCREC including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of GCREC may be produced using methods which are generally known in the art. In particular, purified GCREC may be used to produce antibodies or to screen libraries of pharmaceutical agents to identify those which specifically bind GCREC. Antibodies to GCREC may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are generally preferred for therapeutic use.

For the production of antibodies, various hosts including goats, rabbits, rats, mice, humans, and others may be immunized by injection with GCREC or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to GCREC have an amino acid sequence consisting of at least about 5 amino acids, and generally will consist of at least about 10 amino acids. It is also preferable that these oligopeptides, peptides, or fragments are identical to a portion of the amino acid sequence of the natural protein. Short stretches of GCREC amino acids may be fused with those of another protein, such as KLH, and antibodies to the chimeric molecule may be produced.

Monoclonal antibodies to GCREC may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; and Cole, S. P. et al. (1984) Mol. Cell Biol. 62:109-120.)

In addition, techniques developed for the production of "chimeric antibodies," such as the splicing of mouse antibody genes to human antibody genes to obtain a molecule with appropriate antigen specificity and biological activity, can be used (See, e.g., Morrison, S. L. et al. (1984) Proc. Natl. Acad. Sci. USA 81:6851-6855; Neuberger, M. S. et al. (1984) Nature 312:604-608; and Takeda, S. et al. (1985) Nature 314:452-454.) Alternatively, techniques described for the production of single chain antibodies may be adapted, using methods known in the art, to produce GCREC-specific single chain antibodies. Antibodies with related specificity, but of distinct idiotypic composition, may be generated by chain shuffling from random combinatorial immunoglobulin libraries. (See, e.g., Burton, D. R. (1991) Proc. Natl. Acad. Sci. USA 88:10134-10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. USA 86:3833-3837; Winter, G. et al. (1991) Nature 349:293-299.)

Antibody fragments which contain specific binding sites for GCREC may also be generated. For example, such fragments include, but are not limited to, $F(ab')_2$ fragments produced by pepsin digestion of the antibody molecule and Fab fragments generated by reducing the disulfide bridges of the $F(ab')2$ fragments. Alternatively, Fab expression libraries may be constructed to allow rapid and easy identification of monoclonal Fab fragments with the desired specificity. (See, e.g., Huse, W. D. et al. (1989) Science 246:1275-1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between GCREC and its specific antibody. A two-site, monoclonal-based immunoassay utilizing monoclonal antibodies reactive to two non-interfering GCREC epitopes is generally used, but a competitive binding assay may also be employed (Pound, supra).

Various methods such as Scatchard analysis in conjunction with radioimmunoassay techniques may be used to assess the affinity of antibodies for GCREC. Affinity is expressed as an association constant, $K_a$, which is defined as the molar concentration of GCREC-antibody complex divided by the molar concentrations of free antigen and free antibody under equilibrium conditions. The $K_a$ determined for a preparation of polyclonal antibodies, which are heterogeneous in their affinities for multiple GCREC epitopes, represents the average affinty, or avidity, of the antibodies for GCREC. The $K_a$ determined for a preparation of monoclonal antibodies, which are monospecific for a particular GCREC epitope, represents a true measure of affinity. High-affinity antibody preparations with $K_a$ ranging from about $10^9$ to $10^{12}$ L/mole are preferred for use in immunoassays in which the GCREC-antibody complex must withstand rigorous manipulations. Low-affinity antibody preparations with $K_a$ ranging from about $10^6$ to $10^7$ L/mole are preferred for use in immunopurification and similar procedures which ultimately require dissociation of GCREC, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is generally employed in procedures requiring precipitation of GCREC-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding GCREC, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding GCREC. Such technology is well known in the art, and antisense oligonucleotides or larger fragments can be (designed from various locations along the coding or control regions of sequences encoding GCREC. (See, e.g., Agrawal, S., ed. (1996) *Antisense Therapeutics*, Humana Press Inc., Totawa N.J.)

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein. (See, e.g., Slater, J. E. et al., (1998) J. Allergy Cli. Immunol. 102(3):469-475; and Scanlon, K. J. et al. (1995) 9(13): 1288-1296.) Antisense sequences can also be introduced intracellularly through the use of viral vectors, such as retrovirus and adeno-associated virus vectors. (See, e.g., Miller, A. D. (1990) Blood 76:271; Ausubel, supra; Uckert, W. and W. Walther (1994) Pharmacol. Ther. 63(3):323-347.) Other gene delivery mechanisms include liposome-derived systems, artificial viral envelopes, and other systems known in the art. (See, e.g., Rossi, J. J. (1995) Br. Med. Bull. 51(1): 217-225; Boado, R. J. et al. (1998) J. Pharm. Sci. 87(11): 1308-1315; and Morris, M. C. et al. (1997) Nucleic Acids Res. 25(14):2730-2736.)

In another embodiment of the invention, polynucleotides encoding GCREC may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669-672), severe combined immunodeficiency syndrome associated with an inherited adenosine deaminase (ADA) deficiency (Blaese, R. M. et al. (1995) Science 270: 475-480; Bordignon, C. et al. (1995) Science 270:470-475), cystic fibrosis (Zabner, J. et al. (1993) Cell 75:207-216; Crystal, R. G. et al. (1995) Hum. Gene Therapy 6:643-666; Crystal, R. G. et al. (1995) Hum. Gene Therapy 6:667-703), thalassamias, familial hypercholesterolemia, and hemophilia resulting from Factor VIII or Factor IX deficiencies (Crystal, R. G. (1995) Science 270:404-410; Verma, I. M. and N. Somia (1997) Nature 389:239-242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HIV) (Baltimore, D. (1988) Nature 335:

395-396; Poeschla, E. et al. (1996) Proc. Natl. Acad. Sci. USA. 93:11395-11399), hepatitis B or C virus (HBV, HCV); fungal parasites, such as *Candida albicans* and *Paracoccidioides brasillensis*; and protozoan parasites such as *Plasmodium falciparum* and *Trypanosoma cruzi*). In the case where a genetic deficiency in GCREC expression or regulation causes disease, the expression of GCREC from an appropriate population of transduced cells may alleviate the clinical manifestations caused by the genetic deficiency.

In a further embodiment of the invention, diseases or disorders caused by deficiencies in GCREC are treated by constructing mammalian expression vectors encoding GCREC and introducing these vectors by mechanical means into GCREC-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191-217; Ivics, Z. (1997) Cell 91:501-510; Boulay, J-L. and H. Récipon (1998) Curr. Opin. Biotechnol. 9:445-450).

Expression vectors that may be effective for the expression of GCREC include, but are not limited to, the PCDNA 3.1, EPITAG, PRCCMV2, PREP, PVAX vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). GCREC may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. U.S.A. 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and Blau, H. M. supra)), or (iii) a tissue-specific promoter or the native promoter of the endogenous gene encoding GCREC from a normal individual.

Commercially available liposome transformation kits (e.g., the PERFECT LIPID TRANSFECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456-467), or by electroporation (Neumann, E. et al. (1982) EMBO J. 1:841-845). The introduction of DNA to primary cells requires modification of these standardized mammalian transfection protocols.

In another embodiment of the invention, diseases or disorders caused by genetic defects with respect to GCREC expression are treated by constructing a retrovirus vector consisting of (i) the polynucleotide encoding GCREC under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, I. et al. (1995) Proc. Natl. Acad. Sci. U.S.A. 92:6733-6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647-1650; Bender, M. A. et al. (1987) J. Virol. 61:1639-1646; Adam, M. A. and A. D. Miller (1988) J. Virol. 62:3802-3806; Dull, T. et al. (1998) J. Virol. 72:8463-8471; Zufferey, R. et al. (1998) J. Virol. 72:9873-9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4+ T-cells), and the return of transduced cells to a patient are procedures well known to persons skilled in the art of gene therapy and have been well documented (Ranga, U. et al. (1997) J. Virol. 71:7020-7029; Bauer, G. et al. (1997) Blood 89:2259-2267; Bonyhadi, M. L. (1997) J. Virol. 71:4707-4716; Ranga, U. et al. (1998) Proc. Natl. Acad. Sci. U.S.A. 95:1201-1206; Su, L. (1997) Blood 89:2283-2290).

In the alternative, an adenovirus-based gene therapy delivery system is used to deliver polynucleotides encoding GCREC to cells which have one or more genetic abnormalities with respect to the expression of GCREC. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263-268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999) Annu. Rev. Nutr. 19:511-544 and Verma, I. M. and N. Somia (1997) Nature 18:389:239-242, both incorporated by reference herein.

In another alternative, a herpes-based, gene therapy delivery system is used to deliver polynucleotides encoding GCREC to target cells which have one or more genetic abnormalities with respect to the expression of GCREC. The use of herpes simplex virus (HSV)-based vectors may be especially valuable for introducing GCREC to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999) J. Virol. 73:519-532 and Xu, H. et al. (1994) Dev. Biol. 163: 152-161, hereby incorporated by reference. The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another alternative, an alphavirus (positive, single-stranded RNA virus) vector is used to deliver polynucleotides encoding GCREC to target cells. The biology of the prototypic alphavirus, Semliki Forest Virus (SFV), has been studied extensively and gene transfer vectors have been based on the SFV genome (Garoff, H. and K.-J. Li (1998) Curr. Opin. Biotechnol. 9:464-469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for GCREC into the alphavirus genome in place of the capsid-coding region results in the production of a large number of GCREC-coding RNAs and the synthesis of high levels of GCREC in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74-83). The wide host range of alphaviruses will allow the introduction of GCREC into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163-177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding GCREC.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding GCREC. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

An additional embodiment of the invention encompasses a method for screening for a compound which is effective in altering expression of a polynucleotide encoding GCREC. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased GCREC expression or activity, a compound which specifically inhibits expression of the polynucleotide encoding GCREC may be therapeutically useful, and in the treament of disorders associated with decreased GCREC expression or activity, a compound which specifically promotes expression of the polynucleotide encoding GCREC may be therapeutically useful.

At least one, and up to a plurality, of test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding GCREC is exposed to at least one test compound thus obtained. The sample may comprise, for example, an intact or permeabilized cell, or an in vitro cell-free or reconstituted biochemical system. Alterations in the expression of a polynucleotide encoding GCREC are assayed by any method commonly known in the art. Typically, the expression of a specific nucleotide is detected by hybridization with a probe having a nucleotide sequence complementary to the sequence of the polynucleotide encoding GCREC. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a *Schizosaccharomyces pombe* gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8-13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nat. Biotechnol. 15:462-466.)

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, cellulose, gums, and proteins. Various formulations are commonly known and are thoroughly discussed in the latest edition of *Remington's Pharmaceutical Sciences* (Maack Publishing, Easton Pa.). Such compositions may consist of GCREC, antibodies to GCREC, and mimetics, agonists, antagonists, or inhibitors of GCREC.

The compositions utilized in this invention may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient. In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton. J. S. et al., U.S. Pat. No. 5,997,848). Pulmonary delivery has the advantage of administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising GCREC or fragments thereof. For example, liposome preparations containing a cell-impermeable macromolecule may promote cell fusion and intracellular delivery of the macromolecule. Alternatively, GCREC or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569-1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example GCREC or fragments thereof, antibodies of GCREC, and agonists, antagonists or inhibitors of GCREC, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind GCREC may be used for the diagnosis of disorders characterized by expression of GCREC, or in assays to monitor patients being treated with GCREC or agonists, antagonists, or inhibitors of GCREC. Antibodies useful for diagnostic purposes may be prepared in the same manner as described above for therapeutics. Diagnostic assays for GCREC include methods which utilize the antibody and a label to detect GCREC in human body fluids or in extracts of cells or tissues.

The antibodies may be used with or without modification, and may be labeled by covalent or non-covalent attachment of a reporter molecule. A wide variety of reporter molecules, several of which are described above, are known in the art and may be used.

A variety of protocols for measuring GCREC, including ELISAs, RIAs, and FACS, are known in the art and provide a basis for diagnosing altered or abnormal levels of GCREC expression. Normal or standard values for GCREC expression are established by combining body fluids or cell extracts taken from normal mammalian subjects, for example, human subjects, with antibodies to GCREC under conditions suitable for complex formation. The amount of standard complex formation may be quantitated by various methods, such as photometric means. Quantities of GCREC expressed in subject, control, and disease samples from biopsied tissues are compared with the standard values. Deviation between standard and subject values establishes the parameters for diagnosing disease.

In another embodiment of the invention, the polynucleotides encoding GCREC may be used for diagnostic purposes. The polynucleotides which may be used include oligonucleotide sequences, complementary RNA and DNA molecules, and PNAs. The polynucleotides may be used to detect and quantify gene expression in biopsied tissues in which expression of GCREC may be correlated with disease. The diagnostic assay may be used to determine absence, presence, and excess expression of GCREC, and to monitor regulation of GCREC levels during therapeutic intervention.

In one aspect, hybridization with PCR probes which are capable of detecting polynucleotide sequences, including genomic sequences, encoding GCREC or closely related molecules may be used to identify nucleic acid sequences which encode GCREC. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding GCREC, allelic variants, or related sequences.

Probes may also be used for the detection of related sequences, and may have at least 50% sequence identity to any of the GCREC encoding sequences. The hybridization probes of the subject invention may be DNA or RNA and may be derived from the sequence of SEQ ID NO:40-78 or from genomic sequences including promoters, enhancers, and introns of the GCREC gene.

Means for producing specific hybridization probes for DNAs encoding GCREC include the cloning of polynucleotide sequences encoding GCREC or GCREC derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding GCREC may be used for the diagnosis of disorders associated with expression of GCREC. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a cardiovascular disorder such as arteriovenous fistula, atherosclerosis, hypertension, vasculitis, Raynaud's disease, aneurysms, arterial dissections, varicose veins, thrombophlebitis and phlebothrombosis, vascular tumors, complications of thrombolysis, balloon angioplasty, vascular replacement, and coronary artery bypass graft surgery, congestive heart failure, ischemic heart disease, angina pectoris, myocardial infarction, hypertensive heart disease, degenerative valvular heart disease, calcific aortic valve stenosis, congenitally bicuspid aortic valve, mitral annular calcification, mitral valve prolapse, rheumatic fever and rheumatic heart disease, infective endocarditis, nonbacterial thrombotic endocarditis, endocarditis of systemic lupus erythematosus, carcinoid heart disease, cardiomyopathy, myocarditis, pericarditis, neoplastic heart disease, congenital heart disease, and complications of cardiac transplantation; a gastrointestinal disorder such as dysphagia, peptic esophagitis, esophageal spasm, esophageal stricture, esophageal carcinoma, dyspepsia, indigestion, gastritis, gastric carcinoma, anorexia, nausea, emesis, gastroparesis, antral or pyloric edema, abdominal angina, pyrosis, gastroenteritis, intestinal obstruction, infections of the intestinal tract, peptic ulcer, cholelithiasis, cholecystitis, cholestasis, pancreatitis, pancreatic carcinoma, biliary tract disease, hepatitis, hyperbilirubinemnia, cirrhosis, passive congestion of the liver, hepatoma, infectious colitis, ulcerative colitis, ulcerative proctitis, Crohn's disease, Whipple's disease, Mallory-Weiss syndrome, colonic carcinoma, colonic obstruction, irritable bowel syndrome, short bowel syndrome, diarrhea, constipation, gastrointestinal hemorrhage, acquired immunodeficiency syndrome (AIDS) enteropathy, jaundice, hepatic encephalopathy, hepatorenal syndrome, hepatic steatosis, hemochromatosis, Wilson's disease, alpha$_1$-antitrypsin deficiency, Reye's syndrome, primary sclerosing cholangitis, liver infarction, portal vein obstruction and thrombosis, centrilobular necrosis, peliosis hepatis, hepatic vein thrombosis, veno-occlusive disease, preeclampsia, eclampsia; acute fatty liver of pregnancy, intrahepatic cholestasis of pregnancy, and hepatic tumors including nodular hyperplasias, adenomas, and carcinomas; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a metabolic disorder such as diabetes, obesity, and osteoporosis; and an infection by a viral agent classified as adenovirus, arenavirus, bunyavirus, calicivirus, coronavirus, filovirus, hepadnavirus, herpesvirus, flavivirus, orthomyxovirus, parvovirus, papovavirus, paramyxovirus, picornavirus, poxvirus, reovirus, retrovirus, rhabdovirus, and togavirus. The polynucleotide sequences encoding GCREC may be used in Southern or northern analysis, dot blot, or other membrane-based technologies; in PCR technologies; in dipstick, pin, and multiformat ELISA-like assays; and in microarrays utilizing fluids or tissues from patients to detect altered GCREC expression. Such qualitative or quantitative methods are well known in the art.

In a particular aspect, the nucleotide sequences encoding GCREC may be useful in assays that detect the presence of associated disorders, particularly those mentioned above. The nucleotide sequences encoding GCREC may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of nucleotide sequences encoding GCREC in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of GCREC, a normal or standard profile for expression is established. This may be accomplished by combining body fluids or cell extracts taken from normal subjects, either animal or human, with a sequence, or a fragment thereof, encoding GCREC, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding GCREC may involve the use of PCR. These oligomers may be chemically synthesized, generated enzymatically, or produced in vitro. Oligomers will preferably contain a fragment of a polynucleotide encoding GCREC, or a fragment of a polynucleotide complementary to the polynucleotide encoding GCREC, and will be employed under optimized conditions for identification of a specific gene or condition. Oligomers may also be employed under less stringent conditions for detection or quantification of closely related DNA or RNA sequences.

In a particular aspect, oligonucleotide primers derived from the polynucleotide sequences encoding GCREC may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (fSSCP) methods. In SSCP, oligonucleotide primers derived from the polynucleotide sequences encoding GCREC are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

Methods which may also be used to quantify the expression of GCREC include radiolabeling or biotinylating nucleotides, coamplification of a control nucleic acid, and interpolating results from standard curves. (See, e.g., Melby, P. C. et al. (1993) J. Immunol. Methods 159:235-244; Duplaa, C. et al. (1993) Anal. Biochem. 212:229-236.) The speed of quantitation of multiple samples may be accelerated by running the assay in a high-throughput format where the oligomer or polynucleotide of interest is presented in various dilutions and a spectrophotometric or calorimetric response gives rapid quantitation.

In further embodiments, oligonucleotides or longer fragments derived from any of the polynucleotide sequences described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, GCREC, fragments of GCREC, or antibodies specific for GCREC may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time. (See Seilhamer et al., "Comparative Gene Transcript Analysis," U.S. Pat. No. 5,840,484, expressly incorporated by reference herein.) Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153-159; Steiner, S. and N. L. Anderson (2000) Toxicol. Lett. 112-113:467-471, expressly incorporated by reference herein). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity. (See, for example, Press Release 00-02 from the National Institute of Environmental Health Sciences, released Feb. 29, 2000, available at http://www.niehs.nlh.gov/oc/news/toxchip.htm.) Therefore, it is important and desirable in toxicological screening using toxicant signatures to include all expressed gene sequences.

In one embodiment, the toxicity of a test compound is assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another particular embodiment relates to the use of the polypeptide sequences of the present invention to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of the present invention. In some cases, further sequence data may be obtained for definitive protein identification.

A proteomic profile may also be generated using antibodies specific for GCREC to quantify the levels of GCREC expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103-111; Mendoze, L. G. et al. (1999) Biotechniques 27:778-788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533-537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art. (See, e.g., Brennan, T. M. et al. (1995) U.S. Pat. No. 5,474,796; Schena, M. et al. (1996) Proc. Natl. Acad. Sci. USA 93:10614-10619; Baldeschweiler et al. (1995) PCT application WO95/251116; Shalon, D. et al. (1995) PCT application WO95/35505; Heller, R. A. et al. (1997) Proc. Natl. Acad. Sci. USA 94:2150-2155; and Heller, M. J. et al. (1997) U.S. Pat. No. 5,605,662.) Various types of microarrays are well known and thoroughly described in *DNA Microarrays: A Practical Approach*, M. Schena, ed. (1999) Oxford University Press, London, hereby expressly incorporated by reference.

In another embodiment of the invention, nucleic acid sequences encoding GCREC may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multigene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345-355; Price, C. M. (1993) Blood Rev. 7:127-134; and Trask, B. J. (1991) Trends Genet. 7:149-154.) Once mapped, the nucleic acid sequences of the invention may be used to develop genetic linkage maps, for example, which correlate the inheritance of a disease state with the inheritance of a particular chromosome region or restriction fragment length polymorphism (RFLP). (See, for example, Lander, E. S. and D. Botstein (1986) Proc. Natl. Acad. Sci. USA 83:7353-7357.)

Fluorescent in situ hybridization (FISH) may be correlated with other physical and genetic map data. (See, e.g., Heinz-Ulrich, et al. (1995) in Meyers, supra, pp. 965-968.) Examples of genetic map data can be found in various scientific journals or at the Online Mendelian Inheritance in Man (OMIM) World Wide Web site. Correlation between the location of the gene encoding GCREC on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation. (See, e.g., Gatti, R. A. et al. (1988) Nature 336:577-580.) The nucleotide sequence of the instant invention may also be used to detect differences in the chromosomal location due to translocation, inversion, etc., among normal, carrier, or affected individuals.

In another embodiment of the invention, GCREC, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between GCREC and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with GCREC, or fragments thereof, and washed. Bound GCREC is then detected by methods well known in the art. Purified GCREC can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding GCREC specifically compete with a test compound for binding GCREC. In this manner, antibodies can be used to detect the presence of any peptide which shares one or more antigenic determinants with GCREC.

In additional embodiments, the nucleotide sequences which encode GCREC may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications and publications, mentioned above and below, in particular U.S. Ser. No. 60/172,852, U.S. Ser. No. 60/171,732, U.S. Ser. No. 60/176, 148, and U.S. Ser. No. 60/177,331, are expressly incorporated by reference herein.

EXAMPLES

I. Construction of cDNA Libraries

Incyte cDNAs were derived from cDNA libraries described in the LIFESEQ GOLD database (Incyte Genomics, Palo Alto Calif.) and shown in Table 4, column 5. The Incyte cDNA shown for SEQ ID NO:40 was derived from a cDNA library constructed from bone marrow tissue. The Incyte cDNAs shown for SEQ ID NO:41 were derived from cDNA libraries constructed from small intestine, including tissues associated with Crohn's disease, from large intestine, and from brain tissues. The Incyte cDNAs shown for SEQ ID NO:42 were derived from cDNA libraries constructed from prostate tumor, small intestine, breast, and epidermal tissues. The Incyte cDNAs shown for SEQ ID NO:43 were derived cDNA libraries constructed from soft tissue tumor, fetal rib, and brain tissue associated with Huntington's disease. The Incyte cDNAs shown for SEQ ID NO:57 were derived from cDNA libraries constructed from lymphocytes and mast cells, and from breast, uterine, prostate, adrenal gland, spinal cord, tibial muscle, lung, esophagus, small intestine, and colon tissues. The Incyte cDNAs shown for SEQ ID NO:58 were derived from cDNA libraries constructed from a fallopian tube tumor, uterine endometrium, and bronchial tissue. The Incyte cDNAs shown for SEQ ID NO:59 were derived from cDNA libraries constructed from colon tissues, including cecal tumor tissue, as well as from pancreatic tumor, pituitary gland, and brain tissues. The Incyte cDNAs shown for SEQ ID NO:60 were derived from cDNA libraries constructed from brain, including brain tumor tissue and tissues associated with Huntington's disease, and from prostate tumor, cervical adenocarcinoma, breast, small intestine, and bladder tissues. Some tissues were homogenized and lysed in guanidinium isothiocyanate, while others were homogenized and lysed in phenol or in a suitable mixture of denaturants, such as TRIZOL (Life Technologies), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+ RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY (A)PURE mRNA purification kit (Ambion, Austin Tex.).

In some cases, Stratagene was provided with RNA and constructed the corresponding cDNA libraries. Otherwise cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1-6.6.) Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), PCDNA2.1 plasmid (Invitrogen, Carlsbad Calif.), or pINCY (Incyte Genomics, Palo Alto Calif.). Recombinant plasmids were transformed into competent E. coli cells including XL1-Blue, XL1-BlueMRF, or SOLR from Stratagene or DH5α, DH10B, or ElectroMAX DH10B from Life Technologies.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Pharmacia Biotech or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Molecular Dynamics); the ABI PRISM 373 or 377 sequencing system (Applied Biosystems) in conjunction with standard ABI protocols and base calling software; or other sequence analysis systems known in the art. Reading frames within the cDNA sequences were identified using standard methods (reviewed in Ausubel, 1997, supra, unit 7.7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM, and hidden Markov model (HMM)-based protein family databases such as PFAM. (HMM is a probabilistic approach which analyzes consensus primary structures of gene families. See, for example, Eddy, S. R. (1996) Curr. Opin. Struct. Biol. 6:361-365.) The queries were performed using programs based on BLAST, FASTA, BLIMPS, and HMMR. The Incyte cDNA sequences were assembled to produce polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The polynucleotide sequences were translated to derive the corresponding polypeptide sequences which were subsequently analyzed by querying against databases such as the GenBank protein databases (genpept), SwissProt, BLOCKS, PRINTS, DOMO, PRODOM, Prosite, and hidden Markov model (HMM)-based protein family databases such as PFAM. Full length polynucleotide sequences are also analyzed using MACDNASIS PRO software (Hitachi Software Engineering, South San Francisco Calif.) and LASERGENE software (DNASTAR). Polynucleotide and polypeptide sequence alignments are generated using default parameters specified by the CLUSTAL algorithm as incorporated into the MEGALIGN multisequence alignment program (DNASTAR), which also calculates the percent identity between aligned sequences.

Table 7 summarizes the tools, programs, and algorithms used for the analysis and assembly of Incyte cDNA and assembled polynucleotide sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of polynucleotide and polypeptide sequences were also used to identify polynucleotide sequence fragments from SEQ ID NO:40-78. Fragments from about 20 to about 4000 nucleotides which are useful in hybridization and amplification technologies are described in Table 4, column 4.

IV. Identification and Editing of Coding Sequences from Genomic DNA

Putative G-protein coupled receptors were initially identified by running the Genscan gene identification program against public genomic sequence databases (e.g., gbpri and gbhtg). Genscan is a general-purpose gene identification program which analyzes genomic DNA sequences from a variety of organisms (See Burge, C. and S. Karlin (1997) J. Mol. Biol. 268:78-94, and Burge, C. and S. Karlin (1998) Curr. Opin. Struct. Biol. 8:346-354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode G-protein coupled receptors, the encoded polypeptides were analyzed by querying against PFAM models for G-protein coupled receptors (7tm_1, 7tm_2, 7tm_3, and 7tm_4). Potential G-protein coupled receptors were also identified by homology to Incyte cDNA sequences that had been annotated as G-protein coupled receptors. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Polynucleotide sequences, including SEQ ID NO:40, SEQ ID NO:41, SEQ ID NO:42, SEQ ID NO:43, SEQ ID NO:61, SEQ ID NO:62, and SEQ ID NO:63, were obtained by assembling Genscan-predicted coding sequences with Incyte cDNA sequences and/or public cDNA sequences using the assembly process described in Example III. Alternatively, polynucleotide sequences, including SEQ ID NO:44, SEQ ID NO:45, SEQ ID NO:46, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78, are full length coding regions derived entirely from edited or unedited Genscan-predicted coding sequences. Alternatively, polynucleotide sequences, including SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, and SEQ ID NO:56, are partial genes derived from the assembly and editing of Genscan-predicted sequences only.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of GCREC Encoding Polynucleotides

The sequences which were used to assemble SEQ ID NO:40-78 were compared with sequences from the Incyte LIFESEQ database and public domain databases using BLAST and other implementations of the Smith-Waterman algorithm. Sequences from these databases that matched SEQ ID NO:40-78 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Généthon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, or human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Généthon which provide boundaries for radiation hybrid markers whose sequences were included in each of the clusters. Human genome maps and other resources available to the public, such as the NCBI "GeneMap'99" World Wide Web site (http:/www.ncbi.nlm.nih.gov/genemap/), can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel (1995) supra, ch. 4 and 16.)

Analogous computer techniques applying BLAST were used to search for identical or related molecules in cDNA databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{BLAST \text{ Score} \times \text{Percent Identity}}{5 \times \text{minimum}\{\text{length}(Seq. \ 1), \text{length}(Seq. \ 2)\}}$$

The product score tales into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotide sequences encoding GCREC are analyzed with respect to the tissue sources from which they were derived. For example, some full length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding GCREC. cDNA sequences and cDNA library/tissue information are found in the LIFESEQ GOLD database (Incyte Genomics, Palo Alto Calif.).

VIII. Extension of GCREC Encoding Polynucleotides

Full length polynucleotide sequences were also produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, and individual colonies were picked and cultured overnight at 37° C. in 384-well plates in LB/2× carb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reampilfied using the same conditions as described above. Samples were diluted with 20% dimethysulfoxide (1:2, v/v), and sequenced using DYENAMIC energy transfer sequencing primers and the DYENAMIC DIRECT kit (Amersham Pharmacia Biotech) or the ABI PRISM BIG-DYE Terminator cycle sequencing ready reaction kit (Applied Biosystems).

In like manner, full length polynucleotide sequences are verified using the above procedure or are used to obtain 5' regulatory sequences using the above procedure along with oligonucleotides designed for such extension, and an appropriate genomic library.

IX. Labeling and Use of Individual Hybridization Probes

Hybridization probes derived from SEQ ID NO:40-78 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [$\gamma$-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba I, or Pvu II (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1× saline sodium citrate and 0.5% sodium dodecyl sulfate. Hybridization patterns are visualized using autoradiography or an alternative imaging means and compared.

X. Microarrays

The linkage or synthesis of array elements upon a microarray can be achieved utilizing photolithography, piezoelectric printing (ink-jet printing, See, e.g., Baldeschweiler, supra.), mechanical microspotting technologies, and derivatives thereof. The substrate in each of the aforementioned technologies should be uniform and solid with a non-porous surface (Schena (1999), supra). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements. (See, e.g., Schena, M. et al. (1995) Science 270:

467-470; Shalon, D. et al. (1996) Genome Res. 6:639-645; Marshall, A. and J. Hodgson (1998) Nat. Biotechnol. 16:27-31.)

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly(A)$^+$ RNA sample is reverse transcribed using MMLV reverse-transcriptase, 0.05 pg/µl oligo-(dT) primer (21mer), 1× first strand buffer, 0.03 units/µl RNase inhibitor, 500 µM dATP, 500 µM dGTP, 500 µM dTTP, 40 µM dCTP, 40 µM dCTP-Cy3 (BDS) or dCTP-Cy5 (Amersham Pharmacia Biotech). The reverse transcription reaction is performed in a 25 ml volume containing 200 ng poly(A)$^+$ RNA with GEMBRIGHT kits (Incyte). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (CLONTECH Laboratories, Inc. (CLONTECH), Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 µl 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1-2 ng to a final quantity greater than 5 µg. Amplified array elements are then purified using SEPHACRYL-400 (Amersham Pharmacia Biotech).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aminopropyl silane (Sigma) in 95% ethanol. Coated slides are cured in a 110° C. oven.

Array elements are applied to the coated glass substrate using a procedure described in U.S. Pat. No. 5,807,522, incorporated herein by reference. 1 µl of the array element DNA, at an average concentration of 100 ng/µl, is loaded into the open capillary printing element by a high-speed robotic apparatus. The apparatus then deposits about 5 nl of array element sample per slide.

Microarrays are UV-crosslinked using a STRATALINKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 µl of sample mixture consisting of 0.2 µg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 cm$^2$ coverslip. The arrays are transferred to a waterproof chamber having a cavity just slightly larger than a microscope slide. The chamber is kept at 100% humidity internally by the addition of 140 µl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte).

XI. Complementary Polynucleotides

Sequences complementary to the GCREC-encoding sequences, or any parts thereof, are used to detect, decrease, or inhibit expression of naturally occurring GCREC. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of GCREC. To inhibit transcription, a complementary oligonucleotide is designed from the most unique 5' sequence and used to prevent promoter binding to the coding sequence. To inhibit translation, a complementary oligonucleotide is designed to prevent ribosomal binding to the GCREC-encoding transcript.

XII. Expression of GCREC

Expression and purification of GCREC is achieved using bacterial or virus-based expression systems. For expression of GCREC in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express GCREC upon induction with isopropyl beta-D-thiogalactopyranoside (IPTG). Expression of GCREC in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding GCREC by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224-3227; Sandig, V. et al. (1996) Hum. Gene Ther. 7:1937-1945.)

In most expression systems, GCREC is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Pharmacia Biotech). Following purification, the GST moiety can be proteolytically cleaved from GCREC at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified GCREC obtained by these methods can be used directly in the assays shown in Examples XVI, XVII, and XVIII, where applicable.

XIII. Functional Assays

GCREC function is assessed by expressing the sequences encoding GCREC at physiologically elevated levels in mammalian cell culture systems. cDNA is subcloned into a mammalian expression vector containing a strong promoter that drives high levels of cDNA expression. Vectors of choice include PCMV SPORT (Life Technologies) and PCR3.1 (Invitrogen, Carlsbad Calif.), both of which contain the cytomegalovirus promoter. 5-10 μg of recombinant vector are transiently transfected into a human cell line, for example, an endothelial or hematopoietic cell line, using either liposome formulations or electroporation. 1-2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometry*, Oxford, New York N.Y.

The influence of GCREC on gene expression can be assessed using highly purified populations of cells transfected with sequences encoding GCREC and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding GCREC and other genes of interest can be analyzed by northern analysis or microarray techniques.

XIV. Production of GCREC Specific Antibodies

GCREC substantially purified using polyacrylamide gel electrophoresis (PAGE; see, e.g., Harrington, M. G. (1990) Methods Enzymol. 182:488-495), or other purification techniques, is used to immunize rabbits and to produce antibodies using standard protocols.

Alternatively, the GCREC amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for anti-peptide and anti-GCREC activity by, for example, binding the peptide or GCREC to a substrate, blocking with 1% BSA, reacting with rabbit antisera, washing, and reacting with radio-iodinated goat anti-rabbit IgG.

XV. Purification of Naturally Occurring GCREC Using Specific Antibodies

Naturally occurring or recombinant GCREC is substantially purified by immunoaffinity chromatography using antibodies specific for GCREC. An immunoaffinity column is constructed by covalently coupling anti-GCREC antibody to an activated chromatographic resin, such as CNBr-activated SEPHAROSE (Amersham Pharmacia Biotech). After the coupling, the resin is blocked and washed according to the manufacturer's instructions.

Media containing GCREC are passed over the immunoaffinity column, and the column is washed under conditions that allow the preferential absorbance of GCREC (e.g., high ionic strength buffers in the presence of detergent). The column is eluted under conditions that disrupt antibody/GCREC binding (e.g., a buffer of pH 2 to pH 3, or a high concentration of a chaotrope, such as urea or thiocyanate ion), and GCREC is collected.

XVI. Identification of Molecules which Interact with GCREC

Molecules which interact with GCREC may include agonists and antagonists, as well as molecules involved in signal transduction, such as G proteins. GCREC, or a fragment thereof, is labeled with $^{125}$I Bolton-Hunter reagent. (See, e.g., Bolton A. E. and W. M. Hunter (1973) Biochem. J. 133:529-539.) A fragment of GCREC includes, for example, a fragment comprising one or more of the three extracellular loops, the extracellular N-terminal region, or the third intracellular loop. Candidate molecules previously arrayed in the wells of a multi-well plate are incubated with the labeled GCREC, washed, and any wells with labeled GCREC complex are assayed. Data obtained using different concentrations of GCREC are used to calculate values for the number, affinity, and association of GCREC with the candidate ligand molecules.

Alternatively, molecules interacting with GCREC are analyzed using the yeast two-hybrid system as described in Fields, S. and O. Song (1989) Nature 340:245-246, or using commercially available kits based on the two-hybrid system, such as the MATCHMAKER system (Clontech). GCREC may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

Potential GCREC agonists or antagonists may be tested for activation or inhibition of GCREC receptor activity using the assays described in sections XVII and XVIII. Candidate molecules may be selected from known GPCR agonists or antagonists, peptide libraries, or combinatorial chemical libraries.

Methods for detecting interactions of GCREC with intracellular signal transduction molecules such as G proteins are based on the premise that internal segments or cytoplasmic domains from an orphan G protein-coupled seven transmembrane receptor may be exchanged with the analogous domains of a known G protein-coupled seven transmembrane receptor and used to identify the G-proteins and downstream signaling pathways activated by the orphan receptor domains (Kobilka, B. K. et al. (1988) Science 240:1310-1316). In an analogous fashion, domains of the orphan receptor may be cloned as a portion of a fusion protein and used in binding assays to demonstrate interactions with specific G proteins. Studies have shown that the third intracellular loop of G protein-coupled seven transmembrane receptors is important for G protein interaction and signal transduction (Conklin, B. R. et al. (1993) Cell 73:631-641). For example, the DNA fragment corresponding to the third intracellular loop of GCREC may be amplified by the polymerase chain reaction (PCR) and subcloned into a fusion vector such as pGEX (Pharmacia Biotech). The construct is transformed into saline. Bound G subunits are detected by [$^{32}$P]ADP-ribosylation with pertussis or cholera toxins. The reactions are terminated by the addition of SDS sample buffer (4.6% (w/v) SDS, 10% (v/v) β-mercaptoethanol, 20% (w/v) glycerol, 95.2 mM Tris-HCl, pH 6.8, 0.01% (w/v) bromphenol blue). The [$^{32}$P]ADP-labeled proteins are separated on 10% SDS-PAGE gels, and autoradiographed. These gels are transferred to nitrocellulose paper, blocked with blotto (5% nonfat dried milk, 50 mM Tris-HCl (pH 8.0), 2 mM $CaCl_2$, 80 mM NaCl, 0.02% $NaN_3$, and 0.2% Nonidet P-40) for 1 hour at room temperature, followed by incubation for 1.5 hours with Gα subtype selective antibodies (1:500; Calbiochem-Novabiochem). After three washes, blots are incubated with horseradish peroxidase (HRP)-conjugated goat anti-rabbit immunoglobulin (1:2000, Cappel, Westchester Pa.) and visualized by the chemiluminescence-based ECL method (Amersham Corp.).

XVII. Demonstration of GCREC Activity

An assay for GCREC activity measures the expression of GCREC on the cell surface, cDNA encoding GCREC is transfected into an appropriate mammalian cell line. Cell surface proteins are labeled with biotin as described (de la Fuente, M. A. et al. (1997) Blood 90:2398-2405). Immunoprecipitations are performed using GCREC-specific antibodies, and immunoprecipitated samples are analyzed using sodium dodecyl sulfate polyacrylamide gel electrophoresis (SDS-PAGE) and immunoblotting techniques. The ratio of labeled immunoprecipitant to unlabeled immunoprecipitant is proportional to the amount of GCREC expressed on the cell surface.

In the alternative, an assay for GCREC activity is based on a prototypical assay for ligand/receptor-mediated modulation of cell proliferation. This assay measures the rate of DNA synthesis in Swiss mouse 3T3 cells. A plasmid containing polynucleotides encoding GCREC is added to quiescent 3T3 cultured cells using transfection methods well known in the art. The transiently transfected cells are then incubated in the presence of [$^3$H]thymidine, a radioactive DNA precursor molecule. Varying amounts of GCREC ligand are then added to the cultured cells. Incorporation of [$^3$H]thymidine into acid-precipitable DNA is measured over an appropriate time interval using a radioisotope counter, and the amount incorporated is directly proportional to the amount of newly synthesized DNA A linear dose-response curve over at least a hundred-fold GCREC ligand concentration range is indicative of receptor activity. One unit of activity per milliliter is defined as the concentration of GCREC producing a 50% response level, where 100% represents maximal incorporation of [$^3$H]thymidine into acid-precipitable DNA (McKay, I. and I. Leigh, eds. (1993) *Growth Factors: A Practical Approach*, Oxford University Press, New York N.Y., p. 73.)

In a further alternative, the assay for GCREC activity is based upon the ability of GPCR family proteins to modulate G protein-activated second messenger signal transduction pathways (e.g., cAMP; Gaudin, P. et al., (1998) J. Biol. Chem. 273:4990-4996). A plasmid encoding GCREC is transfected into a mammalian cell line (e.g., Chinese hamster ovary (CHO) or human embryonic kidney (HEK-293) cell lines) using methods well-known in the art. Transfected cells are grown in 12-well trays in culture medium for 48 hours, then the culture medium is discarded, and the attached cells are gently washed with PBS. The cells are then incubated in culture medium with or without ligand for 30 minutes, then the medium is removed and cells lysed by treatment with 1 M perchloric acid. The cAMP levels in the lysate are measured by radioimmunoassay using methods well-known in the art. Changes in the levels of cAMP in the lysate from cells exposed to ligand compared to those without ligand are proportional to the amount of GCREC present in the transfected cells.

To measure changes in inositol phosphate levels, the cells are grown in 24-well plates containing $1 \times 10^5$ cells/well and incubated with inositol-free media and [$^3$H]myoinositol, 2 μCi/well, for 48 hr. The culture medium is removed, and the cells washed with buffer containing 10 mM LiCl followed by addition of ligand. The reaction is stopped by addition of perchloric acid. Inositol phosphates are extracted and separated on Dowex AG1-X8 (Bio-Rad) anion exchange resin, and the total labeled inositol phosphates counted by liquid scintillation. Changes in the levels of labeled inositol phosphate from cells exposed to ligand compared to those without ligand are proportional to the amount of GCREC present in the transfected cells.

XVIII. Identification of GCREC Ligands

GCREC is expressed in a eukaryotic cell line such as CHO (Chinese Hamster Ovary) or HEK (Human Embryonic Kidney) 293 which have a good history of GPCR expression and which contain a wide range of G-proteins allowing for functional coupling of the expressed GCREC to downstream effectors. The transformed cells are assayed for activation of the expressed receptors in the presence of candidate ligands. Activity is measured by changes in intracellular second messengers, such as cyclic AMP or $Ca^{2+}$. These may be measured directly using standard methods well known in the art, or by the use of reporter gene assays in which a luminescent protein (e.g. firefly luciferase or green fluorescent protein) is under the transcriptional control of a promoter responsive to the stimulation of protein kinase C by the activated receptor (Milligan, G. et al. (1996) Trends Pharmacol. Sci. 17:235-237). Assay technologies are available for both of these second messenger systems to allow high throughput readout in multi-well plate format, such as the adenylyl cyclase activation FlashPlate Assay (NEN Life Sciences Products), or fluorescent $Ca^{2+}$ indicators such as Fluo-4 AM (Molecular Probes) in combination with the FLIPR fluorimetric plate reading system (Molecular Devices). In cases where the physiologically relevant second messenger pathway is not known, GCREC may be coexpressed with the G-proteins $G_{\alpha 15/16}$ which have been demonstrated to couple to a wide range of G-proteins (Offermanns, S. and M. I. Simon (1995) J. Biol. Chem. 270:15175-15180), in order to funnel the signal transduction of the GCREC through a pathway involving phospholipase C and $Ca^{2+}$ mobilization. Alternatively, GCREC may be expressed in engineered yeast systems which lack endogenous GPCRs, thus providing the advantage of a null background for GCREC activation screening. These yeast systems substitute a human GPCR and Ga protein for the corresponding components of the endogenous yeast pheromone receptor pathway. Downstream signaling pathways are also modified so that the normal yeast response to the signal is converted to positive growth on selective media or to reporter gene expression (Broach, J. R. and J. Thorner (1996) Nature 384 (supp.):14-16). The receptors are screened against putative ligands including known GPCR ligands and other naturally occurring bioactive molecules. Biological extracts from tissues, biological fluids and cell supernatants are also screened.

Various modifications and variations of the described methods and systems of the invention will be apparent to those skilled in the art without departing from the scope and spirit of the invention. Although the invention has been described in connection with certain embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Incyte Project ID | Polypeptide SEQ ID NO: | Incyte Polypeptide ID | Polynucleotide SEQ ID NO: | Incyte Polynucleotide ID |
|---|---|---|---|---|
| 104941 | 1 | 104941CD1 | 40 | 104941CB1 |
| 1499408 | 2 | 1499408CD1 | 41 | 1499408CB1 |
| 3168839 | 3 | 3168839CD1 | 42 | 3168839CB1 |
| 3291235 | 4 | 3291235CD1 | 43 | 3291235CB1 |
| 7472001 | 5 | 7472001CD1 | 44 | 7472001CB1 |
| 7472003 | 6 | 7472003CD1 | 45 | 7472003CB1 |
| 7472004 | 7 | 7472004CD1 | 46 | 7472004CB1 |
| 7475687 | 8 | 7475687CP1 | 47 | 7475687CT1 |
| 7483029 | 9 | 7483029CP1 | 48 | 7483029CT1 |
| 7477933 | 10 | 7477933CP1 | 49 | 7477933CT1 |
| 7475164 | 11 | 7475164CP1 | 50 | 7475164CT1 |
| 7473909 | 12 | 7473909CP1 | 51 | 7473909CT1 |
| 7475252 | 13 | 7475252CP1 | 52 | 7475252CT1 |
| 7927572 | 14 | 7927572CP1 | 53 | 7927572CT1 |
| 7481257 | 15 | 7481257CP1 | 54 | 7481257CT1 |
| 7485790 | 16 | 7485790CP1 | 55 | 7485790CT1 |
| 7482993 | 17 | 7482993CP1 | 56 | 7482993CT1 |
| 2829053 | 18 | 2829053CD1 | 57 | 2829053CB1 |
| 3068234 | 19 | 3068234CD1 | 58 | 3068234CB1 |
| 5029478 | 20 | 5029478CD1 | 59 | 5029478CB1 |
| 5102576 | 21 | 5102576CD1 | 60 | 5102576CB1 |
| 2200534 | 22 | 2200534CD1 | 61 | 2200534CB1 |
| 3275821 | 23 | 3275821CD1 | 62 | 3275821CB1 |
| 3744167 | 24 | 3744167CD1 | 63 | 3744167CB1 |
| 7472007 | 25 | 7472007CD1 | 64 | 7472007CB1 |
| 7472008 | 26 | 7472008CD1 | 65 | 7472008CB1 |
| 7472013 | 27 | 7472013CD1 | 66 | 7472013CB1 |
| 7472015 | 28 | 7472015CD1 | 67 | 7472015CB1 |

TABLE 1-continued

| Incyte Project ID | Polypeptide SEQ ID NO: | Incyte Polypeptide ID | Polynucleotide SEQ ID NO: | Incyte Polynucleotide ID |
|---|---|---|---|---|
| 7472016 | 29 | 7472016CD1 | 68 | 7472016CB1 |
| 7472017 | 30 | 7472017CD1 | 69 | 7472017CB1 |
| 7472018 | 31 | 7472018CD1 | 70 | 7472018CB1 |
| 7472019 | 32 | 7472019CD1 | 71 | 7472019CB1 |
| 7472021 | 33 | 7472021CD1 | 72 | 7472021CB1 |
| 7472009 | 34 | 7472009CD1 | 73 | 7472009CB1 |
| 7472010 | 35 | 7472010CD1 | 74 | 7472010CB1 |
| 7472011 | 36 | 7472011CD1 | 75 | 7472011CB1 |
| 7472012 | 37 | 7472012CD1 | 76 | 7472012CB1 |
| 7472014 | 38 | 7472014CD1 | 77 | 7472014CB1 |
| 7472020 | 39 | 7472020CD1 | 78 | 7472020CB1 |

TABLE 2

| Polypeptide SEQ ID NO: | Incyte Polypeptide ID | GenBank ID NO: | Probability Score | GenBank Homolog |
|---|---|---|---|---|
| 1 | 104941CD1 | g7211316 | 6.9E−146 | Olfactory receptor [*Callithrix jacchus*] |
| 2 | 1499408CD1 | g202806 | 5.20E−162 | Vasopressin receptor [*Rattus norvegicus*] |
| 3 | 3168839CD1 | g3618229 | 2.2E−44 | G protein-linked P2Y4 receptor [*Rattus norvegicus*] |
| 4 | 3291235CD1 | g3287369 | 1.40E−126 | A-2 [*Mus musculus*] |
| 5 | 7472001CD1 | g1256393 | 2.20E−122 | Taste bud receptor protein TB 641 [*Rattus norvegicus*] |
| 6 | 7472003CD1 | g4378765 | 1.20E−169 | Orphan G protein-coupled receptor GPR54 [*Rattus norvegicus*] |
| 7 | 7472004CD1 | g1698952 | 6.30E−118 | High-affinity lysophosphatidic acid receptor [*Xenopus laevis*] |
| 8 | 7475687CP1 | g1256393 | 4.70E−90 | Taste bud receptor protein TB 641 [*Rattus norvegicus*] |
| 9 | 7483029CP1 | g2447219 | 2.50E−75 | OLF4 [*Homo sapiens*] |
| 10 | 7477933CP1 | g2792016 | 4.90E−79 | Olfactory receptor [*Homo sapiens*] |
| 11 | 7475164CP1 | g517366 | 3.00E−111 | Olfactory receptor [*Rattus norvegicus*] |
| 12 | 7473909CP1 | g4680264 | 1.90E−22 | Odorant receptor S25 [*Mus musculus*] |
| 13 | 7475252CP1 | g2447219 | 6.50E−61 | OLF4 [*Homo sapiens*] |
| 14 | 7927572CP1 | g8100089 | 6.7E−54 | Putative taste receptor HTR2 [*Homo sapiens*] |
| 15 | 7481257CP1 | g4826521 | 4.00E−29 | dJ88J8.1 (novel 7 transmembrane receptor (rhodopsin family) (olfactory receptor like protein (hs6M1-15)) [*Homo sapiens*] |
| 16 | 7485790CP1 | g2447219 | 3.00E−40 | OLF4 [*Homo sapiens*] |
| 17 | 7482993CP1 | g1314665 | 3.10E−54 | CfOLF3 [*Canis familiaris*] |
| 18 | 2829053CD1 | | | |
| 19 | 3068234CD1 | g5922725 | 3.1E−190 | Lysophosphatidic acid G protein-coupled receptor [*Homo sapiens*] |
| 20 | 5029478CD1 | g1049072 | 3.6E−21 | Galanin receptor GALR1 [*Rattus norvegicus*] (Cloning and characterization of the rat GALR1 galanin receptor from Rin14B insulinoma cells. Brain Res. Mol. Brain Res. 1995 Dec 28; 34(2): 179-189.) |
| 21 | 5102576CD1 | g2792016 | 2.4E−92 | Olfactory receptor [*Homo sapiens*] (Molecular cloning and chromosomal mapping of olfactory receptor genes expressed in the male germ line: evidence for their wide distribution in the human genome. Biochem. Biophys. Res. Commun. 1997 Aug 18; 237(2): 283-287.) |
| 22 | 2200534CD1 | g5051404 | 4.6e−131 | 573K1.15 (mm17M1-6) 7-transmembrane olfactory receptor-like protein (rhodopsin family) [*Mus musculus*] |
| 23 | 3275821CD1 | g182742 | 1.5e−29 | Formyl peptide receptor [*Homo sapiens*] (Murphy, P. M. et al. (1992) J. Biol. Chem. 267: 7637-7643) |
| 24 | 3744167CD1 | g9186902 | 1.2E−240 | Leukotriene B4 receptor, BLT2 [*Mus musculus*] |
| 25 | 7472007CD1 | g7638409 | 1.3E−199 | Olfactory receptor P2 [*Mus musculus*] |
| 26 | 7472008CD1 | g4218182 | 1.0e−89 | dJ271M21.2 (hs6M1-12 (7 transmembrane receptor (rhodopsin family) (olfactory receptor like) protein)) [*Homo sapiens*] |
| 27 | 7472013CD1 | g205846 | 2.5e−70 | Olfactory protein [*Rattus norvegicus*] |
| 28 | 7472015CD1 | g1204095 | 2.5e−25 | Dopamine receptor [*Fugu rubripes*] |
| 29 | 7472016CD1 | g6090796 | 1.1E−215 | Olfactory receptor [*Gorilla gorilla*] |
| 30 | 7472017CD1 | g3757727 | 2.0e−61 | dJ80I19.7 (olfactory receptor-like protein (hs6M1-3)) [*Homo sapiens*] |
| 31 | 7472018CD1 | g6644328 | 2.3E−112 | Orphan G protein-coupled receptor GPR26 [*Rattus norvegicus*] |
| 32 | 7472019CD1 | g5869916 | 2.7e−73 | Olfactory receptor [*Mus musculus*] |
| 33 | 7472021CD1 | g6090804 | 2.6e−94 | Olfactory receptor [*Gorilla gorilla*] |
| 34 | 7472009CD1 | g1016362 | 1.6e−68 | OL1 receptor [*Rattus norvegicus*] |
| 35 | 7472010CD1 | g2317704 | 7.3e−80 | Olfactory receptor [*Rattus norvegicus*] |
| 36 | 7472011CD1 | g6178008 | 4.9E−114 | Odorant receptor MOR18 [*Mus musculus*] |
| 37 | 7472012CD1 | g205816 | 6.8e−84 | Olfactory protein [*Rattus norvegicus*] |
| 38 | 7472014CD1 | g205816 | 3.9e−88 | Olfactory protein [*Rattus norvegicus*] |
| 39 | 7472020CD1 | g2792016 | 1.9e−97 | Olfactory receptor [*Homo sapiens*] |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 104941CD1 | 311 | S68 S189 S292 Y310 | N5 N66 | 7 transmembrane receptor (rhodopsin family): G42-Y291 GPCR signature: K91-P130, I208-Y219, Y283-K299, Y103-S151 Olfactory receptor signature: M60-K81, F178-D192, F239-G254, A275-L286, S292-Q306 Transmembrane domains: I31-I47, P211-I229 | MOTIFS HMMER-PFAM BLIMPS-BLOCKS BLIMPS-PRINTS ProfileScan HMMER |
| 2 | 1499408CD1 | 891 | T148 S686 S114 S248 S350 S481 S501 T628 T814 S856 T84 S140 T144 T325 T411 T543 S568 S676 T706 T788 Y372 | N378 | ATP/GTP binding site (P-loop): G202-T209 | MOTIFS |
| 3 | 3168839CD1 | 422 | T232 S178 T342 S363 S371 S397 T21 S211 S226 T307 S332 S367 | N4 N9 N251 N323 | 7 transmembrane receptor (rhodopsin family): L39-Y297 Rhodopsin-like GPCR superfamily: L24-L48, V57-R78, F101-I123, V137-R158, V192-F215, T232-V256, L279-R305 Transmembrane domains: V275-L295 | MOTIFS HMMER-PFAM BLIMPS-BLOCKS ProfileScan BLIMPS-PRINTS HMMER |
| 4 | 3291235CD1 | 609 | S228 S229 S396 S456 S324 S328 S364 S417 S466 T506 S568 S590 S153 S268 T392 S462 S482 S560 Y348 | | 7 transmembrane receptor (rhodopsin family): E80-E154 GPCR signatures: F76-P115, F395-A405, A442-E458, E509-P526 Transmembrane domain: V174-L199 | MOTIFS HMMER-PFAM BLIMPS-BLOCKS BLIMPS-PRINTS HMMER |
| 5 | 7472001CD1 | 313 | S68 T194 T200 S267 T309 T138 T164 T290 S306 | N5 N85 | 7 transmembrane receptor (rhodopsin family): G41-I259 GPCR signature: K91-P130, T281-K297, Y103-A147 Olfactory receptor signature: M60-R81, F178-D192, F239-V254, A273-L284, T290-L304 Signal peptide: M1-T38 Transmembrane domains: F30-T48, F63-M83 | MOTIFS HMMER-PFAM BLIMPS-BLOCKS BLIMPS-PRINTS ProfileScan HMMER SPScan HMMER |
| 6 | 7472003CD1 | 398 | S36 T155 | N10 N18 N28 | 7 transmembrane receptor (rhodopsin family): G59-Y323 GPCR signature: W108-P147, Y213-Y224, A256-F282, N315-R331, N119-I166 Neuropeptide Y receptor signature: R69-I81 L321-F334 Transmembrane domain: A42-Y65 | MOTIFS HMMER-PFAM BLIMPS-BLOCKS BLIMPS-PRINTS ProfileScan HMMER |
| 7 | 7472004CD1 | 369 | S228 T94 T218 S339 T350 | N12 | 7 transmembrane receptor (rhodopsin family): G48-Y321 Rhodopsin-like GPCR signature: T33-Y57, I66-F87, F111-I133, R144-V165, V193-L216, A262-V286, S303-H329 Transmembrane domains: T33-V51, M109-I125, Y189-M213, M256-V275 | MOTIFS HMMER-PFAM BLIMPS-BLOCKS BLIMPS-PRINTS HMMER |
| 8 | 7475687CP1 | 194 | T186 T76 T82 T46 T172 | | 7 transmembrane receptor (rhodopsin family): M1-Y171 Opsins retinal binding site: Y142-N194 Olfactory receptor signature: F60-D74, F121-V136, A155-L166, T172-T186 | MOTIFS HMMER-PFAM BLIMPS-BLOCKS BLIMPS-PRINTS ProfileScan |
| 9 | 7483029CP1 | 173 | T16 S34 T60 | N32 N167 | 7 transmembrane receptor (rhodopsin family): G8-C146 | MOTIFS HMMER-PFAM BLIMPS- |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Rhodopsin-like GPCR signature: M26-K47, F71-I93, L107-I128 | BLOCKS ProfileScan BLIMPS-PRINTS |
| | | | | | Signal peptide: M1-L22 | SPScan HMMER |
| | | | | | Transmembrane domains: M68-A86, M103-L121 | HMMER |
| 10 | 7477933CP1 | 220 | S172 | | 7 transmembrane receptor (rhodopsin family): P1-C192 | MOTIFS HMMER-PFAM BLIMPS-BLOCKS |
| | | | | | Olfactory receptor signature: M2-K23, F120-D134, F181-G196 | BLIMPS-PRINTS |
| | | | | | Rhodopsin-like GPCR signature: L47-I69, I142-V165 | |
| | | | | | Transmembrane domains: M44-A62, V85-T110 | HMMER |
| 11 | 7475164CP1 | 302 | T296 S58 S84 T107 T257 T9 T69 S128 T151 S282 | | 7 transmembrane receptor (rhodopsin family): G32-I193 | MOTIFS HMMER-PFAM BLIMPS-BLOCKS |
| | | | | | GPCR signature: N81-P120, I273-K289, S93-L142 | ProfileScan |
| | | | | | Olfactory receptor signature: V50-K71, Y168-S182, F229-G244, S265-L276, S282-T296 | BLIMPS-PRINTS |
| | | | | | Transmembrane domains: F19-L39, I188-I207 | HMMER |
| 12 | 7473909CP1 | 110 | S70 S36 T66 S94 | | GPCR signature: I85-K101 | MOTIFS BLIMPS-BLOCKS |
| | | | | | Olfactory receptor signature: F41-G56, A77-L88, S94-Y108 | BLIMPS-PRINTS |
| 13 | 7475252CP1 | 178 | S66 S151 S136 | N4 N64 | 7 transmembrane receptor (rhodopsin family): G40-L153 | MOTIFS HMMER-PFAM BLIMPS-BLOCKS |
| | | | | | Rhodopsin-like GPCR signature: V25-S49, M58-K79, L103-I125, S102-S151 | ProfileScan BLIMPS-PRINTS |
| | | | | | Transmembrane domains: L29-I45, M100-M117 | HMMER |
| 14 | 7927572CP1 | 92 | | | Olfactory receptor signature: F25-D39 | MOTIFS BLIMPS-PRINTS |
| 15 | 7481257CP1 | 97 | | | 7 transmembrane receptor (rhodopsin family): M1-Y96 | MOTIFS HMMER-PFAM BLIMPS-BLOCKS |
| | | | | | GPCR signature: V13-Y24, Q41-Q67 | BLIMPS-PRINTS |
| | | | | | Olfactory receptor signature: F44-G59, L80-L91 | |
| | | | | | Signal peptide: M1-G27 | SPScan HMMER |
| | | | | | Transmembrane domain: M8-Y24 | HMMER |
| 16 | 7485790CP1 | 133 | S74 | | 7 transmembrane receptor (rhodopsin family): R22-V128 | MOTIFS HMMER-PFAM BLIMPS-BLOCKS |
| | | | | | GPCR signature: G71-P110 | BLIMPS-PRINTS |
| | | | | | Transmembrane domain: M82-A100 | HMMER |
| 17 | 7482993CP1 | 213 | S85 S205 S159 T183 | N83 | 7 transmembrane receptor (rhodopsin family): S2-Y182 | MOTIFS HMMER-PFAM BLIMPS-BLOCKS |
| | | | | | GPCR signature: R127-R153, S2-A38 | ProfileScan |
| | | | | | Olfactory receptor signature: F69-N83, F130-G145, V166-L177, T183-G197 | BLIMPS-PRINTS |
| | | | | | Transmembrane domains: P102-I120, F130-V152 | HMMER |
| 18 | 2829053CD1 | 180 | S30 S41 S109 S125 S140 S35 S36 S149 | | Beta-1 adrenergic receptor signature: I148-S166 | MOTIFS BLIMPS-PRINTS |
| | | | | | Signal peptide: M1-S67 | SPScan |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 19 | 3068234CD1 | 353 | T146 T217 T233 S321 S17 T21 S294 S329 T141 S229 T303 Y14 | N15 N139 N172 N349 | 7 transmembrane receptor (rhodopsin family): S47-Y293 Rhodopsin-like GPCR superfamily signature: I32-I56, F65-L86, L109-I131, R144-L165, Y187-Y210, L237-L261, K275-Y301 | MOTIFS HMMER-PFAM BLIMPS-BLOCKS BLIMPS-PRINTS |
|  |  |  |  |  | Transmembrane domains: V36-I56, T146-G166, Y187-L207, T240-V258 | HMMER |
| 20 | 5029478CD1 | 361 | T242 S256 S237 S350 | N21 N322 | 7 transmembrane receptor (rhodopsin family): G57-Y321 Rhodopsin-like GPCR superfamily signature: V42-A66, T74-V95, M118-I140, A154-V175, D208-L231, L262-L286, F303-E329 | MOTIFS HMMER-PFAM BLIMPS-BLOCKS BLIMPS-PRINTS |
|  |  |  |  |  | Transmembrane domains: T45-V65, V124-Q144, V209-I233, L266-N291 | HMMER |
| 21 | 5102576CD1 | 251 | S119 S196 |  | 7 transmembrane receptor (rhodopsin family): R8-C251 GPCR signature: R57-P96 Olfactory receptor signature: M26-K47, L144-D158, F205-G220, A241-C252 | MOTIFS HMMER-PFAM BLIMPS-BLOCKS BLIMPS-PRINTS |
|  |  |  |  |  | Transmembrane domains: T66-D88, V109-T134 | HMMER |
| 22 | 2200534CD1 | 315 | S6 S136 T291 | N4 N154 | G-protein coupled receptor: DM00013(P232750)17-306: S17-L305 DM00013(A570690)15-304: F16-L305 DM00013(P47881)20-309: P20-L305 PD149621: T246-L305 PD000921: C168-L245 PD002495: N4-L47 BL00237: L89-P128, L207-Y218, T282-K298 Olfactory receptor PR00245: M58-P79, F176-G190, V238-G253, V274-L285, T291-L305 | HMMER BLIMPS-PRINTS BLIMPS-BLOCKS HMMER-PFAM MOTIFS |
|  |  |  |  |  | G-protein coupled receptors | BLAST-PRODOM BLAST-DOMO |
|  |  |  |  |  | Transmembrane domains: V204-M228, G40-Y290 | HMMER |
| 23 | 3275821CD1 | 470 | T3 T18 T326 T332 T340 S350 S424 S451 T459 S192 | N47 | G-protein coupled receptor: DM00013(P21462)20-317: V34-L306 PD000009: L68-F169 BL00237: W97-P136, G201-H212, A230-A256, N287-R303 GPCR profile: F109-V155 Rhodopsin GPCR family PR00237: W31-G55, L66-Q87, W111-A133, L147-V168, L193-Q216, F235-L259, L277-R303 | HMMER-PFAM BLIMPS-BLOCKS BLIMPS-PRINTS ProfileScan MOTIFS |
|  |  |  |  |  | G-protein coupled receptors | BLAST-PRODOM BLAST-DOMO |
|  |  |  |  |  | Transmembrane domains: T33-A51, L68-L259 | HMMER |
| 24 | 3744167CD1 | 358 | T291 S15 T18 S215 | N10 N38 N342 | G-protein coupled receptor: DM00013(P46092)27-318: S19-F290 DM00013(P31391)41-326: L29-L304 DM00013(P35414)22-324: W16-F290 BL00237: W87-P126, F190-Y201, R217-V243, S280-L296 GPCR profile: Y99-V145 Rhodopsin GPCR family PR00237: T22-A46, A57-F78, C101-V123, | HMMER-PFAM BLIMPS-BLOCKS BLIMPS-PRINTS ProfileScan MOTIFS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | L137-V158, L182-L205, V222-L246, R270-L296 | |
| | | | | | G-protein coupled receptors | BLAST-PRODOM |
| | | | | | | BLAST-DOMO |
| | | | | | Transmembrane domains: A138-Y159, G37-Y288 | HMMER |
| 25 | 7472007CD1 | 314 | S270 S291 S311 T49 S67 S193 | N4 N65 | Signal peptide: M1-Q56 | SPScan |
| | | | | | Transmembrane domains: L29-V48, L208-M228 | HMMER |
| | | | | | 7 transmembrane receptor (rhodopsin family) signature: G41-Y290 | HMMER-PFAM |
| | | | | | G-protein coupled receptor signatures: T90-P129, I207-Y218, T282-K298 | BLIMPS-BLOCKS |
| | | | | | G-protein coupled receptor signature: Y102-A147 | ProfileScan |
| | | | | | G-protein coupled receptor signature: A110-A125 | MOTIFS |
| | | | | | Olfactory receptor signatures: M59-K80, F177-D191, F238-S253, I274-L285, S291-I305 | BLIMPS-PRINTS |
| | | | | | Melanocortin receptor family: A5-L63 | BLIMPS-PRINTS |
| | | | | | Rhodopsin-like GPCR superfamily: L26-I50, M59-K80, F104-I126, F153-V174, A199-L222, A237-R261, K272-K298 | BLIMPS-PRINTS |
| | | | | | G-protein coupled receptor: DM00013\|P23270\|18-311: L23-H306 | BLAST-DOMO |
| | | | | | G-protein coupled receptor DM00013\|P23267\|20-309: L27-I305 | BLAST-DOMO |
| | | | | | G-protein coupled receptor DM00013\|P23275\|17-306: L23-I305 | BLAST-DOMO |
| | | | | | G-protein coupled receptor DM00013\|P30953\|18-306: L19-H306 | BLAST-DOMO |
| | | | | | Olfactory receptor PD000921: F168-L246 | BLAST-PRODOM |
| | | | | | Olfactory receptor PD149621: V247-R307 | BLAST-PRODOM |
| 26 | 7472008CD1 | 365 | S78 T192 S199 T320 S343 S47 S66 S78 S96 S217 T222 T337 T361 | N94 | Transmembrane domain: I226-L244 | HMMER |
| | | | | | 7 transmembrane receptor (rhodopsin family) signature: G70-Y319 | HMMER-PFAM |
| | | | | | G-protein coupled receptor signatures: K119-P158, L236-S247, K264-Q290, T311-H327 | BLIMPS-BLOCKS |
| | | | | | Olfactory receptor signatures: M88-Q109, V206-D220, F267-G282, L303-L314, T320-K334 | BLIMPS-PRINTS |
| | | | | | Melanocortin receptor family: V73-L84, K80-L92 | BLIMPS-PRINTS |
| | | | | | Rhodopsin-like GPCR superfamily: L55-L79, M88-Q109, F133-V155, M228-A251, A266-Q290, K301-H327 | BLIMPS-PRINTS |
| | | | | | Olfactory receptor PD000921: L195-L275 | BLAST-PRODOM |
| | | | | | Olfactory receptor PD149621: V276-K331 | BLAST-PRODOM |
| | | | | | G-protein coupled receptor: DM00013\|P30955\|18-305: L61-L326 | BLAST-DOMO |
| | | | | | G-protein coupled receptor: DM00013\|P23269\|15-304: L61-L326 | BLAST-DOMO |
| | | | | | G-protein coupled receptor DM00013\|A57069\|15-304: D59-L326 | BLAST-DOMO |
| | | | | | G-protein coupled receptor DM00013\|P23275\|17-306: T67-L326 | BLAST-DOMO |
| 27 | 7472013CD1 | 317 | S68 S193 | N6 N22 N43 | Signal peptide: M1-G42 | SPScan |
| | | | | | Transmembrane domain: I23-L41 | HMMER |
| | | | | | 7 transmembrane receptor (rhodopsin family) signatures: | HMMER-PFAM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | G42-L155, A279-Y295 G-protein coupled receptor signatures: P91-P130, M212-Y223, T287-K303 | BLIMPS-BLOCKS |
| | | | | | G-protein coupled receptor signature: F103-L148 | ProfileScan |
| | | | | | G-protein coupled receptor signature: T111-A126 | MOTIFS |
| | | | | | Olfactory receptor signatures: M60-Q81, F182-D196, V243-G258, A279-A290, S296-L310 | BLIMPS-PRINTS |
| | | | | | Melanocortin receptor family: W52-L64 | BLIMPS-PRINTS |
| | | | | | Rhodopsin-like GPCR superfamily: L27-S51, M60-Q81, F105-I127, R141-G162, I204-G227, A242-Q266, M277-K303 | BLIMPS-PRINTS |
| | | | | | GPR3 orphan receptor signature: V161-N178 | BLIMPS-PRINTS |
| | | | | | G-protein coupled receptor: DM00013|P23274|18-306: L27-L310 | BLAST-DOMO |
| | | | | | G-protein coupled receptor: DM00013|P23272|18-306: Y25-L310 | BLAST-DOMO |
| | | | | | G-protein coupled receptor: DM00013|P30953|18-306: L27-L310 | BLAST-DOMO |
| | | | | | G-protein coupled receptor: DM00013|P30955|18-305: L27-L310 | BLAST-DOMO |
| | | | | | Olfactory receptor PD000921: G174-L250 | BLAST-PRODOM |
| | | | | | Olfactory receptor PD149621: T251-L310 | BLAST-PRODOM |
| 28 | 7472015CD1 | 335 | T73 S79 S214 S309 T217 S329 S331 | | Signal peptide: M1-A20 | HMMER |
| | | | | | Signal peptide: M1-A20 | SPScan |
| | | | | | Transmembrane domains: F5-V27, L45-T63, M117-I136 | HMMER |
| | | | | | 7 transmembrane receptor (rhodopsin family) signatures: T21-Y279 | HMMER-PFAM |
| | | | | | G-protein coupled receptor signatures: R71-P110, F174-Y185, P218-T244, N271-R287 | BLIMPS-BLOCKS |
| | | | | | G-protein coupled receptor signature: F84-L129 | ProfileScan |
| | | | | | G-protein coupled receptor signature: A91-I106 | MOTIFS |
| | | | | | Rhodopsin-like GPCR superfamily: S6-L30, S40-L61, V85-I107, V121-G142, V166-L189, A223-V247, E261-R287 | BLIMPS-PRINTS |
| | | | | | G-protein coupled receptor: DM00013|P41596|137-461: G8-D220 | BLAST-DOMO |
| | | | | | G-protein coupled receptor: DM00013|P47800|29-338: G8-Y281 | BLAST-DOMO |
| | | | | | G-protein coupled receptor: DM00013|P31388|20-336: G8-P218 | BLAST-DOMO |
| | | | | | G-protein coupled receptor: DM00013|JN0591|20-336: G8-P218 | BLAST-DOMO |
| 29 | 7472016CD1 | 309 | S8 S67 S188 S266 S137 S229 S266 S289 | N5 N65 N264 | Signal peptide: M1-L55 | SPScan |
| | | | | | Transmembrane domains: Y28-A48, M199-I218 | HMMER |
| | | | | | 7 transmembrane receptor (rhodopsin family) signatures: G41-Y288 | HMMER-PFAM |
| | | | | | G-protein coupled receptor signatures: K90-P129, F206-Y217, L234-R260, T280-K296 | BLIMPS-BLOCKS |
| | | | | | G-protein coupled receptor signature: Y102-A146 | ProfileScan |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Olfactory receptor signatures: M59-K80, F177-D191, F237-G252, I272-L283, S289-F303 | BLIMPS-PRINTS |
| | | | | | Rhodopsin-like GPCR superfamily: F26-C50, M59-K80, M104-I126 S140-L161, M198-F219, A270-K296 | BLIMPS-PRINTS |
| | | | | | G-protein coupled receptor: DM00013\|P23266\|17-306: Q20-L302 | BLAST-DOMO |
| | | | | | G-protein coupled receptor: DM00013\|P23274\|18-306: E22-L299 | BLAST-DOMO |
| | | | | | G-protein coupled receptor: DM00013\|P23269\|15-304: Q21-L299 | BLAST-DOMO |
| | | | | | G-protein coupled receptor: DM00013\|P30955\|18-305: E22-L302 | BLAST-DOMO |
| | | | | | Olfactory receptor PD149621: T245-S309 | BLAST-PRODOM |
| | | | | | Olfactory receptor PD000921: L166-L244 | BLAST-PRODOM |
| 30 | 7472017CD1 | 236 | S7 T217 | N5 N189 | Signal peptide: M1-G42 | SPScan |
| | | | | | Transmembrane domains: C31-M52, V123-L141 | HMMER |
| | | | | | 7 transmembrane receptor (rhodopsin family) signatures: F12-Y216 | HMMER-PFAM |
| | | | | | G-protein coupled receptor signatures: K24-P63, L133-Y144, C161-Q187, T208-K224 | BLIMPS-BLOCKS |
| | | | | | G-protein coupled receptor signature: Y36-V81 | ProfileScan |
| | | | | | G-protein coupled receptor signature: T44-A59 | MOTIFS |
| | | | | | Olfactory receptor signatures: L164-G179, I200-L211, T217-N231 | BLIMPS-PRINTS |
| | | | | | Rhodopsin-like GPCR superfamily: S38-V60, L125-A148, G163-Q187, K198-K224 | BLIMPS-PRINTS |
| | | | | | Olfactory receptor PD149621: V173-T236 | BLAST-PRODOM |
| | | | | | Olfactory receptor PD000921: C103-I172 | BLAST-PRODOM |
| | | | | | G-protein coupled receptor: DM00013\|P23269\|15-304: L15-L227 | BLAST-DOMO |
| | | | | | G-protein coupled receptor: DM00013\|P30953\|18-306: L15-L227 | BLAST-DOMO |
| | | | | | G-protein coupled receptor: DM00013\|A57069\|15-304: L15-R228 | BLAST-DOMO |
| | | | | | G-protein coupled receptor: DM00013\|P23275\|17-306: M1-L227 | BLAST-DOMO |
| 31 | 7472018CD1 | 363 | Y294 S321 S325 T353 S157 T210 S223 T240 T316 T340 | N47 N348 N355 | Signal peptide: M1-A24 | HMMER |
| | | | | | Signal peptide: M1-A24 | SPScan |
| | | | | | 7 transmembrane receptor (rhodopsin family) signatures: S22-Y294 | HMMER-PFAM |
| | | | | | G-protein coupled receptor signatures: T72-P111, F181-S192, R234-T260, K286-R302 | BLIMPS-BLOCKS |
| | | | | | Rhodopsin-like GPCR superfamily: L7-A31, S41-F62, D86-V108, Y122-G143, T173-H196, A239-A263, G276-R302 | BLIMPS-PRINTS |
| | | | | | P2Y4 purinoceptor signatures: Y32-L48, P111-L126 | BLIMPS-PRINTS |
| | | | | | G-protein coupled receptor: DM00013\|JN0591\|20-336: P3-L305 | BLAST-DOMO |
| | | | | | G-protein coupled receptor: DM00013\|P53452\|17-344: L7-F268 | BLAST-DOMO |
| | | | | | G-protein coupled receptor: DM00013\|P50406\|20-335: G4-L305 | BLAST-DOMO |
| | | | | | G-protein coupled receptor: DM00013\|P31388\|20-336: P3-L305 | BLAST-DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 32 | 7472019CD1 | 308 | S162 S290 S67 T187 S192 S265 | N5 N65 | Transmembrane domains: L30-I49, M197-L215 | HMMER |
|  |  |  |  |  | 7 transmembrane receptor (rhodopsin family) signatures: G41-Y289 | HMMER-PFAM |
|  |  |  |  |  | G-protein coupled receptor signatures: P90-P129, L206-Y217, L234-K260, T281-K297 | BLIMPS-BLOCKS |
|  |  |  |  |  | G-protein coupled receptor signature: S102-T147 | ProfileScan |
|  |  |  |  |  | Olfactory receptor signatures: I59-Q80, F176-D190, F237-G252, I273-L284, S290-M304 | BLIMPS-PRINTS |
|  |  |  |  |  | Melanocortin receptor family: F51-L63 | BLIMPS-PRINTS |
|  |  |  |  |  | Rhodopsin-like GPCR superfamily: T26-H50, I59-Q80, S104-I126, V140-L161, I198-A221, K271-K297 | BLIMPS-PRINTS |
|  |  |  |  |  | G-protein coupled receptor: DM00013\|P23275\|17-306: I17-M304 | BLAST-DOMO |
|  |  |  |  |  | G-protein coupled receptor: DM00013\|P23269\|15-304: F27-M304 | BLAST-DOMO |
|  |  |  |  |  | G-protein coupled receptor: DM00013\|P23266\|17-306: I17-M304 | BLAST-DOMO |
|  |  |  |  |  | G-protein coupled receptor: DM00013\|S29707\|18-306: P21-I300 | BLAST-DOMO |
|  |  |  |  |  | Olfactory receptor PD000921: L165-L244 | BLAST-PRODOM |
|  |  |  |  |  | Olfactory receptor PD149621: T245-M304 | BLAST-PRODOM |
| 33 | 7472021CD1 | 343 | S87 T154 S288 S326 S311 S316 | N25 N183 N314 | Transmembrane domains: Y55-L75, I214-I234 | HMMER |
|  |  |  |  |  | 7 transmembrane receptor (rhodopsin family) signatures: G61-Y310 | HMMER-PFAM |
|  |  |  |  |  | G-protein coupled receptor signatures: S38-L64, G110-P149, P302-K318 | BLIMPS-BLOCKS |
|  |  |  |  |  | G-protein coupled receptor signature: F122-V168 | ProfileScan |
|  |  |  |  |  | G-protein coupled receptor signature: S130-A145 | MOTIFS |
|  |  |  |  |  | Olfactory receptor signatures: M79-Q100, F197-Y211, F258-S273, F297-L305, S311-L325 | BLIMPS-PRINTS |
|  |  |  |  |  | Melanocortin receptor family: V71-L83 | BLIMPS-PRINTS |
|  |  |  |  |  | Vasopressin receptor signature: L75-L86 | BLIMPS-PRINTS |
|  |  |  |  |  | Olfactory receptor PD000921: I186-L265 | BLAST-PRODOM |
|  |  |  |  |  | Olfactory receptor PD149621: V267-E328 | BLAST-PRODOM |
|  |  |  |  |  | G-protein coupled receptor: DM00013\|P23269\|15-304: E40-L325 | BLAST-DOMO |
|  |  |  |  |  | G-protein coupled receptor: DM00013\|P23275\|17-306: S38-L325 | BLAST-DOMO |
|  |  |  |  |  | G-protein coupled receptor: DM00013\|P23273\|18-306: I45-L325 | BLAST-DOMO |
|  |  |  |  |  | G-protein coupled receptor: DM00013\|P23266\|17-306: S38-S326 | BLAST-DOMO |
| 34 | 7472009CD1 | 323 | S87 S232 T290 S8 S67 T193 | N5 | Transmembrane domains: L30-L47, I201-L221 | HMMER |
|  |  |  |  |  | 7 transmembrane receptor (rhodopsin family) signatures: G41-Y289 | HMMER-PFAM |
|  |  |  |  |  | G-protein coupled receptor signatures: K90-P129, L206-Y217, R234-R260, T281-A297 | BLIMPS-BLOCKS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | G-protein coupled receptor signature: F102-M147 | ProfileScan |
| | | | | | G-protein coupled receptor signature: A110-A125 | MOTIFS |
| | | | | | Olfactory receptor signatures: M59-K80, F177-D191, F237-G252, G273-L284, T290-L304 | BLIMPS-PRINTS |
| | | | | | Rhodopsin-like GPCR superfamily: F26-C50, Y104-I126, V140-A161, T198-L221, K271-A297 | BLIMPS-PRINTS |
| | | | | | Melanocortin receptor family: I51-L63, I126-N137 | BLIMPS-PRINTS |
| | | | | | Vasopressin receptor signature: L55-L66 | BLIMPS-PRINTS |
| | | | | | G-protein coupled receptor: DM00013\|P23275\|17-306: L25-L304 | BLAST-DOMO |
| | | | | | G-protein coupled receptor: DM00013\|A57069\|15-304: L27-L304 | BLAST-DOMO |
| | | | | | G-protein coupled receptor: DM00013\|P23270\|18-311: L25-L304 | BLAST-DOMO |
| | | | | | G-protein coupled receptor: DM00013\|P23266\|17-306: L27-L304 | BLAST-DOMO |
| | | | | | Olfactory receptor PD149621: T245-T310 | BLAST-PRODOM |
| | | | | | Olfactory receptor PD000921: F168-L244 | BLAST-PRODOM |
| 35 | 7472010CD1 | 299 | T68 S126 S280 T293 S10 S57 T156 | N55 | Transmembrane domain: L186-I205 | HMMER |
| | | | | | 7 transmembrane receptor (rhodopsin family) signatures: G31-Y279 | HMMER-PFAM |
| | | | | | G-protein coupled receptor signatures: S79-P118, F188-S199, S224-T250, V271-K287 | BLIMPS-BLOCKS |
| | | | | | G-protein coupled receptor signature: F91-F135 | ProfileScan |
| | | | | | G-protein coupled receptor signature: S99-A114 | MOTIFS |
| | | | | | Olfactory receptor signatures: M49-K70, Y166-S180. F227-G242, A263-L274, S280-L294 | BLIMPS-PRINTS |
| | | | | | Melanocortin receptor family: I41-L53 | BLIMPS-PRINTS |
| | | | | | Rhodopsin-like GPCR superfamily: Q16-G40, M49-K70, F93-I115, T181-V204, A226-T250, R261-K287 | BLIMPS-PRINTS |
| | | | | | G-protein coupled receptor: DM00013\|S29709\|11-299: G23-L294 | BLAST-DOMO |
| | | | | | G-protein coupled receptor: DM00013\|S51356\|18-307: I24-K292 | BLAST-DOMO |
| | | | | | G-protein coupled receptor: DM00013\|P23274\|18-306: I24-L294 | BLAST-DOMO |
| | | | | | G-protein coupled receptor: DM00013\|P30955\|18-305: I24-L294 | BLAST-DOMO |
| | | | | | Olfactory receptor PD149621: V237-R296 | BLAST-PRODOM |
| | | | | | Olfactory receptor PD000921: L155-I235 | BLAST-PRODOM |
| 36 | 7472011CD1 | 307 | S87 T288 S193 | N5 | Transmembrane domains: L23-I43, M98-M118, G204-H228 | HMMER |
| | | | | | 7 transmembrane receptor (rhodopsin family) signatures: G41-Y287 | HMMER-PFAM |
| | | | | | G-protein coupled receptor signatures: K90-P129, R234-R260, T279-Q295 | BLIMPS-BLOCKS |
| | | | | | G-protein coupled receptor signature: F102-T148 | ProfileScan |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Olfactory receptor signatures: M59-K80, F177-D191, A237-V252, V271-L282, T288-G302 | BLIMPS-PRINTS |
| | | | | | Melanocortin receptor family: S51-L63 | BLIMPS-PRINTS |
| | | | | | Rhodopsin-like GPCR superfamily: F26-T50, M59-K80, F104-I126, L140-A161, K199-L222, A236-R260, K269-Q295 | BLIMPS-PRINTS |
| | | | | | Olfactory receptor PD000921: L166-I245 | BLAST-PRODOM |
| | | | | | Olfactory receptor PD149621: V246-R303 | BLAST-PRODOM |
| | | | | | G-protein coupled receptor: DM00013\|S29710\|15-301: L17-L301 | BLAST-DOMO |
| | | | | | G-protein coupled receptor: DM00013\|P23275\|17-306: L17-L301 | BLAST-DOMO |
| | | | | | G-protein coupled receptor: DM00013\|P23266\|17-306: L17-L301 | BLAST-DOMO |
| | | | | | G-protein coupled receptor: DM00013\|P47881\|20-309: L23-L301 | BLAST-DOMO |
| 37 | 7472012CD1 | 314 | T19 S230 S291 | N5 N38 | 7 transmembrane receptor (rhodopsin family) signatures: G41-Y290 | HMMER-PFAM |
| | | | | | G-protein coupled receptor signatures: K90-P129. T282-K298 | BLIMPS-BLOCKS |
| | | | | | G-protein coupled receptor signature: Y102-M147 | ProfileScan |
| | | | | | G-protein coupled receptor signature: M110-A125 | MOTIFS |
| | | | | | Olfactory receptor signatures: M59-K80, F177-S191, F238-G253, I274-L285, S291-M305 | BLIMPS-PRINTS |
| | | | | | Rhodopsin-like GPCR superfamily: P26-L50, M59-K80, F104-I126, I199-I222, T237-R261, R272-K298 | BLIMPS-PRINTS |
| | | | | | G-protein coupled receptor: DM00013\|P23266\|17-306: I17-K303 | BLAST-DOMO |
| | | | | | G-protein coupled receptor: DM00013\|P23274\|18-306: E22-K303 | BLAST-DOMO |
| | | | | | G-protein coupled receptor: DM00013\|S29707\|18-306: P21-G299 | BLAST-DOMO |
| | | | | | G-protein coupled receptor: DM00013\|P30955\|18-305: P21-K303 | BLAST-DOMO |
| | | | | | Olfactory receptor PD149621: T246-T310 | BLAST-PRODOM |
| | | | | | Olfactory receptor PD000921: L166-L245 | BLAST-PRODOM |
| 38 | 7472014CD1 | 310 | S19 S67 S93 T267 S18 S137 S290 | N5 N265 | Transmembrane domains: V30-I46, M59-I78 | HMMER |
| | | | | | 7 transmembrane receptor (rhodopsin family) signatures: G41-Y289 | HMMER-PFAM |
| | | | | | G-protein coupled receptor signatures: K90-P129, I207-Y218, R235-Q261, T281-K297 | BLIMPS-BLOCKS |
| | | | | | G-protein coupled receptor signature: Y102-I151 | ProfileScan |
| | | | | | G-protein coupled receptor signature: T110-A125 | MOTIFS |
| | | | | | Olfactory receptor signatures: M59-K80, F177-S191, F238-G253, A273-L284, S290-M304 | BLIMPS-PRINTS |
| | | | | | Melanocortin receptor family: S51-L63 | BLIMPS-PRINTS |
| | | | | | Rhodopsin-like GPCR superfamily: P26-R50, M59-K80, F104-I126, V199-L222, Q271-K297 | BLIMPS-PRINTS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Olfactory receptor PD000921: L166-L245 | BLAST-PRODOM |
| | | | | | Olfactory receptor PD149621: T246-R306 | BLAST-PRODOM |
| | | | | | G-protein coupled receptor: DM00013\|P23266\|17-306: L17-M304 | BLAST-DOMO |
| | | | | | G-protein coupled receptor: DM00013\|P23274\|18-306: E22-M304 | BLAST-DOMO |
| | | | | | G-protein coupled receptor: DM00013\|P30955\|18-305: D23-M304 | BLAST-DOMO |
| | | | | | G-protein coupled receptor: DM00013\|P30953\|18-306: R20-H305 | BLAST-DOMO |
| 39 | 7472020CD1 | 359 | S257 S317 S178 S255 | N31 | Transmembrane domains: M127-A145, V168-T193 | HMMER |
| | | | | | 7 transmembrane receptor (rhodopsin family) signatures: R67-Y316 | HMMER-PFAM |
| | | | | | G-protein coupled receptor signatures: R116-P155, G233-Y244, S261-T287, T308-Q324 | BLIMPS-BLOCKS |
| | | | | | G-protein coupled receptor signature: F129-V173 | ProfileScan |
| | | | | | Olfactory receptor signatures: M85-K106, F203-D217, F264-G279, A300-L311, S317-R331 | BLIMPS-PRINTS |
| | | | | | GPR orphan receptor signature: S317-W328 | BLIMPS-PRINTS |
| | | | | | Cannabinoid receptor signatures: M60-L73, Y316-A326 | BLIMPS-PRINTS |
| | | | | | G-protein coupled receptor: DM00013\|P23265\|17-306: E45-L327 | BLAST-DOMO |
| | | | | | G-protein coupled receptor: DM00013\|P23268\|18-307: S44-L330 | BLAST-DOMO |
| | | | | | G-protein coupled receptor: DM00013\|S29707\|18-306: P47-L327 | BLAST-DOMO |
| | | | | | G-protein coupled receptor: DM00013\|P30953\|18-306: P47-L330 | BLAST-DOMO |
| | | | | | Olfactory receptor PD000921: N197-L271 | BLAST-PRODOM |
| | | | | | Olfactory receptor PD149621: V273-R333 | BLAST-PRODOM |

TABLE 4

| Polynucleotide SEQ ID NO: | Incyte Polynucleotide ID | Sequence Length | Selected Fragments | Sequence Fragments | 5' Position | 3' Position |
|---|---|---|---|---|---|---|
| 40 | 104941CB1 | 936 | | g4190944.v113.gs_10.edit | 1 | 936 |
| | | | | 104941H1 (BMARNOT02) | 208 | 429 |
| 41 | 1499408CB1 | 3365 | | g2335202.v113.gs_4.edit | 1 | 2105 |
| | | | | 1499408H1 (SINTBST01) | 1068 | 1325 |
| | | | | 927003X11 (BRAINOT04) | 1092 | 1764 |
| | | | | 1632960F6 (COLNNOT19) | 1613 | 2099 |
| | | | | 4051362F6 (SINTNOT18) | 1994 | 2618 |
| | | | | 1426416F6 (SINTBST01) | 2223 | 2686 |
| | | | | 2925035F6 (SININOT04) | 2535 | 3043 |
| | | | | 927003T6 (BRAINOT04) | 2710 | 3365 |
| 42 | 3168839CB1 | 1325 | | 3356166H1 (PROSTUT16) | 1 | 281 |
| | | | | g4589937.v113.gs_7.edit | 42 | 1188 |
| | | | | 3700658H1 (SININOT05) | 160 | 463 |
| | | | | 3168839H1 (BRSTNOT18) | 809 | 1059 |
| | | | | 4555080H1 (KERAUNT01) | 1084 | 1325 |
| 43 | 3291235CB1 | 2124 | | 3291235X308F1 (BONRFET01) | 1 | 413 |
| | | | | g5578925.v113.gs_2.edit | 295 | 2124 |
| | | | | 4720927F6 (BRAIHCT02) | 315 | 810 |
| | | | | 3291235F6 (BONRFET01) | 408 | 1004 |
| | | | | 3370971H1 (CONNTUT05) | 955 | 1208 |
| | | | | 1729983H1 (BRSTTUT08) | 1073 | 1293 |

TABLE 4-continued

| Polynucleotide SEQ ID NO: | Incyte Polynucleotide ID | Sequence Length | Selected Fragments | Sequence Fragments | 5' Position | 3' Position |
|---|---|---|---|---|---|---|
| 44 | 7472001CB1 | 942 | | g2121229.v113.gs__4.2.edit | 1 | 942 |
| 45 | 7472003CB1 | 1197 | | g3386590.v113.gs__1.edit | 1 | 1197 |
| 46 | 7472004CB1 | 1110 | | g4741473.v113.gs__5.edit | 1 | 1110 |
| 47 | 7475687CT1 | 582 | | g2121229.v113.gs4.1.nt.edit | 1 | 582 |
| 48 | 7483029CT1 | 519 | | g2447218.v113.gs2.nt.edit | 1 | 519 |
| 49 | 7477933CT1 | 663 | | g2673897.v113.gs7.nt.edit | 1 | 663 |
| 50 | 7475164CT1 | 911 | | g3738097.v113.gs2.nt.edit | 1 | 911 |
| 51 | 7473909CT1 | 332 | | g3962498.v113.gs3.nt.edit | 1 | 332 |
| 52 | 7475252CT1 | 538 | | g4092817.v113.gs1.nt.edit | 1 | 538 |
| 53 | 7927572CT1 | 279 | | g5102597.v113.gs2.nt.edit | 1 | 279 |
| 54 | 7481257CT1 | 291 | | g5262456.v113.gs4.nt.edit | 1 | 291 |
| 55 | 7485790CT1 | 402 | | g5306302.v113.gs6.nt.edit | 1 | 402 |
| 56 | 7482993CT1 | 639 | | g5708153.v113.gs9.nt.edit | 1 | 639 |
| 57 | 2829053CB1 | 1370 | | 170756F1 (BMARNOR02) | 1 | 534 |
| | | | | 2829053F6 (TLYMNOT03) | 428 | 989 |
| | | | | 6098294H1 (UTRENOT09) | 849 | 1143 |
| | | | | 5279076H1 (MUSLNOT01) | 1071 | 1308 |
| | | | | 4588915H1 (MASTTXT01) | 1132 | 1370 |
| 58 | 3068234CB1 | 1567 | | 70489898V1 | 1 | 459 |
| | | | | 70488597V1 | 353 | 883 |
| | | | | 5837294H1 (FTUBTUT01) | 730 | 983 |
| | | | | 70490272V1 | 955 | 1567 |
| 59 | 5029478CB1 | 1321 | | 6035153H1 (PITUNOT06) | 1 | 582 |
| | | | | 6558521H1 (BRAFNON02) | 504 | 1190 |
| | | | | 5076961F6 (COLCTUT03) | 742 | 1321 |
| 60 | 5102576CB1 | 1110 | | 5496406H1 (BRABDIR01) | 1 | 250 |
| | | | | 1720010F6 (BLADNOT06) | 151 | 708 |
| | | | | 6969401U1 | 602 | 710 |
| | | | | 5102576F6 (PROSTUS20) | 673 | 1110 |
| 61 | 2200534CB1 | 1095 | 1037-1095, 372-491 | g2905881.v113.gs__2 | 1 | 948 |
| | | | | 2200534F6 (SPLNFET02) | 534 | 1095 |
| | | | | 576308R6 (BRAVTXT04) | 490 | 1051 |
| 62 | 3275821CB1 | 1665 | 1431-1665, 765-1294, 240-597 | 3275821F6 (PROSBPT06) | 1 | 548 |
| | | | | g3779013.v113.gs__9 | 265 | 1665 |
| 63 | 3744167CB1 | 1609 | 1184-1238, 249-522 | 2762536H1 (BRSTNOT12) | 745 | 994 |
| | | | | g5578767.v113.gs__4 | 262 | 1338 |
| | | | | 3744167H1 (THYNNOT08) | 693 | 977 |
| | | | | g835247 | 1212 | 1609 |
| | | | | 3474586H1 (LUNGNOT27) | 1 | 309 |
| 64 | 7472007CB1 | 945 | | g2431610.v113.gs__4.nt | 1 | 945 |
| 65 | 7472008CB1 | 1098 | | g3093312.v113.gs__10.nt | 1 | 1098 |
| 66 | 7472013CB1 | 954 | | g4190944.v113.gs__3.nt | 1 | 954 |
| 67 | 7472015CB1 | 1008 | | g4467309.v113.gs__2.nt | 1 | 1008 |
| 68 | 7472016CB1 | 930 | | g4567182.v113.gs__19.nt | 1 | 930 |
| 69 | 7472017CB1 | 711 | | g5262456.v113.gs__7.nt | 1 | 711 |
| 70 | 7472018CB1 | 1092 | | g5523795.v113.gs__12.nt | 1 | 1092 |
| 71 | 7472019CB1 | 927 | | g5566548.v113.gs__7.nt | 1 | 927 |
| 72 | 7472021CB1 | 1032 | | g5708153.v113.gs__6.nt | 1 | 1032 |
| 73 | 7472009CB1 | 972 | | g3213020.v113.gs__4.nt | 1 | 972 |
| 74 | 7472010CB1 | 900 | | g3738097.v113.gs__9.nt | 1 | 900 |
| 75 | 7472011CB1 | 924 | | g3924656.v113.gs__5.nt | 1 | 924 |
| 76 | 7472012CB1 | 945 | | g4190944.v113.gs__1.nt | 1 | 945 |
| 77 | 7472014CB1 | 933 | | g4190944.v113.gs__4.nt | 1 | 933 |
| 78 | 7472020CB1 | 1080 | | g5706779.v113.gs__3.nt | 1 | 1080 |

TABLE 5

| Polynucleotide SEQ ID NO: | Incyte Project ID | Representative Library |
|---|---|---|
| 61 | 2200534CB1 | BRAVTXT04 |
| 62 | 3275821CB1 | PROSBPT06 |
| 63 | 3744167CB1 | LUNGNOT27 |

TABLE 6

| Library | Vector | Library Description |
|---|---|---|
| BRAVTXT04 | PSPORT1 | Library was constructed using RNA isolated from separate populations of human astrocytes stimulated for 4 to 6 hours with a combination of cytokines including IL-1. The RNA was pooled for polyA RNA isolation and library construction. |
| LUNGNOT27 | pINCY | Library was constructed using RNA isolated from lung tissue removed from a 17-year-old Hispanic female. |
| PROSBPT06 | pINCY | Library was constructed using RNA isolated from diseased prostate tissue remove from a 66-year-old Caucasian male during a radical prostatectomy and lymph node excision. Pathology indicated adenofibromatous hyperplasia. Pathology for the associated tumor tissue indicated grade 2 (of 4) adenocarcinoma, Gleason grade 3 + 3. The patient presented with elevated prostate specific antigen (PSA), proteinuria, decreased renal function, and urinary frequency. Patient history included hemiparesis, depressive disorder, sleep apnea, psoriasis, mitral valve prolapse, cerebrovascular disease, benign hypertension, and impotence. Family history included benign hypertension, cerebrovascular disease, and colon cancer. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/ PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul. S. F. et al. (1990) J. Mol. Biol. 215: 403-410; Altschul, S. F. et al. (1997) Nucleic Acids Res. 25: 3389-3402. | ESTs: Probability value = 1.0E−8 or less Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6 Assembled ESTs: fasta Identity = 95% or greater and Match length = 200 bases or greater; fastx E value = 1.0E−8 or less Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565-6572; Henikoff, J. G. and S. Henikoff (1996) Methods Enzymol. 266: 88-105; and Attwood, T. K. et al. (1997) J. Chem. Inf. Comput. Sci. 37: 417-424. | Probability value = 1.0E−3 or less |
| HMMER | An algorithm for searching a query sequence against hidden Markov model (HMM)-based databases of protein family consensus sequences, such as PFAM. | Krogh, A. et al. (1994) J. Mol. Biol., 235: 1501-1531; Sonnhammer, E. L. L. et al. (1988) Nucleic Acids Res. 26: 320-322; Durbin, R. et al. (1998) Our World View, in a Nutshell, Cambridge Univ. Press, pp. 1-350. | PFAM hits: Probability value = 1.0E−3 or less Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61-66; Gribskov, M. et al. (1989) Methods Enzymol. 183: 146-159; Bairoch, A. et al. (1997) Nucleic Acids Res. 25: 217-221. | Normalized quality score ≧ GCG-specified "HIGH" value for that particular Prosite motif. Generally, score = 1.4-2.1. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient | Smith. T. F. and M. S. Waterman (1981) Adv. Appl. Math. 2: 482-489; Smith, T. F. and M. S. Waterman (1981) J. Mol. Biol. 147: 195-197; and Green, P., | Score = 120 or greater; Match length = 56 or greater |

TABLE 7-continued

| Program | Description | Reference | Parameter Threshold |
|---|---|---|---|
| | implementation of the Smith-Waterman algorithm, useful in searching sequence homology and assembling DNA sequences. | University of Washington, Seattle, WA. | |
| Consed | A graphical tool for viewing and editing Phrap assemblies. | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 3.5 or greater |
| TMAP | A program that uses weight matrices to delineate transmembrane segments on protein sequences and determine orientation. | Persson, B. and P. Argos (1994) J. Mol. Biol. 237: 182-192; Persson, B. and P. Argos (1996) Protein Sci. 5: 363-371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. on Intelligent Systems for Mol. Biol., Glasgow et al., eds., The Am. Assoc. for Artificial Intelligence Press. Menlo Park, CA, pp. 175-182. | |
| Motifs | A program that searches amino acid sequences for patterns that matched those defined in Prosite. | Bairoch, A. et al. (1997) Nucleic Acids Res. 25: 217-221; Wisconsin Package Program Manual, version 9, page M51-59, Genetics Computer Group, Madison, WI. | |

What is claimed is:

1. An isolated polynucleotide comprising the polynucleotide sequence of SEQ ID NO: 63.

2. A recombinant polynucleotide comprising a promoter sequence operably linked to the polynucleotide of claim 1.

3. An isolated cell transformed with the recombinant polynucleotide of claim 2.

4. A method of producing a polypeptide comprising the amino acid sequence of SEQ ID NO:24, the method comprising:

a) culturing a cell under conditions suitable for expression of the polypeptide, wherein said cell is transformed with a recombinant polynucleotide, and said recombinant polynucleotide comprise a promoter sequence operably linked to the polynucleotide of claim 1, and b) recovering the polypeptide so expressed.

* * * * *

```
                        SEQUENCE LISTING

<160> NUMBER OF SEQ ID NOS: 78

<210> SEQ ID NO 1
<211> LENGTH: 311
<212> TYPE: PRT
<213> ORGANISM: Homo sapiens
<220> FEATURE:
<221> NAME/KEY: misc_feature
<223> OTHER INFORMATION: Incyte ID No: 104941CD1

<400> SEQUENCE: 1

Met Glu Ile Lys Asn Tyr Ser Ser Ser Thr Ser Gly Phe Ile Leu
  1               5                  10                  15

Leu Gly Leu Ser Ser Asn Pro Gln Leu Gln Lys Pro Leu Phe Ala
                 20                  25                  30

Ile Phe Leu Ile Met Tyr Leu Leu Ala Ala Val Gly Asn Val Leu
                 35                  40                  45

Ile Ile Pro Ala Ile Tyr Ser Asp Pro Arg Leu His Thr Pro Met
                 50                  55                  60

Tyr Phe Phe Leu Ser Asn Leu Ser Phe Met Asp Ile Cys Phe Thr
                 65                  70                  75

Thr Val Ile Val Pro Lys Met Leu Val Asn Phe Leu Ser Glu Thr
                 80                  85                  90

Lys Val Ile Ser Tyr Val Gly Cys Leu Ala Gln Met Tyr Phe Phe
                 95                 100                 105

Met Ala Phe Gly Asn Thr Asp Ser Tyr Leu Leu Ala Ser Met Ala
                110                 115                 120

Ile Asp Arg Leu Val Ala Ile Cys Asn Pro Leu His Tyr Asp Val
                125                 130                 135

Val Met Lys Pro Arg His Cys Leu Leu Met Leu Leu Gly Ser Cys
                140                 145                 150

Ser Ile Ser His Leu His Ser Leu Phe Arg Val Leu Leu Met Ser
                155                 160                 165

Arg Leu Ser Phe Cys Ala Ser His Ile Ile Lys His Phe Phe Cys
                170                 175                 180
```

```
Asp Thr Gln Pro Val Leu Lys Leu Ser Cys Ser Asp Thr Ser Ser
                185                 190                 195

Ser Gln Met Val Val Met Thr Glu Thr Leu Ala Val Ile Val Thr
            200                 205                 210

Pro Phe Leu Cys Ile Ile Phe Ser Tyr Leu Arg Ile Met Val Thr
            215                 220                 225

Val Leu Arg Ile Pro Ser Ala Ala Gly Lys Trp Lys Ala Phe Ser
            230                 235                 240

Thr Cys Gly Ser His Leu Thr Ala Val Ala Leu Phe Tyr Gly Ser
            245                 250                 255

Ile Ile Tyr Val Tyr Phe Arg Pro Leu Ser Met Tyr Ser Val Val
            260                 265                 270

Arg Asp Arg Val Ala Thr Val Met Tyr Thr Val Val Thr Pro Met
            275                 280                 285

Leu Asn Pro Phe Ile Tyr Ser Leu Arg Asn Lys Asp Met Lys Arg
            290                 295                 300

Gly Leu Lys Lys Leu Gln Asp Arg Ile Tyr Arg
            305                 310

<210> SEQ ID NO 2
<211> LENGTH: 891
<212> TYPE: PRT
<213> ORGANISM: Homo sapiens
<220> FEATURE:
<221> NAME/KEY: misc_feature
<223> OTHER INFORMATION: Incyte ID No: 1499408CD1

<400> SEQUENCE: 2

Met Asp Gln Pro Glu Ala Pro Cys Ser Ser Thr Gly Pro Arg Leu
 1               5                  10                  15

Ala Val Ala Arg Glu Leu Leu Leu Ala Ala Leu Glu Glu Leu Ser
                20                  25                  30

Gln Glu Gln Leu Lys Arg Phe Arg His Lys Leu Arg Asp Val Gly
            35                  40                  45

Pro Asp Gly Arg Ser Ile Pro Trp Gly Arg Leu Glu Arg Ala Asp
        50                  55                  60

Ala Val Asp Leu Ala Glu Gln Leu Ala Gln Phe Tyr Gly Pro Glu
65                  70                  75

Pro Ala Leu Glu Val Ala Arg Lys Thr Leu Lys Arg Ala Asp Ala
                80                  85                  90

Arg Asp Val Ala Ala Gln Leu Gln Glu Arg Arg Leu Gln Arg Leu
            95                 100                 105

Gly Leu Gly Ser Gly Thr Leu Leu Ser Val Ser Glu Tyr Lys Lys
        110                 115                 120

Lys Tyr Arg Glu His Val Leu Gln Leu His Ala Arg Val Lys Glu
                125                 130                 135

Arg Asn Ala Arg Ser Val Lys Ile Thr Lys Arg Phe Thr Lys Leu
            140                 145                 150

Leu Ile Ala Pro Glu Ser Ala Ala Pro Glu Glu Ala Leu Gly Pro
        155                 160                 165

Ala Glu Glu Pro Glu Pro Gly Arg Ala Arg Ser Asp Thr His
                170                 175                 180

Thr Phe Asn Arg Leu Phe Arg Arg Asp Glu Glu Gly Arg Arg Pro
            185                 190                 195

Leu Thr Val Val Leu Gln Gly Pro Ala Gly Ile Gly Lys Thr Met
```

```
                        200                 205                 210
Ala Ala Lys Lys Ile Leu Tyr Asp Trp Ala Gly Lys Leu Tyr
                215                 220                 225
Gln Gly Gln Val Asp Phe Ala Phe Phe Met Pro Cys Gly Glu Leu
                230                 235                 240
Leu Glu Arg Pro Gly Thr Arg Ser Leu Ala Asp Leu Ile Leu Asp
                245                 250                 255
Gln Cys Pro Asp Arg Gly Ala Pro Val Pro Gln Met Leu Ala Gln
                260                 265                 270
Pro Gln Arg Leu Leu Phe Ile Leu Asp Gly Ala Asp Glu Leu Pro
                275                 280                 285
Ala Leu Gly Gly Pro Glu Ala Ala Pro Cys Thr Asp Pro Phe Glu
                290                 295                 300
Ala Ala Ser Gly Ala Arg Val Leu Gly Gly Leu Leu Ser Lys Ala
                305                 310                 315
Leu Leu Pro Thr Ala Leu Leu Leu Val Thr Thr Arg Ala Ala Ala
                320                 325                 330
Pro Gly Arg Leu Gln Gly Arg Leu Cys Ser Pro Gln Cys Ala Glu
                335                 340                 345
Val Arg Gly Phe Ser Asp Lys Asp Lys Lys Tyr Phe Tyr Lys
                350                 355                 360
Phe Phe Arg Asp Glu Arg Ala Glu Arg Ala Tyr Arg Phe Val
                365                 370                 375
Lys Glu Asn Glu Thr Leu Phe Ala Leu Cys Phe Val Pro Phe Val
                380                 385                 390
Cys Trp Ile Val Cys Thr Val Leu Arg Gln Gln Leu Glu Leu Gly
                395                 400                 405
Arg Asp Leu Ser Arg Thr Ser Lys Thr Thr Ser Val Tyr Leu
                410                 415                 420
Leu Phe Ile Thr Ser Val Leu Ser Ser Ala Pro Val Ala Asp Gly
                425                 430                 435
Pro Arg Leu Gln Gly Asp Leu Arg Asn Leu Cys Arg Leu Ala Arg
                440                 445                 450
Glu Gly Val Leu Gly Arg Arg Ala Gln Phe Ala Glu Lys Glu Leu
                455                 460                 465
Glu Gln Leu Glu Leu Arg Gly Ser Lys Val Gln Thr Leu Phe Leu
                470                 475                 480
Ser Lys Lys Glu Leu Pro Gly Val Leu Glu Thr Glu Val Thr Tyr
                485                 490                 495
Gln Phe Ile Asp Gln Ser Phe Gln Glu Phe Leu Ala Ala Leu Ser
                500                 505                 510
Tyr Leu Leu Glu Asp Gly Gly Val Pro Arg Thr Ala Ala Gly Gly
                515                 520                 525
Val Gly Thr Leu Leu Arg Gly Asp Ala Gln Pro His Ser His Leu
                530                 535                 540
Val Leu Thr Thr Arg Phe Leu Phe Gly Leu Leu Ser Ala Glu Arg
                545                 550                 555
Met Arg Asp Ile Glu Arg His Phe Gly Cys Met Val Ser Glu Arg
                560                 565                 570
Val Lys Gln Glu Ala Leu Arg Trp Val Gln Gly Gln Gly Gln
                575                 580                 585
Cys Pro Gly Val Ala Pro Glu Val Thr Glu Gly Ala Lys Gly Leu
                590                 595                 600
```

```
Glu Asp Thr Glu Glu Pro Glu Glu Glu Gly Glu Pro
            605                 610                 615

Asn Tyr Pro Leu Glu Leu Leu Tyr Cys Leu Tyr Glu Thr Gln Glu
            620                 625                 630

Asp Ala Phe Val Arg Gln Ala Leu Cys Arg Phe Pro Glu Leu Ala
            635                 640                 645

Leu Gln Arg Val Arg Phe Cys Arg Met Asp Val Ala Val Leu Ser
            650                 655                 660

Tyr Cys Val Arg Cys Cys Pro Ala Gly Gln Ala Leu Arg Leu Ile
            665                 670                 675

Ser Cys Arg Leu Val Ala Ala Gln Glu Lys Lys Lys Ser Leu
            680                 685                 690

Gly Lys Arg Leu Gln Ala Ser Leu Gly Gly Gly Ser Ser Gln Gly
            695                 700                 705

Thr Thr Lys Gln Leu Pro Ala Ser Leu Leu His Pro Leu Phe Gln
            710                 715                 720

Ala Met Thr Asp Pro Leu Cys His Leu Ser Ser Leu Thr Leu Ser
            725                 730                 735

His Cys Lys Leu Pro Asp Ala Val Cys Arg Asp Leu Ser Glu Ala
            740                 745                 750

Leu Arg Ala Ala Pro Ala Leu Thr Glu Leu Gly Leu Leu His Asn
            755                 760                 765

Arg Leu Ser Glu Ala Gly Leu Arg Met Leu Ser Glu Gly Leu Ala
            770                 775                 780

Trp Pro Gln Cys Arg Val Gln Thr Val Arg Val Gln Leu Pro Asp
            785                 790                 795

Pro Gln Arg Gly Leu Gln Tyr Leu Val Gly Met Leu Arg Gln Ser
            800                 805                 810

Pro Ala Leu Thr Thr Leu Asp Leu Ser Gly Cys Gln Leu Pro Ala
            815                 820                 825

Pro Met Val Thr Tyr Leu Cys Ala Val Leu Gln His Gln Gly Cys
            830                 835                 840

Gly Leu Gln Thr Leu Ser Leu Ala Ser Val Glu Leu Ser Glu Gln
            845                 850                 855

Ser Leu Gln Glu Leu Gln Ala Val Lys Arg Ala Lys Pro Asp Leu
            860                 865                 870

Val Ile Thr His Pro Ala Leu Asp Gly His Pro Gln Pro Pro Lys
            875                 880                 885

Glu Leu Ile Ser Thr Phe
            890

<210> SEQ ID NO 3
<211> LENGTH: 422
<212> TYPE: PRT
<213> ORGANISM: Homo sapiens
<220> FEATURE:
<221> NAME/KEY: misc_feature
<223> OTHER INFORMATION: Incyte ID No: 3168839CD1

<400> SEQUENCE: 3

Met Leu Ala Asn Ser Ser Ser Thr Asn Ser Ser Val Leu Pro Cys
  1               5                  10                  15

Pro Asp Tyr Arg Pro Thr His Arg Leu His Leu Val Val Tyr Ser
                 20                  25                  30

Leu Val Leu Ala Ala Gly Leu Pro Leu Asn Ala Leu Ala Leu Trp
```

-continued

```
                35                  40                  45
Val Phe Leu Arg Ala Leu Arg Val His Ser Val Val Ser Val Tyr
                50                  55                  60
Met Cys Asn Leu Ala Ala Ser Asp Leu Phe Thr Leu Ser Leu
            65                  70                  75
Pro Val Arg Leu Ser Tyr Tyr Ala Leu His His Trp Pro Phe Pro
                80                  85                  90
Asp Leu Leu Cys Gln Thr Thr Gly Ala Ile Phe Gln Met Asn Met
                95                 100                 105
Tyr Gly Ser Cys Ile Phe Leu Met Leu Ile Asn Val Asp Arg Tyr
               110                 115                 120
Ala Ala Ile Val His Pro Leu Arg Leu Arg His Leu Arg Arg Pro
               125                 130                 135
Arg Val Ala Arg Leu Leu Cys Leu Gly Val Trp Ala Leu Ile Leu
               140                 145                 150
Val Phe Ala Val Pro Ala Ala Arg Val His Arg Pro Ser Arg Cys
               155                 160                 165
Arg Tyr Arg Asp Leu Glu Val Arg Leu Cys Phe Glu Ser Phe Ser
               170                 175                 180
Asp Glu Leu Trp Lys Gly Arg Leu Leu Pro Leu Val Leu Leu Ala
               185                 190                 195
Glu Ala Leu Gly Phe Leu Leu Pro Leu Ala Ala Val Val Tyr Ser
               200                 205                 210
Ser Gly Arg Val Phe Trp Thr Leu Ala Arg Pro Asp Ala Thr Gln
               215                 220                 225
Ser Gln Arg Arg Arg Lys Thr Val Arg Leu Leu Leu Ala Asn Leu
               230                 235                 240
Val Ile Phe Leu Leu Cys Phe Val Pro Tyr Asn Ser Thr Leu Ala
               245                 250                 255
Val Tyr Gly Leu Leu Arg Ser Lys Leu Val Ala Ala Ser Val Pro
               260                 265                 270
Ala Arg Asp Arg Val Arg Gly Val Leu Met Val Met Val Leu Leu
               275                 280                 285
Ala Gly Ala Asn Cys Val Leu Asp Pro Leu Val Tyr Tyr Phe Ser
               290                 295                 300
Ala Glu Gly Phe Arg Asn Thr Leu Arg Gly Leu Gly Thr Pro His
               305                 310                 315
Arg Ala Arg Thr Ser Ala Thr Asn Gly Thr Arg Ala Ala Leu Ala
               320                 325                 330
Gln Ser Glu Arg Ser Ala Val Thr Thr Asp Ala Thr Arg Pro Asp
               335                 340                 345
Ala Ala Met Ser Pro Gly Phe Arg Pro Leu Asn Thr His Ala Ile
               350                 355                 360
Ala Leu Ser Val Pro Asp Ser Gln Arg Leu Ser Phe Trp Glu Ala
               365                 370                 375
Tyr Arg Val Tyr Thr Gln Glu Gly Gly Leu Gly Thr Trp Thr Phe
               380                 385                 390
Gly Trp Gln Phe Gln Leu Ser Asn Ala Glu Glu Tyr Lys Val Trp
               395                 400                 405
Lys Pro Gly Pro Arg Glu Gly Ser Ala Ala Gly Asn Gly Phe Phe
               410                 415                 420
Lys Leu
```

```
<210> SEQ ID NO 4
<211> LENGTH: 609
<212> TYPE: PRT
<213> ORGANISM: Homo sapiens
<220> FEATURE:
<221> NAME/KEY: misc_feature
<223> OTHER INFORMATION: Incyte ID No: 3291235CD1

<400> SEQUENCE: 4

Met Ser Asp Glu Arg Arg Leu Pro Gly Ser Ala Val Gly Trp Leu
 1               5                  10                  15

Val Cys Gly Gly Leu Ser Leu Leu Ala Asn Ala Trp Gly Ile Leu
                20                  25                  30

Ser Val Gly Ala Lys Gln Lys Lys Trp Lys Pro Leu Glu Phe Leu
                35                  40                  45

Leu Cys Thr Leu Ala Ala Thr His Met Leu Asn Val Ala Val Pro
                50                  55                  60

Ile Ala Thr Tyr Ser Val Val Gln Leu Arg Arg Gln Arg Pro Asp
                65                  70                  75

Phe Glu Trp Asn Glu Gly Leu Cys Lys Val Phe Val Ser Thr Phe
                80                  85                  90

Tyr Thr Leu Thr Leu Ala Thr Cys Phe Ser Val Thr Ser Leu Ser
                95                  100                 105

Tyr His Arg Met Trp Met Val Cys Trp Pro Val Asn Tyr Arg Leu
                110                 115                 120

Ser Asn Ala Lys Lys Gln Ala Val His Thr Val Met Gly Ile Trp
                125                 130                 135

Met Val Ser Phe Ile Leu Ser Ala Leu Pro Ala Val Gly Trp His
                140                 145                 150

Asp Thr Ser Glu Arg Phe Tyr Thr His Gly Cys Arg Phe Ile Val
                155                 160                 165

Ala Glu Ile Gly Leu Gly Phe Gly Val Cys Phe Leu Leu Leu Val
                170                 175                 180

Gly Gly Ser Val Ala Met Gly Val Ile Cys Thr Ala Ile Ala Leu
                185                 190                 195

Phe Gln Thr Leu Ala Val Gln Val Gly Arg Gln Ala Asp His Arg
                200                 205                 210

Ala Phe Thr Val Pro Thr Ile Val Val Glu Asp Ala Gln Gly Lys
                215                 220                 225

Arg Arg Ser Ser Ile Asp Gly Ser Glu Pro Ala Lys Thr Ser Leu
                230                 235                 240

Gln Thr Thr Gly Leu Val Thr Thr Ile Val Phe Ile Tyr Asp Cys
                245                 250                 255

Leu Met Gly Phe Pro Val Leu Val Val Ser Phe Ser Ser Leu Arg
                260                 265                 270

Ala Asp Ala Ser Ala Pro Trp Met Ala Leu Cys Val Leu Trp Cys
                275                 280                 285

Ser Val Ala Gln Ala Leu Leu Leu Pro Val Phe Leu Trp Ala Cys
                290                 295                 300

Asp Arg Tyr Arg Ala Asp Leu Lys Ala Val Arg Glu Lys Cys Met
                305                 310                 315

Ala Leu Met Ala Asn Asp Glu Glu Ser Asp Asp Glu Thr Ser Leu
                320                 325                 330

Glu Gly Gly Ile Ser Pro Asp Leu Val Leu Glu Arg Ser Leu Asp
                335                 340                 345
```

-continued

```
Tyr Gly Tyr Gly Gly Asp Phe Val Ala Leu Asp Arg Met Ala Lys
            350                 355                 360

Tyr Glu Ile Ser Ala Leu Glu Gly Gly Leu Pro Gln Leu Tyr Pro
            365                 370                 375

Leu Arg Pro Leu Gln Glu Asp Lys Met Gln Tyr Leu Gln Val Pro
            380                 385                 390

Pro Thr Arg Arg Phe Ser His Asp Asp Ala Asp Val Trp Ala Ala
            395                 400                 405

Val Pro Leu Pro Ala Phe Leu Pro Arg Trp Gly Ser Gly Lys Asp
            410                 415                 420

Leu Ser Ala Leu Ala His Leu Val Leu Pro Ala Gly Pro Glu Arg
            425                 430                 435

Pro Arg Ala Ser Leu Leu Ala Phe Ala Glu Asp Ala Pro Leu Ser
            440                 445                 450

Arg Ala Arg Arg Arg Ser Ala Glu Ser Leu Leu Ser Leu Arg Pro
            455                 460                 465

Ser Ala Val Asp Ser Gly Pro Arg Gly Ala Arg Asp Ser Pro Pro
            470                 475                 480

Gly Ser Pro Arg Arg Pro Gly Pro Gly Pro Arg Ser Ala Ser
            485                 490                 495

Ala Ser Leu Leu Pro Asp Ala Phe Ala Leu Thr Ala Phe Glu Cys
            500                 505                 510

Glu Pro Gln Ala Leu Arg Arg Pro Pro Gly Pro Phe Pro Ala Ala
            515                 520                 525

Pro Ala Ala Pro Asp Gly Ala Asp Pro Gly Glu Ala Pro Thr Pro
            530                 535                 540

Pro Ser Ser Ala Gln Arg Ser Pro Gly Pro Arg Pro Ser Ala His
            545                 550                 555

Ser His Ala Gly Ser Leu Arg Pro Gly Leu Ser Ala Ser Trp Gly
            560                 565                 570

Glu Pro Gly Gly Leu Arg Ala Ala Gly Gly Gly Ser Thr Ser
            575                 580                 585

Ser Phe Leu Ser Ser Pro Ser Glu Ser Ser Gly Tyr Ala Thr Leu
            590                 595                 600

His Ser Asp Ser Leu Gly Ser Ala Ser
            605

<210> SEQ ID NO 5
<211> LENGTH: 313
<212> TYPE: PRT
<213> ORGANISM: Homo sapiens
<220> FEATURE:
<221> NAME/KEY: misc_feature
<223> OTHER INFORMATION: Incyte ID No: 7472001CD1

<400> SEQUENCE: 5

Met Glu Arg Ile Asn Ser Thr Leu Leu Thr Ala Phe Ile Leu Thr
  1               5                  10                  15

Gly Ile Pro Tyr Pro Leu Arg Leu Arg Thr Leu Phe Phe Val Phe
                 20                  25                  30

Phe Phe Leu Ile Tyr Ile Leu Thr Gln Leu Gly Asn Leu Leu Ile
                 35                  40                  45

Leu Ile Thr Val Trp Ala Asp Pro Arg Leu His Ala Arg Pro Met
                 50                  55                  60

Tyr Ile Phe Leu Gly Val Leu Ser Val Ile Asp Met Ser Ile Ser
```

```
                 65                  70                  75
Ser Ile Ile Val Pro Arg Leu Met Met Asn Phe Thr Leu Gly Val
             80                  85                  90

Lys Pro Ile Pro Phe Gly Gly Cys Val Ala Gln Leu Tyr Phe Tyr
             95                 100                 105

His Phe Leu Gly Ser Thr Gln Cys Phe Leu Tyr Thr Leu Met Ala
            110                 115                 120

Tyr Asp Arg Tyr Leu Ala Ile Cys Gln Pro Leu Arg Tyr Pro Val
            125                 130                 135

Leu Met Thr Ala Lys Leu Ser Ala Leu Leu Val Ala Gly Ala Trp
            140                 145                 150

Met Ala Gly Ser Ile His Gly Ala Leu Gln Ala Ile Leu Thr Phe
            155                 160                 165

Arg Leu Pro Tyr Cys Gly Pro Asn Gln Val Asp Tyr Phe Phe Cys
            170                 175                 180

Asp Ile Pro Ala Val Leu Arg Leu Ala Cys Ala Asp Thr Thr Val
            185                 190                 195

Asn Glu Leu Val Thr Phe Val Asp Ile Gly Val Val Val Ala Ser
            200                 205                 210

Cys Phe Ser Leu Ile Leu Leu Ser Tyr Ile Gln Ile Ile Gln Ala
            215                 220                 225

Ile Leu Arg Ile His Thr Ala Asp Gly Arg Arg Ala Phe Ser
            230                 235                 240

Thr Cys Gly Ala His Val Thr Val Val Thr Val Tyr Tyr Val Pro
            245                 250                 255

Cys Ala Phe Ile Tyr Leu Arg Pro Glu Thr Asn Ser Pro Leu Asp
            260                 265                 270

Gly Ala Ala Ala Leu Val Pro Thr Ala Ile Thr Pro Phe Leu Asn
            275                 280                 285

Pro Leu Ile Tyr Thr Leu Arg Asn Gln Glu Val Lys Leu Ala Leu
            290                 295                 300

Lys Arg Met Leu Arg Ser Pro Arg Thr Pro Ser Glu Val
            305                 310
```

<210> SEQ ID NO 6
<211> LENGTH: 398
<212> TYPE: PRT
<213> ORGANISM: Homo sapiens
<220> FEATURE:
<221> NAME/KEY: misc_feature
<223> OTHER INFORMATION: Incyte ID No: 7472003CD1

<400> SEQUENCE: 6

```
Met His Thr Val Ala Thr Ser Gly Pro Asn Ala Ser Trp Gly Ala
  1               5                  10                  15

Pro Ala Asn Ala Ser Gly Cys Pro Gly Cys Gly Ala Asn Ala Ser
             20                  25                  30

Asp Gly Pro Val Pro Ser Pro Arg Ala Val Asp Ala Trp Leu Val
             35                  40                  45

Pro Leu Phe Phe Ala Ala Leu Met Leu Leu Gly Leu Val Gly Asn
             50                  55                  60

Ser Leu Val Ile Tyr Val Ile Cys Arg His Lys Pro Met Arg Thr
             65                  70                  75

Val Thr Asn Phe Tyr Ile Ala Asn Leu Ala Ala Thr Asp Val Thr
             80                  85                  90
```

```
Phe Leu Leu Cys Cys Val Pro Phe Thr Ala Leu Leu Tyr Pro Leu
                 95                 100                 105

Pro Gly Trp Val Leu Gly Asp Phe Met Cys Lys Phe Val Asn Tyr
            110                 115                 120

Ile Gln Gln Val Ser Val Gln Ala Thr Cys Ala Thr Leu Thr Ala
            125                 130                 135

Met Ser Val Asp Arg Trp Tyr Val Thr Val Phe Pro Leu Arg Ala
            140                 145                 150

Leu His Arg Arg Thr Pro Arg Leu Ala Leu Ala Val Ser Leu Ser
            155                 160                 165

Ile Trp Thr Gly Ser Ala Ala Val Ser Ala Pro Val Leu Ala Leu
            170                 175                 180

His Arg Leu Ser Pro Gly Pro Arg Ala Tyr Cys Ser Glu Ala Phe
            185                 190                 195

Pro Ser Arg Ala Leu Glu Arg Ala Phe Ala Leu Tyr Asn Leu Leu
            200                 205                 210

Ala Leu Tyr Leu Leu Pro Leu Leu Ala Thr Cys Ala Cys Tyr Ala
            215                 220                 225

Ala Met Leu Arg His Leu Gly Arg Val Ala Val Arg Pro Ala Pro
            230                 235                 240

Ala Asp Ser Ala Leu Gln Gly Gln Val Leu Ala Glu Arg Ala Gly
            245                 250                 255

Ala Val Arg Ala Lys Val Ser Arg Leu Val Ala Ala Val Val Leu
            260                 265                 270

Leu Phe Ala Ala Cys Trp Gly Pro Ile Gln Leu Phe Leu Val Leu
            275                 280                 285

Gln Ala Leu Gly Pro Ala Gly Ser Trp His Pro Arg Ser Tyr Ala
            290                 295                 300

Ala Tyr Ala Leu Lys Thr Trp Ala His Cys Met Ser Tyr Ser Asn
            305                 310                 315

Ser Ala Leu Asn Pro Leu Leu Tyr Ala Phe Leu Gly Ser His Phe
            320                 325                 330

Arg Gln Ala Phe Arg Arg Val Cys Pro Cys Ala Pro Arg Arg Pro
            335                 340                 345

Arg Arg Pro Arg Arg Pro Gly Pro Ser Asp Pro Ala Ala Pro His
            350                 355                 360

Ala Glu Leu Leu Arg Leu Gly Ser His Pro Ala Pro Ala Arg Ala
            365                 370                 375

Gln Lys Pro Gly Ser Ser Gly Leu Ala Ala Arg Gly Leu Cys Val
            380                 385                 390

Leu Gly Glu Asp Asn Ala Pro Leu
            395

<210> SEQ ID NO 7
<211> LENGTH: 369
<212> TYPE: PRT
<213> ORGANISM: Homo sapiens
<220> FEATURE:
<221> NAME/KEY: misc_feature
<223> OTHER INFORMATION: Incyte ID No: 7472004CD1

<400> SEQUENCE: 7

Met Ala Pro Thr Gly Leu Ser Ser Leu Thr Val Asn Ser Thr Ala
 1               5                  10                  15

Val Pro Thr Thr Pro Ala Ala Phe Lys Ser Leu Asn Leu Pro Leu
             20                  25                  30
```

```
Gln Ile Thr Leu Ser Ala Ile Met Ile Phe Ile Leu Phe Val Ser
             35                  40                  45

Phe Leu Gly Asn Leu Val Val Cys Leu Met Val Tyr Gln Lys Ala
             50                  55                  60

Ala Met Arg Ser Ala Ile Asn Ile Leu Leu Ala Ser Leu Ala Phe
             65                  70                  75

Ala Asp Met Leu Leu Ala Val Leu Asn Met Pro Phe Ala Leu Val
             80                  85                  90

Thr Ile Leu Thr Thr Arg Trp Ile Phe Gly Lys Phe Phe Cys Arg
             95                 100                 105

Val Ser Ala Met Phe Phe Trp Leu Phe Val Ile Glu Gly Val Ala
            110                 115                 120

Ile Leu Leu Ile Ile Ser Ile Asp Arg Phe Leu Ile Ile Val Gln
            125                 130                 135

Arg Gln Asp Lys Leu Asn Pro Tyr Arg Ala Lys Val Leu Ile Ala
            140                 145                 150

Val Ser Trp Ala Thr Ser Phe Cys Val Ala Phe Pro Leu Ala Val
            155                 160                 165

Gly Asn Pro Asp Leu Gln Ile Pro Ser Arg Ala Pro Gln Cys Val
            170                 175                 180

Phe Gly Tyr Thr Thr Asn Pro Gly Tyr Gln Ala Tyr Val Ile Leu
            185                 190                 195

Ile Ser Leu Ile Ser Phe Phe Ile Pro Phe Leu Val Ile Leu Tyr
            200                 205                 210

Ser Phe Met Gly Ile Leu Asn Thr Leu Arg His Asn Ala Leu Arg
            215                 220                 225

Ile His Ser Tyr Pro Glu Gly Ile Cys Leu Ser Gln Ala Ser Lys
            230                 235                 240

Leu Gly Leu Met Ser Leu Gln Arg Pro Phe Gln Met Ser Ile Asp
            245                 250                 255

Met Gly Phe Lys Thr Arg Ala Phe Thr Thr Ile Leu Ile Leu Phe
            260                 265                 270

Ala Val Phe Ile Val Cys Trp Ala Pro Phe Thr Thr Tyr Ser Leu
            275                 280                 285

Val Ala Thr Phe Ser Lys His Phe Tyr Tyr Gln His Asn Phe Phe
            290                 295                 300

Glu Ile Ser Thr Trp Leu Leu Trp Leu Cys Tyr Leu Lys Ser Ala
            305                 310                 315

Leu Asn Pro Leu Ile Tyr Tyr Trp Arg Ile Lys Lys Phe His Asp
            320                 325                 330

Ala Cys Leu Asp Met Met Pro Lys Ser Phe Lys Phe Leu Pro Gln
            335                 340                 345

Leu Pro Gly His Thr Lys Arg Ile Arg Pro Ser Ala Val Tyr
            350                 355                 360

Val Cys Gly Glu His Arg Thr Val Val
            365

<210> SEQ ID NO 8
<211> LENGTH: 194
<212> TYPE: PRT
<213> ORGANISM: Homo sapiens
<220> FEATURE:
<221> NAME/KEY: misc_feature
<223> OTHER INFORMATION: Incyte ID No: 7475687CP1
```

```
<400> SEQUENCE: 8

Met Ala Tyr Asp Arg Tyr Leu Ala Ile Cys Gln Pro Leu Arg Tyr
 1               5                  10                  15

Pro Val Leu Met Asn Gly Arg Leu Cys Thr Val Leu Val Ala Gly
                20                  25                  30

Ala Trp Val Ala Gly Ser Met His Gly Ser Ile Gln Ala Thr Leu
                35                  40                  45

Thr Phe Arg Leu Pro Tyr Cys Gly Pro Asn Gln Val Asp Tyr Phe
                50                  55                  60
Ile Cys Asp Ile Pro Ala Val Leu Arg Leu Ala Cys Ala Asp Thr
                65                  70                  75
Thr Val Asn Glu Leu Val Thr Phe Val Asp Ile Gly Val Val Ala
                80                  85                  90
Ala Ser Cys Phe Met Leu Ile Leu Leu Ser Tyr Ala Asn Ile Val
                95                  100                 105
Asn Ala Ile Leu Lys Ile Arg Thr Thr Asp Gly Arg Arg Arg Ala
                110                 115                 120
Phe Ser Thr Cys Gly Ser His Leu Ile Val Val Thr Val Tyr Tyr
                125                 130                 135
Val Pro Cys Ile Phe Ile Tyr Leu Arg Ala Gly Ser Lys Gly Pro
                140                 145                 150
Leu Asp Gly Ala Ala Ala Val Phe Tyr Thr Val Val Thr Pro Leu
                155                 160                 165
Leu Asn Pro Leu Ile Tyr Thr Leu Arg Asn Gln Glu Val Lys Ser
                170                 175                 180
Ala Leu Lys Arg Ile Thr Ala Gly Gln Ala Asp Val Asn Asn
                185                 190

<210> SEQ ID NO 9
<211> LENGTH: 173
<212> TYPE: PRT
<213> ORGANISM: Homo sapiens
<220> FEATURE:
<221> NAME/KEY: misc_feature
<223> OTHER INFORMATION: Incyte ID No: 7483029CP1

<400> SEQUENCE: 9

Met Tyr Leu Val Thr Val Leu Gly Asn Leu Leu Ile Ile Leu Ala
 1               5                  10                  15

Thr Ile Ser Asp Ser His Leu His Thr Pro Met Tyr Phe Phe Leu
                20                  25                  30

Ser Asn Leu Ser Phe Ala Asp Ile Cys Phe Val Ser Thr Thr Val
                35                  40                  45

Pro Lys Met Leu Val Asn Ile Gln Thr Gln Ser Arg Val Ile Thr
                50                  55                  60

Tyr Ala Asp Cys Ile Thr Gln Met Cys Phe Phe Ile Leu Phe Val
                65                  70                  75

Val Leu Asp Ser Leu Leu Leu Thr Val Met Ala Tyr Asp Arg Phe
                80                  85                  90

Val Ala Ile Cys His Pro Leu His Tyr Thr Val Ile Met Asn Ser
                95                  100                 105

Trp Leu Cys Gly Leu Leu Val Leu Val Ser Trp Ile Val Ser Ile
                110                 115                 120

Leu Tyr Ser Leu Leu Gln Ser Ile Met Ala Leu Gln Leu Ser Phe
                125                 130                 135

Cys Thr Glu Leu Lys Ile Pro His Phe Phe Cys Glu Leu Asn Gln
                140                 145                 150

Val Ile His Leu Ala Cys Ser Asp Thr Phe Ile Asn Asp Met Met
                155                 160                 165

Met Asn Phe Thr Ser Val Leu Leu
                170
```

```
<210> SEQ ID NO 10
<211> LENGTH: 220
<212> TYPE: PRT
<213> ORGANISM: Homo sapiens
<220> FEATURE:
<221> NAME/KEY: misc_feature
<223> OTHER INFORMATION: Incyte ID No: 7477933CP1

<400> SEQUENCE: 10

Pro Met Tyr Phe Phe Leu Ser Asn Leu Cys Trp Ala Asp Ile Gly
 1               5                  10                  15

Leu Thr Ser Ala Thr Val Pro Lys Val Ile Leu Asp Met Gln Ser
                20                  25                  30

His Ser Arg Val Ile Ser His Val Gly Cys Leu Thr Gln Met Ser
            35                  40                  45

Phe Leu Val Leu Phe Ala Cys Ile Glu Gly Met Leu Leu Thr Val
        50                  55                  60

Met Ala Tyr Gly Cys Phe Val Ala Ile Cys Arg Pro Leu His Tyr
    65                  70                  75

Pro Val Ile Val Asn Pro His Leu Cys Val Phe Phe Val Leu Val
            80                  85                  90

Ser Phe Phe Leu Asn Leu Leu Asp Ser Gln Leu His Ser Trp Ile
        95                  100                 105

Val Leu Gln Phe Thr Ile Ile Lys Asn Val Glu Ile Ser Asn Phe
    110                 115                 120

Phe Cys Asp Pro Ser Gln Leu Leu Asn Leu Ala Cys Ser Asp Ser
            125                 130                 135

Val Ile Asn Ser Ile Phe Ile Tyr Phe Asp Ser Thr Met Phe Gly
        140                 145                 150

Phe Leu Pro Ile Ser Gly Ile Leu Ser Tyr Tyr Lys Ile Val
    155                 160                 165

Pro Ser Ile Leu Arg Met Ser Ser Asp Gly Lys Tyr Lys Ala
            170                 175                 180

Phe Ser Thr Tyr Gly Ser His Leu Gly Val Val Cys Trp Phe Tyr
        185                 190                 195

Gly Thr Val Ile Gly Met Tyr Leu Ala Ser Ala Val Ser Pro Pro
    200                 205                 210

Pro Arg Asn Gly Val Val Ala Ser Val Met
            215                 220

<210> SEQ ID NO 11
<211> LENGTH: 302
<212> TYPE: PRT
<213> ORGANISM: Homo sapiens
<220> FEATURE:
<221> NAME/KEY: misc_feature
<223> OTHER INFORMATION: Incyte ID No: 7475164CP1

<400> SEQUENCE: 11

Ala Glu Phe Ile Leu Ala Gly Leu Thr Gln Arg Pro Glu Leu Gln
 1               5                  10                  15

Leu Pro Leu Phe Leu Leu Phe Leu Gly Ile Tyr Val Val Thr Val
                20                  25                  30

Val Gly Asn Leu Gly Met Ile Phe Leu Ile Ala Leu Ser Ser Gln
            35                  40                  45

Leu Tyr Pro Pro Val Tyr Tyr Phe Leu Ser His Leu Ser Phe Ile
        50                  55                  60
```

-continued

```
Asp Leu Cys Tyr Ser Ser Val Ile Thr Pro Lys Met Leu Val Asn
                 65                  70                  75

Phe Val Pro Glu Glu Asn Ile Ile Ser Phe Leu Glu Cys Ile Thr
             80                  85                  90

Gln Leu Tyr Phe Phe Leu Ile Phe Val Ile Ala Glu Gly Tyr Leu
             95                 100                 105

Leu Thr Ala Met Glu Tyr Asp Arg Tyr Val Ala Ile Cys Arg Pro
            110                 115                 120

Leu Leu Tyr Asn Ile Val Met Ser His Arg Val Cys Ser Ile Met
            125                 130                 135

Met Ala Val Val Tyr Ser Leu Gly Phe Leu Trp Ala Thr Val His
            140                 145                 150

Thr Thr Arg Met Ser Val Leu Ser Phe Cys Arg Ser His Thr Val
            155                 160                 165

Ser His Tyr Phe Cys Asp Ile Leu Pro Leu Leu Thr Leu Ser Cys
            170                 175                 180

Ser Ser Thr His Ile Asn Glu Ile Leu Leu Phe Ile Ile Gly Gly
            185                 190                 195

Val Asn Thr Leu Ala Thr Thr Leu Ala Val Leu Ile Ser Tyr Ala
            200                 205                 210

Phe Ile Phe Ser Ser Ile Leu Gly Ile His Ser Thr Glu Gly Gln
            215                 220                 225

Ser Lys Ala Phe Gly Thr Cys Ser Ser His Leu Leu Ala Val Gly
            230                 235                 240

Ile Phe Phe Gly Ser Ile Thr Phe Met Tyr Phe Lys Pro Pro Ser
            245                 250                 255

Ser Thr Thr Met Glu Lys Glu Lys Val Ser Ser Val Phe Tyr Ile
            260                 265                 270

Thr Ile Ile Pro Met Leu Asn Pro Leu Ile Tyr Ser Leu Arg Asn
            275                 280                 285

Lys Asp Val Lys Asn Ala Leu Lys Lys Met Thr Arg Gly Arg Gln
            290                 295                 300

Ser Ser
```

<210> SEQ ID NO 12
<211> LENGTH: 110
<212> TYPE: PRT
<213> ORGANISM: Homo sapiens
<220> FEATURE:
<221> NAME/KEY: misc_feature
<223> OTHER INFORMATION: Incyte ID No: 7473909CP1

<400> SEQUENCE: 12

```
Gly Pro Arg Thr Ala Ser Gly Cys Val Ile Met Ile Cys Phe Ala
 1               5                  10                  15

Leu Thr Val Leu Ser Tyr Ile Arg Ile Leu Ala Thr Val Val Gln
             20                  25                  30

Ile Arg Ser Ala Ala Ser Arg Arg Lys Ala Phe Ser Thr Cys Ser
             35                  40                  45

Ser His Leu Gly Met Val Leu Leu Phe Tyr Gly Thr Gly Ser Ser
             50                  55                  60

Thr Tyr Met Arg Pro Thr Thr Arg Tyr Ser Pro Leu Glu Gly Arg
             65                  70                  75

Leu Ala Ala Val Phe Tyr Ser Ile Leu Ile Pro Thr Leu Asn Pro
             80                  85                  90
```

```
Leu Ile Tyr Ser Leu Arg Asn Gln Asp Met Lys Arg Ala Leu Trp
                95                 100                 105

Lys Leu Tyr Leu Gln
            110
```

<210> SEQ ID NO 13
<211> LENGTH: 178
<212> TYPE: PRT
<213> ORGANISM: Homo sapiens
<220> FEATURE:
<221> NAME/KEY: misc_feature
<223> OTHER INFORMATION: Incyte ID No: 7475252CP1

<400> SEQUENCE: 13

```
Glu Pro Glu Asn Leu Thr Gly Val Leu Glu Phe Leu Leu Leu Gly
  1               5                  10                  15

Leu Pro Asp Asp Pro Glu Leu Gln Pro Val Leu Phe Gly Leu Phe
                 20                  25                  30

Leu Ser Met Tyr Leu Val Met Val Leu Gly Asn Leu Leu Ile Ile
                 35                  40                  45

Leu Ala Val Ser Ser Asp Ser His Leu His Ser Pro Met Tyr Phe
                 50                  55                  60

Phe Leu Ser Asn Leu Ser Leu Ala Asp Ile Gly Phe Ala Ser Thr
 65                  70                                  75

Thr Val Pro Lys Met Ile Val Asp Ile Gln Ala His Ser Arg Leu
                 80                  85                  90

Ile Ser Tyr Val Gly Cys Leu Thr Gln Met Ser Phe Leu Ile Phe
                 95                 100                 105

Phe Ala Cys Met Glu Ser Leu Leu Leu Ile Val Met Ala Tyr Asp
                110                 115                 120

Arg Phe Val Ala Ile Cys His Pro Leu His Tyr Gln Val Ile Met
                125                 130                 135

Ser Pro Arg Leu Cys Gly Phe Leu Val Leu Val Ser Phe Phe Leu
                140                 145                 150

Ser Leu Leu Asp Ser Gln Leu His Asn Leu Ile Val Leu Gln Leu
                155                 160                 165

Thr Cys Phe Asn Asp Val Glu Ile Ser Asn Phe Phe Leu
                170                 175
```

<210> SEQ ID NO 14
<211> LENGTH: 92
<212> TYPE: PRT
<213> ORGANISM: Homo sapiens
<220> FEATURE:
<221> NAME/KEY: misc_feature
<223> OTHER INFORMATION: Incyte ID No: 7927572CP1

<400> SEQUENCE: 14

```
Leu Leu Asp Ala Gln Leu Tyr Asn Leu Ile Ala Leu Gln Met Thr
  1               5                  10                  15

Cys Phe Lys Asp Val Glu Ile Pro Asn Phe Phe Cys Asp Pro Ser
                 20                  25                  30

Gln Leu Pro His Leu Ala Cys Cys Asp Thr Phe Asn Asn Asn Ile
                 35                  40                  45

Ile Leu Tyr Phe Pro Asp Ala Ile Phe Gly Phe Leu Pro Ile Ser
                 50                  55                  60

Gly Thr Leu Phe Ser Tyr Asp Lys Ile Val Ser Ser Ile Leu Arg
 65                  70                                  75
```

-continued

```
Val Ser Ser Gly Gly Lys Tyr Lys Ala Phe Ser Thr Tyr Gly
            80                  85                  90

Ser His

<210> SEQ ID NO 15
<211> LENGTH: 97
<212> TYPE: PRT
<213> ORGANISM: Homo sapiens
<220> FEATURE:
<221> NAME/KEY: misc_feature
<223> OTHER INFORMATION: Incyte ID No: 7481257CP1

<400> SEQUENCE: 15

Met Glu Val Thr Thr Phe Ala Met Cys Leu Ile Ile Val Leu Val
  1               5                  10                  15

Pro Leu Leu Ile Leu Val Ser Tyr Gly Phe Ile Ala Val Ala
                 20                  25                  30

Val Leu Lys Ile Lys Ser Ala Ala Gly Arg Gln Lys Ala Phe Gly
                 35                  40                  45

Thr Cys Ser Ser His Leu Val Val Ser Ile Phe Cys Gly Thr
                 50                  55                  60

Val Thr Tyr Met Tyr Ile Gln Pro Gly Asn Ser Pro Asn Gln Asn
                 65                  70                  75

Glu Gly Lys Leu Leu Ser Ile Phe Tyr Ser Ile Val Thr Pro Ser
                 80                  85                  90

Leu Asn Pro Leu Ile Tyr Thr
                 95

<210> SEQ ID NO 16
<211> LENGTH: 133
<212> TYPE: PRT
<213> ORGANISM: Homo sapiens
<220> FEATURE:
<221> NAME/KEY: misc_feature
<223> OTHER INFORMATION: Incyte ID No: 7485790CP1

<400> SEQUENCE: 16

Asp Pro Glu Leu Gln Pro Ile Leu Ala Gly Leu Ser Leu Ser Met
  1               5                  10                  15

Tyr Leu Val Thr Val Leu Arg Asn Leu Leu Ile Ser Leu Ala Val
                 20                  25                  30

Ser Ser Asp Ser His Leu His Thr Pro Met Cys Phe Phe Leu Ser
                 35                  40                  45

Asn Leu Cys Trp Ala Asp Ile Gly Phe Thr Ser Ala Thr Val Pro
                 50                  55                  60

Lys Met Ile Val Asp Met Arg Ser His Ser Gly Val Ile Ser Tyr
                 65                  70                  75

Ala Asp Cys Leu Thr Arg Met Ser Phe Leu Val Leu Phe Ala Cys
                 80                  85                  90

Val Glu Asp Met Leu Leu Thr Val Met Ala Tyr Asp Cys Phe Val
                 95                  100                 105

Ala Ile Cys Arg Pro Leu His Tyr Pro Val Ile Val Asn Pro His
                 110                 115                 120

Leu Cys Val Phe Leu Val Ser Val Ser Phe Ser Leu Ala
                 125                 130

<210> SEQ ID NO 17
<211> LENGTH: 213
<212> TYPE: PRT
```

-continued

```
<213> ORGANISM: Homo sapiens
<220> FEATURE:
<221> NAME/KEY: misc_feature
<223> OTHER INFORMATION: Incyte ID No: 7482993CP1

<400> SEQUENCE: 17
```

Gly Ser Glu Cys Leu Leu Leu Ala Ala Met Ala Tyr Asp Arg Tyr
 1               5                  10                  15

Ile Ala Ile Cys Asn Pro Leu Arg Tyr Ser Val Ile Leu Ser Lys
            20                  25                  30

Val Leu Cys Asn Gln Leu Ala Ala Ser Cys Trp Ala Ala Gly Phe
        35                  40                  45

Leu Asn Ser Val Val His Thr Val Leu Thr Phe Cys Leu Pro Phe
    50                  55                  60

Cys Gly Asn Asn Gln Ile Asn Tyr Phe Phe Cys Asp Ile Pro Pro
65                  70                  75

Leu Leu Ile Leu Ser Cys Gly Asn Thr Ser Val Asn Glu Leu Ala
                80                  85                  90

Leu Leu Ser Thr Gly Val Phe Ile Gly Trp Thr Pro Phe Leu Cys
            95                 100                 105

Ile Val Leu Ser Tyr Ile Cys Ile Ile Ser Thr Ile Leu Arg Ile
        110                 115                 120

Gln Ser Ser Glu Gly Arg Arg Lys Ala Phe Ser Thr Cys Ala Ser
    125                 130                 135

His Leu Ala Ile Val Phe Leu Phe Tyr Gly Ser Ala Ile Phe Thr
140                 145                 150

Tyr Val Arg Pro Ile Ser Thr Tyr Ser Leu Lys Lys Asp Arg Leu
                155                 160                 165

Val Ser Val Leu Tyr Ser Val Val Thr Pro Met Leu Asn Pro Ile
            170                 175                 180

Ile Tyr Thr Leu Arg Asn Lys Asp Ile Lys Glu Ala Val Lys Thr
        185                 190                 195

Ile Gly Ser Lys Trp Gln Pro Pro Ile Ser Ser Leu Asp Ser Lys
    200                 205                 210

Leu Thr Tyr

```
<210> SEQ ID NO 18
<211> LENGTH: 180
<212> TYPE: PRT
<213> ORGANISM: Homo sapiens
<220> FEATURE:
<221> NAME/KEY: misc_feature
<223> OTHER INFORMATION: Incyte ID No: 2829053CD1

<400> SEQUENCE: 18
```

Met Ser Glu Ala Ala Thr Arg Trp Ser Cys Gln Gly Ser Cys Gln
 1               5                  10                  15

Lys Thr Cys Phe Ser Arg Val Arg Pro Trp Arg Arg Cys Ser
            20                  25                  30

Cys Gly Asp Ser Ser Ser Arg Arg Arg Ser Cys Cys Thr Gly
        35                  40                  45

Ser Leu Gly Pro Met Pro Arg Leu Pro Ser Leu Trp Pro Leu Ser
    50                  55                  60

Leu Pro Leu Arg Ser Leu Ser Ser Pro His Arg Val Gln Gly Leu
65                  70                  75

Gly Pro Pro Arg Arg Leu Lys Ser Gln Leu Leu Pro Arg Phe Phe
                80                  85                  90

```
Trp Arg Arg Gln Gln Glu Pro Leu Ser Ser Phe Pro Gly Arg Asn
             95                 100                 105

Glu Gly Gly Ser Glu Met Glu Ile Leu Gly Val Cys Pro Val Ser
            110                 115                 120

Pro Gly Ala Leu Ser Tyr Met Glu Ser Pro Thr Gly Phe Trp Arg
            125                 130                 135

Pro Arg Glu Ala Ser Ser Leu Glu Leu Ala Lys Gly Ile Ser Lys
            140                 145                 150

Arg Arg His Phe Leu Pro Ala Pro Ala Leu Cys Pro Asn Pro Arg
            155                 160                 165

Ser Ser Glu Ala Phe Pro Gly Ala Val Cys Val Thr Leu Ala Ile
            170                 175                 180

<210> SEQ ID NO 19
<211> LENGTH: 353
<212> TYPE: PRT
<213> ORGANISM: Homo sapiens
<220> FEATURE:
<221> NAME/KEY: misc_feature
<223> OTHER INFORMATION: Incyte ID No: 3068234CD1

<400> SEQUENCE: 19

Met Asn Glu Cys His Tyr Asp Lys His Met Asp Phe Phe Tyr Asn
  1               5                  10                  15

Arg Ser Asn Thr Asp Thr Val Asp Asp Trp Thr Gly Thr Lys Leu
             20                  25                  30

Val Ile Val Leu Cys Val Gly Thr Phe Phe Cys Leu Phe Ile Phe
             35                  40                  45

Phe Ser Asn Ser Leu Val Ile Ala Ala Val Ile Lys Asn Arg Lys
             50                  55                  60

Phe His Phe Pro Phe Tyr Tyr Leu Leu Ala Asn Leu Ala Ala Ala
             65                  70                  75

Asp Phe Phe Ala Gly Ile Ala Tyr Val Phe Leu Met Phe Asn Thr
             80                  85                  90

Gly Pro Val Ser Lys Thr Leu Thr Val Asn Arg Trp Phe Leu Arg
             95                 100                 105

Gln Gly Leu Leu Asp Ser Ser Leu Thr Ala Ser Leu Thr Asn Leu
            110                 115                 120

Leu Val Ile Ala Val Glu Arg His Met Ser Ile Met Arg Met Arg
            125                 130                 135

Val His Ser Asn Leu Thr Lys Lys Arg Val Thr Leu Leu Ile Leu
            140                 145                 150

Leu Val Trp Ala Ile Ala Ile Phe Met Gly Ala Val Pro Thr Leu
            155                 160                 165

Gly Trp Asn Cys Leu Cys Asn Ile Ser Ala Cys Ser Ser Leu Ala
            170                 175                 180

Pro Ile Tyr Ser Arg Ser Tyr Leu Val Phe Trp Thr Val Ser Asn
            185                 190                 195

Leu Met Ala Phe Leu Ile Met Val Val Val Tyr Leu Arg Ile Tyr
            200                 205                 210

Val Tyr Val Lys Arg Lys Thr Asn Val Leu Ser Pro His Thr Ser
            215                 220                 225

Gly Ser Ile Ser Arg Arg Arg Thr Pro Met Lys Leu Met Lys Thr
            230                 235                 240

Val Met Thr Val Leu Gly Ala Phe Val Val Cys Trp Thr Pro Gly
```

-continued

```
                245                 250                 255

Leu Val Val Leu Leu Leu Asp Gly Leu Asn Cys Arg Gln Cys Gly
                260                 265                 270

Val Gln His Val Lys Arg Trp Phe Leu Leu Ala Leu Leu Asn
                275                 280                 285

Ser Val Val Asn Pro Ile Ile Tyr Ser Tyr Lys Asp Glu Asp Met
                290                 295                 300

Tyr Gly Thr Met Lys Lys Met Ile Cys Cys Phe Ser Gln Glu Asn
                305                 310                 315

Pro Glu Arg Arg Pro Ser Arg Ile Pro Ser Thr Val Leu Ser Arg
                320                 325                 330

Ser Asp Thr Gly Ser Gln Tyr Ile Glu Asp Ser Ile Ser Gln Gly
                335                 340                 345

Ala Val Cys Asn Lys Ser Thr Ser
                350

<210> SEQ ID NO 20
<211> LENGTH: 361
<212> TYPE: PRT
<213> ORGANISM: Homo sapiens
<220> FEATURE:
<221> NAME/KEY: misc_feature
<223> OTHER INFORMATION: Incyte ID No: 5029478CD1

<400> SEQUENCE: 20

Met Ser Pro Glu Cys Ala Arg Ala Ala Gly Asp Ala Pro Leu Arg
  1               5                  10                  15

Ser Leu Glu Gln Ala Asn Arg Thr Arg Phe Pro Phe Ser Asp
                 20                  25                  30

Val Lys Gly Asp His Arg Leu Val Leu Ala Ala Val Glu Thr Thr
                 35                  40                  45

Val Leu Val Leu Ile Phe Ala Val Ser Leu Leu Gly Asn Val Cys
                 50                  55                  60

Ala Leu Val Leu Val Ala Arg Arg Arg Arg Gly Ala Thr Ala
                 65                  70                  75

Cys Leu Val Leu Asn Leu Phe Cys Ala Asp Leu Leu Phe Ile Ser
                 80                  85                  90

Ala Ile Pro Leu Val Leu Ala Val Arg Trp Thr Glu Ala Trp Leu
                 95                 100                 105

Leu Gly Pro Val Ala Cys His Leu Leu Phe Tyr Val Met Thr Leu
                110                 115                 120

Ser Gly Ser Val Thr Ile Leu Thr Leu Ala Ala Val Ser Leu Glu
                125                 130                 135

Arg Met Val Cys Ile Val His Leu Gln Arg Gly Val Arg Gly Pro
                140                 145                 150

Gly Arg Arg Ala Arg Ala Val Leu Leu Ala Leu Ile Trp Gly Tyr
                155                 160                 165

Ser Ala Val Ala Ala Leu Pro Leu Cys Val Phe Phe Arg Val Val
                170                 175                 180

Pro Gln Arg Leu Pro Gly Ala Asp Gln Glu Ile Ser Ile Cys Thr
                185                 190                 195

Leu Ile Trp Pro Thr Ile Pro Gly Glu Ile Ser Trp Asp Val Ser
                200                 205                 210

Phe Val Thr Leu Asn Phe Leu Val Pro Gly Leu Val Ile Val Ile
                215                 220                 225
```

-continued

```
Ser Tyr Ser Lys Ile Leu Gln Ile Thr Lys Ala Ser Arg Lys Arg
                230                 235                 240

Leu Thr Val Ser Leu Ala Tyr Ser Glu Ser His Gln Ile Arg Val
            245                 250                 255

Ser Gln Gln Asp Phe Arg Leu Phe Arg Thr Leu Phe Leu Leu Met
        260                 265                 270

Val Ser Phe Phe Ile Met Trp Ser Pro Ile Ile Thr Ile Leu
    275                 280                 285

Leu Ile Leu Ile Gln Asn Phe Lys Gln Asp Leu Val Ile Trp Pro
            290                 295                 300

Ser Leu Phe Phe Trp Val Val Ala Phe Thr Phe Ala Asn Ser Ala
        305                 310                 315

Leu Asn Pro Ile Leu Tyr Asn Met Thr Leu Cys Arg Asn Glu Trp
    320                 325                 330

Lys Lys Ile Phe Cys Cys Phe Trp Phe Pro Glu Lys Gly Ala Ile
            335                 340                 345

Leu Thr Asp Thr Ser Val Lys Arg Asn Asp Leu Ser Ile Ile Ser
        350                 355                 360

Gly

<210> SEQ ID NO 21
<211> LENGTH: 251
<212> TYPE: PRT
<213> ORGANISM: Homo sapiens
<220> FEATURE:
<221> NAME/KEY: misc_feature
<223> OTHER INFORMATION: Incyte ID No: 5102576CD1

<400> SEQUENCE: 21

Met Tyr Leu Val Thr Val Leu Arg Asn Leu Phe Ser Ile Leu Ala
 1               5                  10                  15

Val Ser Ser Asp Cys Pro Leu His Thr Pro Met Tyr Phe Phe Leu
                20                  25                  30

Ser Asn Leu Cys Trp Pro Asp Ile Gly Phe Thr Ser Ala Met Val
            35                  40                  45

Pro Lys Met Ile Val Asp Thr Gln Ser His Ser Arg Val Ile Ser
        50                  55                  60

His Ala Gly Cys Leu Thr Gln Met Ser Phe Leu Leu Leu Val Ala
    65                  70                  75

Cys Ile Glu Gly Met Leu Leu Thr Val Met Ala Tyr Asp Cys Phe
            80                  85                  90

Val Ala Ile Cys Arg Pro Leu His Tyr Pro Val Ile Val Asn Pro
        95                 100                 105

His Leu Cys Val Phe Phe Val Leu Val Ser Phe Leu Ser Leu
    110                 115                 120

Leu Asp Ser Gln Leu His Ser Trp Ile Val Leu Gln Leu Thr Ile
            125                 130                 135

Ile Lys Asn Val Glu Ile Ser Asn Leu Val Cys Asp Pro Ser Gln
        140                 145                 150

Leu Leu Asn Leu Ala Cys Ser Asp Ser Val Ile Asn Asn Ile Phe
    155                 160                 165

Ile Tyr Phe Asp Ser Thr Met Phe Gly Phe Leu Pro Ile Ser Gly
            170                 175                 180

Ile Phe Leu Ser Tyr Tyr Lys Ile Val Pro Ser Ile Leu Arg Ile
        185                 190                 195
```

```
Ser Ser Ser Asp Gly Lys Tyr Lys Ala Phe Ser Thr Cys Gly Cys
            200                 205                 210

His Leu Ala Val Val Cys Trp Phe Tyr Gly Thr Gly Ile Gly Met
            215                 220                 225

Tyr Leu Thr Ser Ala Val Ser Pro Pro Arg Asn Gly Val Val
            230                 235                 240

Ala Ser Val Met Tyr Ala Val Val Thr Pro Cys
            245                 250

<210> SEQ ID NO 22
<211> LENGTH: 315
<212> TYPE: PRT
<213> ORGANISM: Homo sapiens
<220> FEATURE:
<221> NAME/KEY: misc_feature
<223> OTHER INFORMATION: Incyte ID No: 2200534CD1

<400> SEQUENCE: 22

Met Lys Ala Asn Tyr Ser Ala Glu Glu Arg Phe Leu Leu Leu Gly
  1               5                  10                  15

Phe Ser Asp Trp Pro Ser Leu Gln Pro Val Leu Phe Ala Leu Val
             20                  25                  30

Leu Leu Cys Tyr Leu Leu Thr Leu Thr Gly Asn Ser Ala Leu Val
             35                  40                  45

Leu Leu Ala Val Arg Asp Pro Arg Leu His Thr Pro Met Tyr Tyr
             50                  55                  60

Phe Leu Cys His Leu Ala Leu Val Asp Ala Gly Phe Thr Thr Ser
             65                  70                  75

Val Val Pro Pro Leu Leu Ala Asn Leu Arg Gly Pro Ala Leu Trp
             80                  85                  90

Leu Pro Arg Ser His Cys Thr Ala Gln Leu Cys Ala Ser Leu Ala
             95                 100                 105

Leu Gly Ser Ala Glu Cys Val Leu Leu Ala Val Met Ala Leu Asp
            110                 115                 120

Arg Ala Ala Ala Val Cys Arg Pro Leu Arg Tyr Ala Gly Leu Val
            125                 130                 135

Ser Pro Arg Leu Cys Arg Thr Leu Ala Ser Ala Ser Trp Leu Ser
            140                 145                 150

Gly Leu Thr Asn Ser Val Ala Gln Thr Ala Leu Leu Ala Glu Arg
            155                 160                 165

Pro Leu Cys Ala Pro Arg Leu Leu Asp His Phe Ile Cys Glu Leu
            170                 175                 180

Pro Ala Leu Leu Lys Leu Ala Cys Gly Gly Asp Gly Asp Thr Thr
            185                 190                 195

Glu Asn Gln Met Phe Ala Ala Arg Val Val Ile Leu Leu Leu Pro
            200                 205                 210

Phe Ala Val Ile Leu Ala Ser Tyr Gly Ala Val Ala Arg Ala Val
            215                 220                 225

Cys Cys Met Arg Phe Ser Gly Gly Arg Arg Arg Ala Val Gly Thr
            230                 235                 240

Cys Gly Ser His Leu Thr Ala Val Cys Leu Phe Tyr Gly Ser Ala
            245                 250                 255

Ile Tyr Thr Tyr Leu Gln Pro Ala Gln Arg Tyr Asn Gln Ala Arg
            260                 265                 270

Gly Lys Phe Val Ser Leu Phe Tyr Thr Val Val Thr Pro Ala Leu
            275                 280                 285
```

Asn Pro Leu Ile Tyr Thr Leu Arg Asn Lys Lys Val Lys Gly Ala
            290                 295                 300

Ala Arg Arg Leu Leu Arg Ser Leu Gly Arg Gly Gln Ala Gly Gln
            305                 310                 315

<210> SEQ ID NO 23
<211> LENGTH: 470
<212> TYPE: PRT
<213> ORGANISM: Homo sapiens
<220> FEATURE:
<221> NAME/KEY: misc_feature
<223> OTHER INFORMATION: Incyte ID No: 3275821CD1

<400> SEQUENCE: 23

Met Asp Thr Thr Met Glu Ala Asp Leu Gly Ala Thr Gly His Arg
  1               5                  10                  15

Pro Arg Thr Glu Leu Asp Asp Glu Asp Ser Tyr Pro Gln Gly Gly
             20                  25                  30

Trp Asp Thr Val Phe Leu Val Ala Leu Leu Leu Gly Leu Pro
             35                  40                  45

Ala Asn Gly Leu Met Ala Trp Leu Ala Gly Ser Gln Ala Arg His
             50                  55                  60

Gly Ala Gly Thr Arg Leu Ala Leu Leu Leu Ser Leu Ala Leu
             65                  70                  75

Ser Asp Phe Leu Phe Leu Ala Ala Ala Ala Phe Gln Ile Leu Glu
             80                  85                  90

Ile Arg His Gly Gly His Trp Pro Leu Gly Thr Ala Ala Cys Arg
             95                 100                 105

Phe Tyr Tyr Phe Leu Trp Gly Val Ser Tyr Ser Ser Gly Leu Phe
            110                 115                 120

Leu Leu Ala Ala Leu Ser Leu Asp Arg Cys Leu Leu Ala Leu Cys
            125                 130                 135

Pro His Trp Tyr Pro Gly His Arg Pro Val Arg Leu Pro Leu Trp
            140                 145                 150

Val Cys Ala Gly Val Trp Val Leu Ala Thr Leu Phe Ser Val Pro
            155                 160                 165

Trp Leu Val Phe Pro Glu Ala Ala Val Trp Trp Tyr Asp Leu Val
            170                 175                 180

Ile Cys Leu Asp Phe Trp Asp Ser Glu Glu Leu Ser Leu Arg Met
            185                 190                 195

Leu Glu Val Leu Gly Gly Phe Leu Pro Phe Leu Leu Leu Leu Val
            200                 205                 210

Cys His Val Leu Thr Gln Ala Thr Ala Cys Arg Thr Cys His Arg
            215                 220                 225

Gln Gln Gln Pro Ala Ala Cys Arg Gly Phe Ala Arg Val Ala Arg
            230                 235                 240

Thr Ile Leu Ser Ala Tyr Val Val Leu Arg Leu Pro Tyr Gln Leu
            245                 250                 255

Ala Gln Leu Leu Tyr Leu Ala Phe Leu Trp Asp Val Tyr Ser Gly
            260                 265                 270

Tyr Leu Leu Trp Glu Ala Leu Val Tyr Ser Asp Tyr Leu Ile Leu
            275                 280                 285

Leu Asn Ser Cys Leu Ser Pro Phe Leu Cys Leu Met Ala Ser Ala
            290                 295                 300

Asp Leu Arg Thr Leu Leu Arg Ser Val Leu Ser Ser Phe Ala Ala

```
                       305                 310                 315
Ala Leu Cys Glu Glu Arg Pro Gly Ser Phe Thr Pro Thr Glu Pro
                320                 325                 330

Gln Thr Gln Leu Asp Ser Glu Gly Pro Thr Leu Pro Glu Pro Met
            335                 340                 345

Ala Glu Ala Gln Ser Gln Met Asp Pro Val Ala Gln Pro Gln Val
        350                 355                 360

Asn Pro Thr Leu Gln Pro Arg Ser Asp Pro Thr Ala Gln Pro Gln
    365                 370                 375

Leu Asn Pro Thr Ala Gln Pro Gln Ser Asp Pro Thr Ala Gln Pro
380                 385                 390

Gln Leu Asn Leu Met Ala Gln Pro Gln Ser Asp Ser Val Ala Gln
            395                 400                 405

Pro Gln Ala Asp Thr Asn Val Gln Thr Pro Ala Pro Ala Ala Ser
        410                 415                 420

Ser Val Pro Ser Pro Cys Asp Glu Ala Ser Pro Thr Pro Ser Ser
    425                 430                 435

His Pro Thr Pro Gly Ala Leu Glu Asp Pro Ala Thr Pro Ala
440                 445                 450

Ser Glu Gly Glu Ser Pro Ser Ser Thr Pro Pro Glu Ala Ala Pro
            455                 460                 465

Gly Ala Gly Pro Thr
            470

<210> SEQ ID NO 24
<211> LENGTH: 358
<212> TYPE: PRT
<213> ORGANISM: Homo sapiens
<220> FEATURE:
<221> NAME/KEY: misc_feature
<223> OTHER INFORMATION: Incyte ID No: 3744167CD1

<400> SEQUENCE: 24

Met Ser Val Cys Tyr Arg Pro Pro Gly Asn Glu Thr Leu Leu Ser
  1               5                  10                  15

Trp Lys Thr Ser Arg Ala Thr Gly Thr Ala Phe Leu Leu Leu Ala
             20                  25                  30

Ala Leu Leu Gly Leu Pro Gly Asn Gly Phe Val Val Trp Ser Leu
         35                  40                  45

Ala Gly Trp Arg Pro Ala Arg Gly Arg Pro Leu Ala Ala Thr Leu
     50                  55                  60

Val Leu His Leu Ala Leu Ala Asp Gly Ala Val Leu Leu Leu Thr
 65                  70                  75

Pro Leu Phe Val Ala Phe Leu Thr Arg Gln Ala Trp Pro Leu Gly
             80                  85                  90

Gln Ala Gly Cys Lys Ala Val Tyr Tyr Val Cys Ala Leu Ser Met
         95                 100                 105

Tyr Ala Ser Val Leu Leu Thr Gly Leu Leu Ser Leu Gln Arg Cys
    110                 115                 120

Leu Ala Val Thr Arg Pro Phe Leu Ala Pro Arg Leu Arg Ser Pro
125                 130                 135

Ala Leu Ala Arg Arg Leu Leu Leu Ala Val Trp Leu Ala Ala Leu
            140                 145                 150

Leu Leu Ala Val Pro Ala Ala Val Tyr Arg His Leu Trp Arg Asp
        155                 160                 165
```

```
Arg Val Cys Gln Leu Cys His Pro Ser Pro Val His Ala Ala Ala
            170                 175                 180

His Leu Ser Leu Glu Thr Leu Thr Ala Phe Val Leu Pro Phe Gly
            185                 190                 195

Leu Met Leu Gly Cys Tyr Ser Val Thr Leu Ala Arg Leu Arg Gly
            200                 205                 210

Ala Arg Trp Gly Ser Arg His Gly Ala Arg Val Gly Arg Leu
            215                 220                 225

Val Ser Ala Ile Val Leu Ala Phe Gly Leu Leu Trp Ala Pro Tyr
            230                 235                 240

His Ala Val Asn Leu Leu Gln Ala Val Ala Ala Leu Ala Pro Pro
            245                 250                 255

Glu Gly Ala Leu Ala Lys Leu Gly Gly Ala Gly Gln Ala Ala Arg
            260                 265                 270

Ala Gly Thr Thr Ala Leu Ala Phe Phe Ser Ser Val Asn Pro
            275                 280                 285

Val Leu Tyr Val Phe Thr Ala Gly Asp Leu Leu Pro Arg Ala Gly
            290                 295                 300

Pro Arg Phe Leu Thr Arg Leu Phe Glu Gly Ser Gly Glu Ala Arg
            305                 310                 315

Gly Gly Gly Arg Ser Arg Glu Gly Thr Met Glu Leu Arg Thr Thr
            320                 325                 330

Pro Gln Leu Lys Val Val Gly Gln Gly Arg Gly Asn Gly Asp Pro
            335                 340                 345

Gly Gly Gly Met Glu Lys Asp Gly Pro Glu Trp Asp Leu
            350                 355

<210> SEQ ID NO 25
<211> LENGTH: 314
<212> TYPE: PRT
<213> ORGANISM: Homo sapiens
<220> FEATURE:
<221> NAME/KEY: misc_feature
<223> OTHER INFORMATION: Incyte ID No: 7472007CD1

<400> SEQUENCE: 25

Met Trp Glu Asn Trp Thr Ile Val Ser Glu Phe Val Leu Val Ser
 1               5                  10                  15

Phe Ser Ala Leu Ser Thr Glu Leu Gln Ala Leu Leu Phe Leu Leu
            20                  25                  30

Phe Leu Thr Ile Tyr Leu Val Thr Leu Met Gly Asn Val Leu Ile
            35                  40                  45

Ile Leu Val Thr Ile Ala Asp Ser Ala Leu Gln Ser Pro Met Tyr
            50                  55                  60

Phe Phe Leu Arg Asn Leu Ser Phe Leu Glu Ile Gly Phe Asn Leu
            65                  70                  75

Val Ile Val Pro Lys Met Leu Gly Thr Leu Ile Ile Gln Asp Thr
            80                  85                  90

Thr Ile Ser Phe Leu Gly Cys Ala Thr Gln Met Tyr Phe Phe Phe
            95                  100                 105

Phe Phe Gly Ala Ala Glu Cys Cys Leu Leu Ala Thr Met Ala Tyr
            110                 115                 120

Asp Arg Tyr Val Ala Ile Cys Asp Pro Leu His Tyr Pro Val Ile
            125                 130                 135

Met Gly His Ile Ser Cys Ala Gln Leu Ala Ala Ala Ser Trp Phe
            140                 145                 150
```

```
Ser Gly Phe Ser Val Ala Thr Val Gln Thr Thr Trp Ile Phe Ser
            155                 160                 165

Phe Pro Phe Cys Gly Pro Asn Arg Val Asn His Phe Cys Asp
            170                 175                 180

Ser Pro Pro Val Ile Ala Leu Val Cys Ala Asp Thr Ser Val Phe
            185                 190                 195

Glu Leu Glu Ala Leu Thr Ala Thr Val Pro Phe Ile Leu Phe Pro
            200                 205                 210

Phe Leu Leu Ile Leu Gly Ser Tyr Val Arg Ile Leu Ser Thr Ile
            215                 220                 225

Phe Arg Met Pro Ser Ala Glu Gly Lys His Gln Ala Phe Ser Thr
            230                 235                 240

Cys Ser Ala His Leu Leu Val Val Ser Leu Phe Tyr Ser Thr Ala
            245                 250                 255

Ile Leu Thr Tyr Phe Arg Pro Gln Ser Ser Ala Ser Ser Glu Ser
            260                 265                 270

Lys Lys Leu Leu Ser Leu Ser Ser Thr Val Val Thr Pro Met Leu
            275                 280                 285

Asn Pro Ile Ile Tyr Ser Ser Arg Asn Lys Glu Val Lys Ala Ala
            290                 295                 300

Leu Lys Arg Leu Ile His Arg Thr Leu Gly Ser Gln Lys Leu
            305                 310

<210> SEQ ID NO 26
<211> LENGTH: 365
<212> TYPE: PRT
<213> ORGANISM: Homo sapiens
<220> FEATURE:
<221> NAME/KEY: misc_feature
<223> OTHER INFORMATION: Incyte ID No: 7472008CD1

<400> SEQUENCE: 26

Met Glu Gly Ser Val Glu Ala Thr Pro Glu Ile Pro Ala Gln Met
  1               5                  10                  15

Lys Cys His Pro Ser Arg Pro Ser Thr Leu Asn Gln Leu Ser Phe
             20                  25                  30

Tyr Gly Ala Val Ser Ser Leu Gly Arg Met His Gly Leu Glu Thr
             35                  40                  45

Lys Ser Ser Ala Glu Ile Arg Ala Gly Leu Lys Arg Cys Asp Thr
             50                  55                  60

Leu Val Leu Glu Ala Ser Thr Leu Glu Gly Asn Met Val Ile Val
             65                  70                  75

Leu Val Ser Leu Lys Asp Pro Lys Leu His Ile Pro Met Tyr Phe
             80                  85                  90

Phe Leu Ser Asn Leu Ser Leu Val Asp Leu Cys Leu Thr Ser Ser
             95                 100                 105

Cys Val Pro Gln Met Leu Ile Asn Phe Trp Gly Pro Glu Lys Thr
            110                 115                 120

Ile Ser Tyr Ile Gly Cys Ala Ile Gln Leu Tyr Val Phe Leu Trp
            125                 130                 135

Leu Gly Ala Thr Glu Tyr Val Leu Leu Val Met Ala Val Asp
            140                 145                 150

Cys Tyr Val Ala Val Cys His Pro Leu Gln Asn Thr Met Ile Met
            155                 160                 165

His Pro Lys Leu Cys Leu Gln Leu Ala Ile Leu Ala Trp Gly Thr
```

```
                170                 175                 180
Gly Leu Ala Gln Ser Leu Ile Gln Ser Pro Ala Thr Leu Arg Leu
                185                 190                 195

Pro Phe Cys Ser Gln Arg Met Val Asp Asp Val Val Cys Glu Val
                200                 205                 210

Pro Ala Leu Ile Gln Leu Ser Ser Thr Asp Thr Thr Tyr Ser Glu
                215                 220                 225

Ile Gln Met Ser Ile Ala Ser Val Val Leu Val Met Pro Leu
                230                 235                 240

Ile Ile Ile Leu Ser Ser Gly Ala Ile Ala Lys Ala Val Leu
                245                 250                 255

Arg Ile Lys Ser Thr Ala Gly Gln Lys Lys Ala Phe Gly Thr Cys
                260                 265                 270

Ile Ser His Leu Leu Val Val Ser Leu Phe Tyr Gly Thr Val Thr
                275                 280                 285

Gly Val Tyr Leu Gln Pro Lys Asn His Tyr Pro His Glu Trp Gly
                290                 295                 300

Lys Phe Leu Thr Leu Phe Tyr Thr Val Val Thr Pro Thr Leu Asn
                305                 310                 315

Pro Leu Ile Tyr Thr Leu Arg Asn Lys Glu Leu His Pro Trp Leu
                320                 325                 330

Lys Glu Ala Lys Val Gln Thr Ala Ser Glu Ser Ala Ser Pro Lys
                335                 340                 345

His Trp Gln Leu Pro His Gly Val Gly Pro Val Gly Val Gln Lys
                350                 355                 360

Thr Arg Thr Glu Leu
                365

<210> SEQ ID NO 27
<211> LENGTH: 317
<212> TYPE: PRT
<213> ORGANISM: Homo sapiens
<220> FEATURE:
<221> NAME/KEY: misc_feature
<223> OTHER INFORMATION: Incyte ID No: 7472013CD1

<400> SEQUENCE: 27

Met Ser Phe Ala Pro Asn Ala Ser His Ser Pro Val Phe Leu Leu
  1               5                  10                  15

Leu Gly Phe Ser Arg Ala Asn Ile Ser Tyr Thr Leu Leu Phe Phe
                 20                  25                  30

Leu Phe Leu Ala Ile Tyr Leu Thr Thr Ile Leu Gly Asn Val Thr
                 35                  40                  45

Leu Val Leu Leu Ile Ser Trp Asp Ser Arg Leu His Ser Pro Met
                 50                  55                  60

Tyr Tyr Leu Leu Arg Gly Leu Ser Val Ile Asp Met Gly Leu Ser
                 65                  70                  75

Thr Val Thr Leu Pro Gln Leu Leu Ala His Leu Val Ser His Tyr
                 80                  85                  90

Pro Thr Ile Pro Ala Ala Arg Cys Leu Ala Gln Phe Phe Phe Phe
                 95                 100                 105

Tyr Ala Phe Gly Val Thr Asp Thr Leu Val Ile Ala Val Met Ala
                110                 115                 120

Leu Asp Arg Tyr Val Ala Ile Cys Asp Pro Leu His Tyr Ala Leu
                125                 130                 135
```

```
Val Met Asn His Gln Arg Cys Ala Cys Leu Leu Ala Leu Ser Trp
            140                 145                 150

Val Val Ser Ile Leu His Thr Met Leu Arg Val Gly Leu Val Leu
            155                 160                 165

Pro Leu Cys Trp Thr Gly Asp Ala Gly Gly Asn Val Asn Leu Pro
            170                 175                 180

His Phe Phe Cys Asp His Arg Pro Leu Leu Arg Ala Ser Cys Ser
            185                 190                 195

Asp Ile His Ser Asn Glu Leu Ala Ile Phe Phe Glu Gly Gly Phe
            200                 205                 210

Leu Met Leu Gly Pro Cys Ala Leu Ile Val Leu Ser Tyr Val Arg
            215                 220                 225

Ile Gly Ala Ala Ile Leu Arg Leu Pro Ser Ala Ala Gly Arg Arg
            230                 235                 240

Arg Ala Val Ser Thr Cys Gly Ser His Leu Thr Met Val Gly Phe
            245                 250                 255

Leu Tyr Gly Thr Ile Ile Cys Val Tyr Phe Gln Pro Pro Phe Gln
            260                 265                 270

Asn Ser Gln Tyr Gln Asp Met Val Ala Ser Val Met Tyr Thr Ala
            275                 280                 285

Ile Thr Pro Leu Ala Asn Pro Phe Val Tyr Ser Leu His Asn Lys
            290                 295                 300

Asp Val Lys Gly Ala Leu Cys Arg Leu Leu Glu Trp Val Lys Val
            305                 310                 315

Asp Pro

<210> SEQ ID NO 28
<211> LENGTH: 335
<212> TYPE: PRT
<213> ORGANISM: Homo sapiens
<220> FEATURE:
<221> NAME/KEY: misc_feature
<223> OTHER INFORMATION: Incyte ID No: 7472015CD1

<400> SEQUENCE: 28

Met Glu Ser Ser Phe Ser Phe Gly Val Ile Leu Ala Val Leu Ala
 1               5                  10                  15

Ser Leu Ile Ile Ala Thr Asn Thr Leu Val Ala Val Ala Val Leu
            20                  25                  30

Leu Leu Ile His Lys Asn Asp Gly Val Ser Leu Cys Phe Thr Leu
            35                  40                  45

Asn Leu Ala Val Ala Asp Thr Leu Ile Gly Val Ala Ile Ser Gly
            50                  55                  60

Leu Leu Thr Asp Gln Leu Ser Ser Pro Ser Arg Pro Thr Gln Lys
            65                  70                  75

Thr Leu Cys Ser Leu Arg Met Ala Phe Val Thr Ser Ser Ala Ala
            80                  85                  90

Ala Ser Val Leu Thr Val Met Leu Ile Thr Phe Asp Arg Tyr Leu
            95                  100                 105

Ala Ile Lys Gln Pro Phe Arg Tyr Leu Lys Ile Met Ser Gly Phe
            110                 115                 120

Val Ala Gly Ala Cys Ile Ala Gly Leu Trp Leu Val Ser Tyr Leu
            125                 130                 135

Ile Gly Phe Leu Pro Leu Gly Ile Pro Met Phe Gln Gln Thr Ala
            140                 145                 150
```

```
Tyr Lys Gly Gln Cys Ser Phe Ala Val Phe His Pro His Phe
                155                 160                 165

Val Leu Thr Leu Ser Cys Val Gly Phe Pro Ala Met Leu Leu
                170                 175                 180

Phe Val Phe Phe Tyr Cys Asp Met Leu Lys Ile Ala Ser Met His
                185                 190                 195

Ser Gln Gln Ile Arg Lys Met Glu His Ala Gly Ala Met Ala Gly
                200                 205                 210

Gly Tyr Arg Ser Pro Arg Thr Pro Ser Asp Phe Lys Ala Leu Arg
                215                 220                 225

Thr Val Ser Val Leu Ile Gly Ser Phe Ala Leu Ser Trp Thr Pro
                230                 235                 240

Phe Leu Ile Thr Gly Ile Val Gln Val Ala Cys Gln Glu Cys His
                245                 250                 255

Leu Tyr Leu Val Leu Glu Arg Tyr Leu Trp Leu Leu Gly Val Gly
                260                 265                 270

Asn Ser Leu Leu Asn Pro Leu Ile Tyr Ala Tyr Trp Gln Lys Glu
                275                 280                 285

Val Arg Leu Gln Leu Tyr His Met Ala Leu Gly Val Lys Lys Val
                290                 295                 300

Leu Thr Ser Phe Leu Leu Phe Leu Ser Ala Arg Asn Cys Gly Pro
                305                 310                 315

Glu Arg Pro Arg Glu Ser Ser Cys His Ile Val Thr Ile Ser Ser
                320                 325                 330

Ser Glu Phe Asp Gly
                335

<210> SEQ ID NO 29
<211> LENGTH: 309
<212> TYPE: PRT
<213> ORGANISM: Homo sapiens
<220> FEATURE:
<221> NAME/KEY: misc_feature
<223> OTHER INFORMATION: Incyte ID No: 7472016CD1

<400> SEQUENCE: 29

Met Arg Glu Asn Asn Gln Ser Ser Thr Leu Glu Phe Ile Leu Leu
  1               5                  10                  15

Gly Val Thr Gly Gln Gln Gly Gln Glu Asp Phe Phe Tyr Ile Leu
                 20                  25                  30

Phe Leu Phe Ile Tyr Pro Ile Thr Leu Ile Gly Asn Leu Leu Ile
                 35                  40                  45

Val Leu Ala Ile Cys Ser Asp Val Arg Leu His Asn Pro Met Tyr
                 50                  55                  60

Phe Leu Leu Ala Asn Leu Ser Leu Val Asp Ile Phe Phe Ser Ser
                 65                  70                  75

Val Thr Ile Pro Lys Met Leu Ala Asn His Leu Leu Gly Ser Lys
                 80                  85                  90

Ser Ile Ser Phe Gly Gly Cys Leu Thr Gln Met Tyr Phe Met Ile
                 95                 100                 105

Ala Leu Gly Asn Thr Asp Ser Tyr Ile Leu Ala Ala Met Ala Tyr
                110                 115                 120

Asp Arg Ala Val Ala Ile Ser His Pro Leu His Tyr Thr Thr Ile
                125                 130                 135

Met Ser Pro Arg Ser Cys Ile Trp Leu Ile Ala Gly Ser Trp Val
                140                 145                 150
```

```
Ile Gly Asn Ala Asn Ala Leu Pro His Thr Leu Leu Thr Ala Ser
            155                 160                 165

Leu Ser Phe Cys Gly Asn Gln Glu Val Ala Asn Phe Tyr Cys Asp
            170                 175                 180

Ile Thr Pro Leu Leu Lys Leu Ser Cys Ser Asp Ile His Phe His
            185                 190                 195

Val Lys Met Met Tyr Leu Gly Val Gly Ile Phe Ser Val Pro Leu
            200                 205                 210

Leu Cys Ile Ile Val Ser Tyr Ile Arg Val Phe Ser Thr Val Phe
            215                 220                 225

Gln Val Pro Ser Thr Lys Gly Val Leu Lys Ala Phe Ser Thr Cys
            230                 235                 240

Gly Ser His Leu Thr Val Val Ser Leu Tyr Tyr Gly Thr Val Met
            245                 250                 255

Gly Thr Tyr Phe Arg Pro Leu Thr Asn Tyr Ser Leu Lys Asp Ala
            260                 265                 270

Val Ile Thr Val Met Tyr Thr Ala Val Thr Pro Met Leu Asn Pro
            275                 280                 285

Phe Ile Tyr Ser Leu Arg Asn Arg Asp Met Lys Ala Ala Leu Arg
            290                 295                 300

Lys Leu Phe Asn Lys Arg Ile Ser Ser
            305

<210> SEQ ID NO 30
<211> LENGTH: 236
<212> TYPE: PRT
<213> ORGANISM: Homo sapiens
<220> FEATURE:
<221> NAME/KEY: misc_feature
<223> OTHER INFORMATION: Incyte ID No: 7472017CD1

<400> SEQUENCE: 30

Met Gly Met Thr Asn Ser Ser Val Lys Gly Asp Phe Ile Leu Leu
  1               5                  10                  15

Leu Trp Asn Leu Lys Gly Pro Asp Lys Thr Ile Thr Phe Leu Gly
             20                  25                  30

Cys Val Ile Gln Leu Tyr Ile Ser Leu Ala Leu Gly Ser Thr Glu
             35                  40                  45

Cys Val Leu Leu Ala Val Met Ala Phe Asp Arg Tyr Ala Ala Val
             50                  55                  60

Cys Lys Pro Leu His Tyr Thr Ala Val Met Asn Pro Gln Leu Cys
             65                  70                  75

Gln Ala Leu Ala Gly Val Ala Trp Leu Ser Gly Val Gly Asn Thr
             80                  85                  90

Leu Ile Gln Gly Thr Val Thr Leu Trp Leu Pro Arg Cys Gly His
             95                 100                 105

Arg Leu Leu Gln His Phe Phe Leu Ala Cys Val Asp Ile His Asp
            110                 115                 120

Asn Glu Val Gln Leu Phe Val Ala Ser Leu Val Leu Leu Leu Leu
            125                 130                 135

Pro Leu Val Leu Ile Leu Leu Ser Tyr Gly His Ile Ala Lys Val
            140                 145                 150

Val Ile Arg Ile Lys Ser Val Gln Ala Trp Cys Lys Gly Leu Gly
            155                 160                 165

Thr Cys Gly Ser His Leu Ile Val Val Ser Leu Phe Cys Gly Thr
```

```
                          170                 175                 180
Ile Thr Ala Val Tyr Ile Gln Ser Asn Ser Ser Tyr Ala His Ala
                185                 190                 195

His Gly Lys Phe Ile Ser Leu Phe Tyr Thr Val Thr Pro Thr
                200                 205                 210

Leu Asn Pro Leu Ile Tyr Thr Leu Arg Asn Asn Asp Val Lys Gly
                215                 220                 225

Ala Leu Arg Leu Phe Asn Arg Asp Leu Gly Thr
                230                 235

<210> SEQ ID NO 31
<211> LENGTH: 363
<212> TYPE: PRT
<213> ORGANISM: Homo sapiens
<220> FEATURE:
<221> NAME/KEY: misc_feature
<223> OTHER INFORMATION: Incyte ID No: 7472018CD1

<400> SEQUENCE: 31

Met Gly Pro Gly Glu Ala Leu Leu Ala Gly Leu Leu Val Met Val
  1               5                  10                  15

Leu Ala Val Ala Leu Leu Ser Asn Ala Leu Val Leu Leu Cys Cys
                 20                  25                  30

Ala Tyr Ser Ala Glu Leu Arg Thr Arg Ala Ser Gly Val Leu Leu
                 35                  40                  45

Val Asn Leu Ser Leu Gly His Leu Leu Leu Ala Ala Leu Asp Met
                 50                  55                  60

Pro Phe Thr Leu Leu Gly Val Met Arg Gly Arg Thr Pro Ser Ala
                 65                  70                  75

Pro Gly Ala Cys Gln Val Ile Gly Phe Leu Asp Thr Phe Leu Ala
                 80                  85                  90

Ser Asn Ala Ala Leu Ser Val Ala Ala Leu Ser Ala Asp Gln Trp
                 95                 100                 105

Leu Ala Val Gly Phe Pro Leu Arg Tyr Ala Gly Arg Leu Arg Pro
                110                 115                 120

Arg Tyr Ala Gly Leu Leu Leu Gly Cys Ala Trp Gly Gln Ser Leu
                125                 130                 135

Ala Phe Ser Gly Ala Ala Leu Gly Cys Ser Trp Leu Gly Tyr Ser
                140                 145                 150

Ser Ala Phe Ala Ser Cys Ser Leu Arg Leu Pro Pro Glu Pro Glu
                155                 160                 165

Arg Pro Arg Phe Ala Ala Phe Thr Ala Thr Leu His Ala Val Gly
                170                 175                 180

Phe Val Leu Pro Leu Ala Val Leu Cys Leu Thr Ser Leu Gln Val
                185                 190                 195

His Arg Val Ala Arg Arg His Cys Gln Arg Met Asp Thr Val Thr
                200                 205                 210

Met Lys Ala Leu Ala Leu Leu Ala Asp Leu His Pro Ser Val Arg
                215                 220                 225

Gln Arg Cys Leu Ile Gln Gln Lys Arg Arg His Arg Ala Thr
                230                 235                 240

Arg Lys Ile Gly Ile Ala Ile Ala Thr Phe Leu Ile Cys Phe Ala
                245                 250                 255

Pro Tyr Val Met Thr Arg Leu Ala Glu Leu Val Pro Phe Val Thr
                260                 265                 270
```

-continued

```
Val Asn Ala Gln Trp Gly Ile Leu Ser Lys Cys Leu Thr Tyr Ser
            275                 280                 285

Lys Ala Val Ala Asp Pro Phe Thr Tyr Ser Leu Leu Arg Arg Pro
            290                 295                 300

Phe Arg Gln Val Leu Ala Gly Met Val His Arg Leu Leu Lys Arg
            305                 310                 315

Thr Pro Arg Pro Ala Ser Thr His Asp Ser Ser Leu Asp Val Ala
            320                 325                 330

Gly Met Val His Gln Leu Leu Lys Arg Thr Pro Arg Pro Ala Ser
            335                 340                 345

Thr His Asn Gly Ser Val Asp Thr Glu Asn Asp Ser Cys Leu Gln
            350                 355                 360

Gln Thr His

<210> SEQ ID NO 32
<211> LENGTH: 308
<212> TYPE: PRT
<213> ORGANISM: Homo sapiens
<220> FEATURE:
<221> NAME/KEY: misc_feature
<223> OTHER INFORMATION: Incyte ID No: 7472019CD1

<400> SEQUENCE: 32

Met Ala Met Asp Asn Val Thr Ala Val Phe Gln Phe Leu Leu Ile
  1               5                  10                  15

Gly Ile Ser Asn Tyr Pro Gln Trp Arg Asp Thr Phe Phe Thr Leu
             20                  25                  30

Val Leu Ile Ile Tyr Leu Ser Thr Leu Leu Gly Asn Gly Phe Met
             35                  40                  45

Ile Phe Leu Ile His Phe Asp Pro Asn Leu His Thr Pro Ile Tyr
             50                  55                  60

Phe Phe Leu Ser Asn Leu Ser Phe Leu Asp Leu Cys Tyr Gly Thr
             65                  70                  75

Ala Ser Met Pro Gln Ala Leu Val His Cys Phe Ser Thr His Pro
             80                  85                  90

Tyr Leu Ser Tyr Pro Arg Cys Leu Ala Gln Thr Ser Val Ser Leu
             95                 100                 105

Ala Leu Ala Thr Ala Glu Cys Leu Leu Leu Ala Ala Met Ala Tyr
            110                 115                 120

Asp Arg Val Val Ala Ile Ser Asn Pro Leu Arg Tyr Ser Val Val
            125                 130                 135

Met Asn Gly Pro Val Cys Val Cys Leu Val Ala Thr Ser Trp Gly
            140                 145                 150

Thr Ser Leu Val Leu Thr Ala Met Leu Ile Leu Ser Leu Arg Leu
            155                 160                 165

His Phe Cys Gly Ala Asn Val Ile Asn His Phe Ala Cys Glu Ile
            170                 175                 180

Leu Ser Leu Ile Lys Leu Thr Cys Ser Asp Thr Ser Leu Asn Glu
            185                 190                 195

Phe Met Ile Leu Ile Thr Ser Ile Phe Thr Leu Leu Leu Pro Phe
            200                 205                 210

Gly Phe Val Leu Leu Ser Tyr Ile Arg Ile Ala Met Ala Ile Ile
            215                 220                 225

Arg Ile Arg Ser Leu Gln Gly Arg Leu Lys Ala Phe Thr Thr Cys
            230                 235                 240
```

```
Gly Ser His Leu Thr Val Val Thr Ile Phe Tyr Gly Ser Ala Ile
            245                 250                 255

Ser Met Tyr Met Lys Thr Gln Ser Lys Ser Tyr Pro Asp Gln Asp
            260                 265                 270

Lys Phe Ile Ser Val Phe Tyr Gly Ala Leu Thr Pro Met Leu Asn
            275                 280                 285

Pro Leu Ile Tyr Ser Leu Arg Lys Lys Asp Val Lys Arg Ala Ile
            290                 295                 300

Arg Lys Val Met Leu Lys Arg Thr
            305

<210> SEQ ID NO 33
<211> LENGTH: 343
<212> TYPE: PRT
<213> ORGANISM: Homo sapiens
<220> FEATURE:
<221> NAME/KEY: misc_feature
<223> OTHER INFORMATION: Incyte ID No: 7472021CD1

<400> SEQUENCE: 33

Met His Phe Leu Pro Thr Val Phe Gly Phe Leu Asn Arg Val Thr
  1               5                  10                  15

Leu Gly Ile Phe Arg Glu Thr Met Val Asn Leu Thr Ser Met Ser
             20                  25                  30

Gly Phe Leu Leu Met Gly Phe Ser Asp Glu Arg Lys Leu Gln Ile
             35                  40                  45

Leu His Ala Leu Val Phe Leu Val Thr Tyr Leu Leu Ala Leu Thr
             50                  55                  60

Gly Asn Leu Leu Ile Ile Thr Ile Ile Thr Val Asp Arg Arg Leu
             65                  70                  75

His Ser Pro Met Tyr Tyr Phe Leu Lys His Leu Ser Leu Leu Asp
             80                  85                  90

Leu Cys Phe Ile Ser Val Thr Val Pro Gln Ser Ile Ala Asn Ser
             95                 100                 105

Leu Met Gly Asn Gly Tyr Ile Ser Leu Val Gln Cys Ile Leu Gln
            110                 115                 120

Val Phe Phe Phe Ile Ala Leu Ala Ser Ser Glu Val Ala Ile Leu
            125                 130                 135

Thr Val Met Ser Tyr Asp Arg Tyr Ala Ala Ile Cys Gln Pro Leu
            140                 145                 150

His Tyr Glu Thr Ile Met Asp Pro Arg Ala Cys Arg His Ala Val
            155                 160                 165

Ile Ala Val Trp Ile Ala Gly Gly Leu Ser Gly Leu Met His Ala
            170                 175                 180

Ala Ile Asn Phe Ser Ile Pro Leu Cys Gly Lys Arg Val Ile His
            185                 190                 195

Gln Phe Phe Cys Asp Val Pro Gln Met Leu Lys Leu Ala Cys Ser
            200                 205                 210

Tyr Glu Phe Ile Asn Glu Ile Ala Leu Ala Ala Phe Thr Thr Ser
            215                 220                 225

Ala Ala Phe Ile Cys Leu Ile Ser Ile Val Leu Ser Tyr Ile Arg
            230                 235                 240

Ile Phe Ser Thr Val Leu Arg Ile Pro Ser Ala Glu Gly Arg Thr
            245                 250                 255

Lys Val Phe Ser Thr Cys Leu Pro His Leu Phe Val Ala Thr Phe
            260                 265                 270
```

```
Phe Leu Ser Ala Ala Gly Phe Glu Phe Leu Arg Leu Pro Ser Asp
                275                 280                 285

Ser Ser Ser Thr Val Asp Leu Val Phe Ser Val Phe Tyr Thr Val
                290                 295                 300

Ile Pro Pro Thr Leu Asn Pro Val Ile Tyr Ser Leu Arg Asn Asp
                305                 310                 315

Ser Met Lys Ala Ala Leu Arg Lys Met Leu Ser Lys Glu Glu Leu
                320                 325                 330

Pro Gln Arg Lys Met Cys Leu Lys Ala Met Phe Lys Leu
                335                 340

<210> SEQ ID NO 34
<211> LENGTH: 323
<212> TYPE: PRT
<213> ORGANISM: Homo sapiens
<220> FEATURE:
<221> NAME/KEY: misc_feature
<223> OTHER INFORMATION: Incyte ID No: 7472009CD1

<400> SEQUENCE: 34

Met Trp Gln Lys Asn Gln Thr Ser Leu Ala Asp Phe Ile Leu Glu
  1               5                  10                  15

Gly Leu Phe Asp Asp Ser Leu Thr His Leu Phe Leu Phe Ser Leu
                 20                  25                  30

Thr Met Val Val Phe Leu Ile Ala Val Ser Gly Asn Thr Leu Thr
                 35                  40                  45

Ile Leu Leu Ile Cys Ile Asp Pro Gln Leu His Thr Pro Met Tyr
                 50                  55                  60

Phe Leu Leu Ser Gln Leu Ser Leu Met Asp Leu Met His Val Ser
                 65                  70                  75

Thr Thr Ile Leu Lys Met Ala Thr Asn Tyr Leu Ser Gly Lys Lys
                 80                  85                  90

Ser Ile Ser Phe Val Gly Cys Ala Thr Gln His Phe Leu Tyr Leu
                 95                 100                 105

Cys Leu Gly Gly Ala Glu Cys Phe Leu Leu Ala Val Met Ser Tyr
                110                 115                 120

Asp Arg Tyr Val Ala Ile Cys His Pro Leu Arg Tyr Ala Val Leu
                125                 130                 135

Met Asn Lys Lys Val Gly Leu Met Met Ala Val Met Ser Trp Leu
                140                 145                 150

Gly Ala Ser Val Asn Ser Leu Ile His Met Ala Ile Leu Met His
                155                 160                 165

Phe Pro Phe Cys Gly Pro Arg Lys Val Tyr His Phe Tyr Cys Glu
                170                 175                 180

Phe Pro Ala Val Val Lys Leu Val Cys Gly Asp Ile Thr Val Tyr
                185                 190                 195

Glu Thr Thr Val Tyr Ile Ser Ser Ile Leu Leu Leu Leu Pro Ile
                200                 205                 210

Phe Leu Ile Ser Thr Ser Tyr Val Phe Ile Leu Gln Ser Val Ile
                215                 220                 225

Gln Met Arg Ser Ser Gly Ser Lys Arg Asn Ala Phe Ala Thr Cys
                230                 235                 240

Gly Ser His Leu Thr Val Val Ser Leu Trp Phe Gly Ala Cys Ile
                245                 250                 255

Phe Ser Tyr Met Arg Pro Arg Ser Gln Cys Thr Leu Leu Gln Asn
```

```
                    260                 265                 270
Lys Val Gly Ser Val Phe Tyr Ser Ile Ile Thr Pro Thr Leu Asn
                275                 280                 285

Ser Leu Ile Tyr Thr Leu Arg Asn Lys Asp Val Ala Lys Ala Leu
            290                 295                 300

Arg Arg Val Leu Arg Arg Asp Val Ile Thr Gln Cys Ile Gln Arg
        305                 310                 315

Leu Gln Leu Trp Leu Pro Arg Val
            320

<210> SEQ ID NO 35
<211> LENGTH: 299
<212> TYPE: PRT
<213> ORGANISM: Homo sapiens
<220> FEATURE:
<221> NAME/KEY: misc_feature
<223> OTHER INFORMATION: Incyte ID No: 7472010CD1

<400> SEQUENCE: 35

Met Glu Leu Glu Gly Asp Phe Leu Gly Ser Val Gly Glu Leu Gly
  1               5                  10                  15

Gln Val Ile Gln Thr Cys Ser Gly Ile Tyr Val Phe Thr Val Val
                 20                  25                  30

Gly Asn Leu Gly Leu Ile Thr Leu Ile Gly Ile Asn Pro Ser Leu
             35                  40                  45

His Thr Pro Met Tyr Phe Phe Leu Phe Asn Leu Ser Phe Ile Asp
         50                  55                  60

Leu Cys Tyr Ser Cys Val Phe Thr Pro Lys Met Leu Asn Asp Phe
     65                  70                  75

Val Ser Glu Ser Ile Ile Ser Tyr Val Gly Cys Met Thr Gln Leu
 80                  85                  90

Phe Phe Phe Cys Phe Phe Val Asn Ser Glu Cys Tyr Val Leu Val
                 95                 100                 105

Ser Met Ala Tyr Asp Arg Tyr Val Ala Ile Cys Asn Pro Leu Leu
            110                 115                 120

Tyr Met Val Thr Met Ser Pro Arg Val Cys Phe Leu Leu Met Phe
        125                 130                 135

Gly Ser Tyr Val Val Gly Phe Ala Gly Ala Met Ala His Thr Gly
    140                 145                 150

Ser Met Leu Arg Leu Thr Phe Cys Asp Ser Asn Val Ile Asp His
            155                 160                 165

Tyr Leu Cys Asp Val Leu Pro Leu Leu Gln Leu Ser Cys Thr Ser
        170                 175                 180

Thr His Val Ser Glu Leu Val Phe Phe Ile Val Val Gly Val Ile
    185                 190                 195

Thr Met Leu Ser Ser Ile Ser Ile Val Ile Ser Tyr Ala Leu Ile
            200                 205                 210

Leu Ser Asn Ile Leu Cys Ile Pro Ser Ala Glu Gly Arg Ser Lys
        215                 220                 225

Ala Phe Ser Thr Trp Gly Ser His Ile Ile Ala Val Ala Leu Phe
    230                 235                 240

Phe Gly Ser Gly Thr Phe Thr Tyr Leu Thr Thr Ser Phe Pro Gly
            245                 250                 255

Ser Met Asn His Gly Arg Phe Ala Ser Val Phe Tyr Thr Asn Val
        260                 265                 270
```

```
Val Pro Met Leu Asn Pro Ser Ile Tyr Ser Leu Arg Asn Lys Asp
            275                 280                 285

Asp Lys Leu Ala Leu Gly Lys Thr Leu Lys Arg Val Leu Phe
            290                 295
```

<210> SEQ ID NO 36
<211> LENGTH: 307
<212> TYPE: PRT
<213> ORGANISM: Homo sapiens
<220> FEATURE:
<221> NAME/KEY: misc_feature
<223> OTHER INFORMATION: Incyte ID No: 7472011CD1

<400> SEQUENCE: 36

```
Met Glu Thr Gly Asn Leu Thr Trp Val Ser Asp Phe Val Phe Leu
  1               5                  10                  15

Gly Leu Ser Gln Thr Arg Glu Leu Gln Arg Phe Leu Phe Leu Met
             20                  25                  30

Phe Leu Phe Val Tyr Ile Thr Thr Val Met Gly Asn Ile Leu Ile
             35                  40                  45

Ile Ile Thr Val Thr Ser Asp Ser Gln Leu His Thr Pro Met Tyr
             50                  55                  60

Phe Leu Leu Arg Asn Leu Ala Val Leu Asp Leu Cys Phe Ser Ser
             65                  70                  75

Val Thr Ala Pro Lys Met Leu Val Asp Leu Leu Ser Glu Lys Lys
             80                  85                  90

Thr Ile Ser Tyr Gln Gly Cys Met Gly Gln Ile Phe Phe Phe His
             95                 100                 105

Phe Leu Gly Gly Ala Met Val Phe Phe Leu Ser Val Met Ala Phe
            110                 115                 120

Asp Arg Leu Ile Ala Ile Ser Arg Pro Leu Arg Tyr Val Thr Val
            125                 130                 135

Met Asn Thr Gln Leu Trp Val Gly Leu Val Val Ala Thr Trp Val
            140                 145                 150

Gly Gly Phe Val His Ser Ile Val Gln Leu Ala Leu Met Leu Pro
            155                 160                 165

Leu Pro Phe Cys Gly Pro Asn Ile Leu Asp Asn Phe Tyr Cys Asp
            170                 175                 180

Val Pro Gln Val Leu Arg Leu Ala Cys Thr Asp Thr Ser Leu Leu
            185                 190                 195

Glu Phe Leu Lys Ile Ser Asn Ser Gly Leu Leu Asp Val Val Trp
            200                 205                 210

Phe Phe Leu Leu Leu Met Ser Tyr Leu Phe Ile Leu Val Met Leu
            215                 220                 225

Arg Ser His Pro Gly Glu Ala Arg Arg Lys Ala Ala Ser Thr Cys
            230                 235                 240

Thr Thr His Ile Ile Val Val Ser Met Ile Phe Val Pro Ser Ile
            245                 250                 255

Tyr Leu Tyr Ala Arg Pro Phe Thr Pro Phe Pro Met Asp Lys Leu
            260                 265                 270

Val Ser Ile Gly His Thr Val Met Thr Pro Met Leu Asn Pro Met
            275                 280                 285

Ile Tyr Thr Leu Arg Asn Gln Asp Met Gln Ala Ala Val Arg Arg
            290                 295                 300

Leu Gly Arg His Arg Leu Val
            305
```

```
<210> SEQ ID NO 37
<211> LENGTH: 314
<212> TYPE: PRT
<213> ORGANISM: Homo sapiens
<220> FEATURE:
<221> NAME/KEY: misc_feature
<223> OTHER INFORMATION: Incyte ID No: 7472012CD1

<400> SEQUENCE: 37

Met Asp Asn Ser Asn Trp Thr Ser Val Ser His Phe Val Leu Leu
 1               5                  10                  15

Gly Ile Ser Thr His Pro Glu Glu Gln Ile Pro Leu Phe Leu Val
                20                  25                  30

Phe Ser Leu Met Tyr Ala Ile Asn Ile Ser Gly Asn Leu Ala Ile
                35                  40                  45

Ile Thr Leu Ile Leu Ser Ala Pro Arg Leu His Ile Pro Met Tyr
                50                  55                  60

Ile Phe Leu Ser Asn Leu Ala Leu Thr Asp Ile Cys Phe Thr Ser
                65                  70                  75

Thr Thr Val Pro Lys Met Leu Gln Ile Ile Phe Ser Pro Thr Lys
                80                  85                  90

Val Ile Ser Tyr Thr Gly Cys Leu Ala Gln Thr Tyr Phe Phe Ile
                95                 100                 105

Cys Phe Ala Val Met Glu Asn Phe Ile Leu Ala Val Met Ala Tyr
               110                 115                 120

Asp Arg Tyr Ile Ala Ile Cys His Pro Phe His Tyr Thr Met Ile
               125                 130                 135

Leu Thr Arg Met Leu Cys Val Lys Met Val Met Cys His Ala
               140                 145                 150

Leu Ser His Leu His Ala Met Leu His Thr Phe Leu Ile Gly Gln
               155                 160                 165

Leu Ile Phe Cys Ala Asp Asn Arg Ile Pro His Phe Cys Asp
               170                 175                 180

Leu Tyr Ala Leu Met Lys Ile Ser Cys Thr Ser Thr Tyr Leu Asn
               185                 190                 195

Thr Leu Met Ile His Thr Glu Gly Ala Val Val Ile Ser Gly Ala
               200                 205                 210

Leu Ala Phe Ile Thr Ala Ser Tyr Ala Cys Ile Ile Leu Val Val
               215                 220                 225

Leu Arg Ile Pro Ser Ala Lys Gly Arg Trp Lys Thr Phe Ser Thr
               230                 235                 240

Cys Gly Ser His Leu Thr Val Val Ala Ile Phe Tyr Gly Thr Leu
               245                 250                 255

Ser Trp Val Tyr Phe Arg Pro Leu Ser Ser Tyr Ser Val Thr Lys
               260                 265                 270

Gly Arg Ile Ile Thr Val Val Tyr Thr Val Thr Pro Met Leu
               275                 280                 285

Asn Pro Phe Ile Tyr Ser Leu Arg Asn Gly Asp Val Lys Gly Gly
               290                 295                 300

Phe Met Lys Trp Met Ser Arg Met Gln Thr Phe Phe Arg
               305                 310

<210> SEQ ID NO 38
<211> LENGTH: 310
<212> TYPE: PRT
```

```
<213> ORGANISM: Homo sapiens
<220> FEATURE:
<221> NAME/KEY: misc_feature
<223> OTHER INFORMATION: Incyte ID No: 7472014CD1

<400> SEQUENCE: 38
```

| | | | | | | | | | | | | | | |
|---|---|---|---|---|---|---|---|---|---|---|---|---|---|---|
| Met | Gly | Arg | Asn | Asn | Leu | Thr | Arg | Pro | Ser | Glu | Phe | Ile | Leu | Leu |
| 1 | | | | 5 | | | | | 10 | | | | | 15 |
| Gly | Leu | Ser | Ser | Arg | Pro | Glu | Asp | Gln | Lys | Pro | Leu | Phe | Ala | Val |
| | | | | 20 | | | | | 25 | | | | | 30 |
| Phe | Leu | Pro | Ile | Tyr | Leu | Ile | Thr | Val | Ile | Gly | Asn | Leu | Leu | Ile |
| | | | | 35 | | | | | 40 | | | | | 45 |
| Ile | Leu | Ala | Ile | Arg | Ser | Asp | Thr | Arg | Leu | Gln | Thr | Pro | Met | Tyr |
| | | | | 50 | | | | | 55 | | | | | 60 |
| Phe | Phe | Leu | Ser | Ile | Leu | Ser | Phe | Val | Asp | Ile | Cys | Tyr | Val | Thr |
| 65 | | | | | 70 | | | | | 75 | | | | |
| Val | Ile | Ile | Pro | Lys | Met | Leu | Val | Asn | Phe | Leu | Ser | Glu | Thr | Lys |
| | | | | 80 | | | | | 85 | | | | | 90 |
| Thr | Ile | Ser | Tyr | Gly | Glu | Cys | Leu | Thr | Gln | Met | Tyr | Phe | Phe | Leu |
| | | | | 95 | | | | | 100 | | | | | 105 |
| Ala | Phe | Gly | Asn | Thr | Asp | Ser | Tyr | Leu | Leu | Ala | Ala | Met | Ala | Ile |
| | | | | 110 | | | | | 115 | | | | | 120 |
| Asp | Arg | Tyr | Val | Ala | Ile | Cys | Asn | Pro | Phe | His | Tyr | Ile | Thr | Ile |
| | | | | 125 | | | | | 130 | | | | | 135 |
| Met | Ser | His | Arg | Cys | Cys | Val | Leu | Leu | Val | Leu | Ser | Phe | Cys |
| | | | | 140 | | | | | 145 | | | | | 150 |
| Ile | Pro | His | Phe | His | Ser | Leu | Leu | His | Ile | Leu | Leu | Thr | Asn | Gln |
| | | | | 155 | | | | | 160 | | | | | 165 |
| Leu | Ile | Phe | Cys | Ala | Ser | Asn | Val | Ile | His | His | Phe | Phe | Cys | Asp |
| | | | | 170 | | | | | 175 | | | | | 180 |
| Asp | Gln | Pro | Val | Leu | Lys | Leu | Ser | Cys | Ser | Ser | His | Phe | Val | Lys |
| | | | | 185 | | | | | 190 | | | | | 195 |
| Glu | Ile | Thr | Val | Met | Thr | Glu | Gly | Leu | Ala | Val | Ile | Met | Thr | Pro |
| | | | | 200 | | | | | 205 | | | | | 210 |
| Phe | Ser | Cys | Ile | Ile | Ile | Ser | Tyr | Leu | Arg | Ile | Leu | Ile | Thr | Val |
| | | | | 215 | | | | | 220 | | | | | 225 |
| Leu | Lys | Ile | Pro | Ser | Ala | Ala | Gly | Lys | Arg | Lys | Ala | Phe | Ser | Thr |
| | | | | 230 | | | | | 235 | | | | | 240 |
| Cys | Gly | Ser | His | Leu | Thr | Val | Val | Thr | Leu | Phe | Tyr | Gly | Ser | Ile |
| | | | | 245 | | | | | 250 | | | | | 255 |
| Ser | Tyr | Val | Tyr | Phe | Gln | Pro | Leu | Ser | Asn | Tyr | Thr | Val | Lys | Asp |
| | | | | 260 | | | | | 265 | | | | | 270 |
| Gln | Ile | Ala | Thr | Ile | Ile | Tyr | Thr | Val | Leu | Thr | Pro | Met | Leu | Asn |
| | | | | 275 | | | | | 280 | | | | | 285 |
| Pro | Phe | Ile | Tyr | Ser | Leu | Arg | Asn | Lys | Asp | Met | Lys | Gln | Gly | Leu |
| | | | | 290 | | | | | 295 | | | | | 300 |
| Ala | Lys | Leu | Met | His | Arg | Met | Lys | Cys | Gln |
| | | | | 305 | | | | | 310 |

```
<210> SEQ ID NO 39
<211> LENGTH: 359
<212> TYPE: PRT
<213> ORGANISM: Homo sapiens
<220> FEATURE:
<221> NAME/KEY: misc_feature
<223> OTHER INFORMATION: Incyte ID No: 7472020CD1
```

-continued

```
<400> SEQUENCE: 39

Met Phe Lys Ala Ile Leu Gly His Val Trp Pro Lys Asp His Gly
1               5                   10                  15

Leu Asp Lys Leu Val Val Arg Cys Pro Arg His Thr Glu Pro Trp
                20                  25                  30

Asn Leu Thr Gly Ile Ser Glu Phe Leu Leu Leu Gly Leu Ser Glu
                35                  40                  45

Asp Pro Glu Leu Gln Pro Val Leu Pro Gly Leu Ser Leu Ser Met
                50                  55                  60

Tyr Leu Val Thr Val Leu Arg Asn Leu Leu Ile Ile Leu Ala Val
                65                  70                  75

Ser Ser Asp Ser His Leu His Thr Pro Met Cys Phe Phe Leu Ser
                80                  85                  90

Asn Leu Cys Trp Ala Asp Ile Gly Phe Thr Ser Ala Met Val Pro
                95                  100                 105

Lys Met Ile Val Asp Met Gln Ser His Ser Arg Val Ile Ser Tyr
                110                 115                 120

Ala Gly Cys Leu Thr Gln Met Ser Phe Val Leu Phe Ala Cys
                125                 130                 135

Ile Glu Asp Met Leu Leu Thr Val Met Ala Tyr Asp Arg Phe Val
                140                 145                 150

Ala Ile Cys His Pro Leu His Tyr Pro Val Ile Met Asn Pro His
                155                 160                 165

Leu Gly Val Phe Leu Val Leu Val Ser Phe Phe Leu Ser Leu Leu
                170                 175                 180

Asp Ser Gln Leu His Ser Trp Ile Val Leu Gln Phe Thr Phe Phe
                185                 190                 195

Lys Asn Val Glu Ile Ser Asn Phe Val Cys Asp Pro Ser Gln Leu
                200                 205                 210

Leu Asn Leu Ala Cys Ser Asp Ser Val Ile Asn Ser Ile Phe Ile
                215                 220                 225

Tyr Leu Asp Ser Ile Met Phe Gly Phe Leu Pro Ile Ser Gly Ile
                230                 235                 240

Leu Leu Ser Tyr Ala Asn Asn Val Pro Ser Ile Leu Arg Ile Ser
                245                 250                 255

Ser Ser Asp Arg Lys Ser Lys Ala Phe Ser Thr Cys Gly Ser His
                260                 265                 270

Leu Ala Val Val Cys Leu Phe Tyr Gly Thr Gly Ile Gly Val Tyr
                275                 280                 285

Leu Thr Ser Ala Val Ser Pro Pro Arg Asn Gly Val Val Ala
                290                 295                 300

Ser Val Met Tyr Ala Val Val Thr Pro Met Leu Asn Pro Phe Ile
                305                 310                 315

Tyr Ser Leu Arg Asn Arg Asp Ile Gln Ser Ala Leu Trp Arg Leu
                320                 325                 330

Arg Ser Arg Thr Val Glu Ser His Asp Leu Leu Ser Gln Asp Leu
                335                 340                 345

Leu His Pro Phe Ser Cys Val Gly Glu Lys Gly Gln Pro His
                350                 355

<210> SEQ ID NO 40
<211> LENGTH: 936
<212> TYPE: DNA
<213> ORGANISM: Homo sapiens
```

```
<220> FEATURE:
<221> NAME/KEY: misc_feature
<223> OTHER INFORMATION: Incyte ID No: 104941CB1

<400> SEQUENCE: 40
atggagataa agaactacag cagcagcacc tcaggcttca tcctcctggg cctctcttcc      60
aaccctcagc tgcagaaacc tctctttgcc atcttcctca tcatgtacct gctcgctgcg     120
gtggggaatg tgctcatcat cccggccatc tactctgacc ccaggctcca caccccatg     180 tacttttttc tcagcaactt gtctttcatg gatatctgct tcacaacagt catagtgcct     240
aagatgctgg tgaattttct atcagagaca aaggttatct cctatgtggg ctgcctggcc     300
cagatgtact tctttatggc atttgggaac actgacagct acctgctggc ctctatggcc     360
atcgaccggc tggtggccat ctgcaacccc ttacactatg atgtggttat gaaaccacgg     420
cattgcctgc tcatgctatt gggttcttgc agcatctccc acctacattc cctgttccgc     480
gtgctactta tgtctcgctt gtcttcctgt gcctctcaca tcattaagca cttttttctgt   540 gacacccagc ctgtgctaaa gctctcctgc tctgacacat cctccagcca gatggtggtg     600
atgactgaga cctagctgt cattgtgacc cccttcctgt gtatcatctt ctcctacctg     660
cgaatcatgg tcactgtgct cagaatcccc tctgcagccg ggaagtggaa ggccttctct     720
acctgtggct cccacctcac tgcagtagcc ctttttctatg ggagtattat ttatgtctat   780
tttaggcccc tgtccatgta ctcagtggtt agggaccggg tagccacagt tatgtacaca    840
gtagtgacac ccatgctgaa ccctttcatc tacagcctga ggaacaaaga tatgaagagg     900
ggtttgaaga aattacagga cagaatttac cggtaa                               936

<210> SEQ ID NO 41
<211> LENGTH: 3365
<212> TYPE: DNA
<213> ORGANISM: Homo sapiens
<220> FEATURE:
<221> NAME/KEY: misc_feature
<223> OTHER INFORMATION: Incyte ID No: 1499408CB1

<400> SEQUENCE: 41
atggaccagc cagaggcccc ctgctccagc acggggccgc gcctcgcggt ggcccgcgag      60
ctgctcctgg ctgcgctgga ggaactgagc caagagcagc tgaagcgctt ccgccacaag    120
ctgcgcgacg tgggcccgga cggacgcagc atcccgtggg ggcggctgga gcgcgcggac    180
gccgtggacc tcgcggagca gctggcccag ttctacggcc cggagcctgc cctggaggtg    240
gcccgcaaga ccctcaagag gcggacgcg cgcgacgtgg cggcgcagct ccaggagcgg    300
cggctgcagc ggctcgggct cggctccggg acgctgctct ccgtgtccga gtacaagaag    360
aagtaccggg agcacgtgct gcagctgcac gctcgggtga aggagaggaa cgcccgctcc    420
gtgaagatca ccaagcgctt caccaagctg ctcatcgcgc ccgagagcgc cgccccggag    480
gaggcgctgg ggcccgcgga agagcctgag ccggggcgcg cgcggcgctc ggacacgcac    540
actttcaacc gcctcttccg ccgcgacgag gagggccggc ggccgctgac cgtggtgctg    600
cagggcccgg cgggcatcgg caagaccatg gcggccaaaa agatcctgta cgactgggcg    660
gcgggcaagc tgtaccaggg ccaggtggac ttcgccttct tcatgcccct cggcgagctg    720
ctggagaggc cgggcacgcg cagcctggct gacctgatcc tggaccagtg ccccgaccgc    780
ggcgcgccgg tgccgcagat gctgcccag ccgcagcggc tgctcttcat cctggacggc    840
gcggacgagc tgccggcgct ggggggcccc gaggccgcgc cctgcacaga ccccttcgag    900
```

```
gcggcgagcg gcgcgcgggt gctaggcggg ctgctgagca aggcgctgct gcccacggcc      960
ctcctgctgg tgaccacgcg cgccgccgcc cccggggagc tgcagggccg cctgtgttcc     1020
ccgcagtgcg ccgaggtgcg cggcttctcc gacaaggaca agaagaagta tttctacaag     1080
ttcttccggg atgagaggag ggccgagcgc gcctaccgct tcgtgaagga gaacgagacg     1140
ctgttcgcgc tgtgcttcgt gcccttcgtg tgctggatcg tgtgcaccgt gctgcgccag     1200
cagctggagc tcggtcggga cctgtcgcgc acgtccaaga ccaccacgtc agtgtacctg     1260
cttttcatca ccagcgttct gagctcggct ccggtagccg acgggccccg gttgcagggc     1320
gacctgcgca atctgtgccg cctggcccgc gagggcgtcc tcgacgcag gcgcagttt      1380
gccgagaagg aactggagca actggagctt cgtggctcca aagtgcagac gctgtttctc     1440
agcaaaaagg agctgccggg cgtgctggag acagaggtca cctaccagtt catcgaccag     1500
agcttccagg agttcctcgc ggcactgtcc tacctgctgg aggacggcgg ggtgcccagg     1560
accgcggctg gcgcgttgg gacactcctg cgtggggacg cccagccgca cagccacttg      1620
gtgctcacca cgcgcttcct cttcggactg ctgagcgcgg agcggatgcg cgacatcgag     1680
cgccacttcg gctgcatggt ttcagagcgt gtgaagcagg aggccctgcg gtgggtgcag     1740
ggacagggac agggctgccc cggagtggca ccagaggtga ccgaggggc caaagggctc      1800
gaggacaccg aagagccaga ggaggaggag gaggagagg agcccaacta cccactggag      1860
ttgctgtact gcctgtacga gacgcaggag gacgcgtttg tgcgccaagc cctgtgccgg     1920
ttcccggagc tggcgctgca gcgagtgcgc ttctgccgca tggacgtggc tgttctgagc     1980
tactgcgtga ggtgctgccc tgctggacag gcactgcggc tgatcagctg cagattggtt     2040
gctgcgcaga agaagaagaa gaagagcctg gggaagcggc tccaggccag cctgggtggc     2100
ggcagttctc aaggcaccac aaaacaactg ccagcctccc ttcttcatcc actctttcag     2160
gcaatgactg acccactgtg ccatctgagc agcctcacgc tgtcccactg caaactccct     2220
gacgcggtct gccgagacct ttctgaggcc ctagggcag cccccgcact gacggagctg      2280
ggcctcctcc acaacaggct cagtgaggcg ggactgcgta tgctgagtga gggcctagcc     2340
tggccgcagt gcagggtgca gacggtcagg gtacagctgc ctgacccca gcgagggctc      2400
cagtacctgg tgggtatgct tcggcagagc cccgccctga ccaccctgga tctcagcggc     2460
tgccaactgc ccgcccccat ggtgacctac ctgtgtgcag cctgcagca ccagggatgc      2520
ggcctgcaga ccctcagtct ggcctctgtg gagctgagcg agcagtcact acaggagctt     2580
caggctgtga agagagcaaa gccggatctg gtcatcacac acccagcgct ggacggccac     2640
ccacaacctc ccaaggaact catctcgacc ttctgaggct ctggtggcca gagcagggtg     2700
gaagacccta gtcaaagtcc ctgtggagag aacggcccat tccaagggca ggaggatatt     2760
gctctcggcc tttgggaaac ttttgagccg agaggccgca gacaggcatg tgggaggccc     2820
agacacggca ccctgccccg tccaggacag gcccaggacc tgcccctctc tccacacctg     2880
gggtaccccctt ctccccccag ccccaccact actccaccca ccttcctctc ctgagaccct    2940
ccagccattc cccttgaaaa cacccccga ccccaagcca caataatgac agcgagagct      3000
ccaattaact aagcacctac ctgggggcag aataacccctt cactgcctga tccccatctg    3060
cagtgtggcc caacagcccc cagaactatg cccacataga ctggaggtag gcagttcacc     3120
gtccctccct gttaggaatg agaccatccc tgaggctatg gcccaggccc acaggcgtcc     3180
agtgtctgag atctttggga agggagacta gggcaggtgg agacagcgca gaaccccgt      3240
gctgggtggg aagcatgacc acatggtggg tgagcagccc ccatgcactg acggtaaatt     3300
```

```
cccctgtgga ctcatttctg ttggtttcta ttacacctgg ccaggcgtgg tacaatacag    3360
gtcga                                                                3365

<210> SEQ ID NO 42
<211> LENGTH: 1325
<212> TYPE: DNA
<213> ORGANISM: Homo sapiens
<220> FEATURE:
<221> NAME/KEY: misc_feature
<223> OTHER INFORMATION: Incyte ID No: 3168839CB1

<400> SEQUENCE: 42
catggcatcc ccagcctagc tcccaatccc actttggcac gatgttagcc aacagctcct      60
caaccaacag ttctgttctc ccgtgtcctg actaccgacc tacccaccgc ctgcacttgg     120
tggtctacag cttggtgctg gctgccgggc tccccctcaa cgcgctagcc ctctgggtct     180
tcctgcgcgc gctgcgcgtg cactcggtgg tgagcgtgta catgtgtaac ctggcggcca     240
gcgacctgct cttcacccte tcgctgcccg ttcgtctctc ctactacgca ctgcaccact     300
ggcccttccc cgacctcctg tgccagacga cgggcgccat cttccagatg aacatgtacg     360
gcagctgcat cttcctgatg ctcatcaacg tggaccgcta cgccgccatc gtgcacccgc     420
tgcgactgcg ccacctgcgg cggccccgcg tggcgcggct gctctgcctg ggcgtgtggg     480
cgctcatcct ggtgtttgcc gtgcccgccg cccgcgtgca caggccctcg cgttgccgct     540
accgggacct cgaggtgcgc ctatgcttcg agagcttcag cgacgagctg tggaaaggca     600
ggctgctgcc cctcgtgctg ctggccgagg cgctgggctt cctgctgccc ctggcggcgg     660
tggtctactc gtcgggccga gtcttctgga cgctggcgcg ccccgacgcc acgcagagcc     720
agcggcggcg gaagaccgtg cgcctcctgc tggctaacct cgtcatcttc ctgctgtgct     780
tcgtgcccta caacagcacg ctggcggtct acgggctgct gcggagcaag ctggtggcgg     840
ccagcgtgcc tgcccgcgat cgcgtgcgcg gggtgctgat ggtgatggtg ctgctggccg     900
gcgccaactg cgtgctggac ccgctggtgt actactttag cgccgagggc ttccgcaaca     960
ccctgcgcgg cctgggcact ccgcaccggg ccaggacctc ggccaccaac gggacgcggg    1020
cggcgctcgc gcaatccgaa aggtccgccg tcaccaccga cgccaccagg ccggatgccg    1080
ccatgtcccc aggattccgc cctctgaaca cacatgccat tgcgctgtcc gtgcccgact    1140
cccaacgcct ctcgttctgg gaggcttaca gggtgtacac acaagaaggt gggctgggca    1200
cttggacctt tgggtggcaa ttccagctta gcaacgcaga gagtacaaa gtgtggaagc     1260 cagggcccag ggaaggcagt gctgctggaa atggcttctt taaactgtga gcacgcagag    1320
caccc                                                               1325

<210> SEQ ID NO 43
<211> LENGTH: 2124
<212> TYPE: DNA
<213> ORGANISM: Homo sapiens
<220> FEATURE:
<221> NAME/KEY: misc_feature
<223> OTHER INFORMATION: Incyte ID No: 3291235CB1

<400> SEQUENCE: 43
gtcttacctc ttaatagtat tagaatggca attaaatctc gacacgtttt aattaaattt      60
caacatgagt tttgcagggg acattcgaag tgtagcgctc gccatctccc atcccaagta    120
cctaagggct acaacgctgt cgccagagag gaagtcactg agtgcccact gccacccccc    180
```

```
cacatatgct cgtggtcccc agcatccttg agccaccagg agtgagggct gctgctccct    240
gagacctggc tccaaggagg atgccacagc cgcctgccag ctccggtctg caccatgagt    300
gatgagcggc ggctgcctgg cagtgcagtg ggctggctgg tatgtggggg cctctccctg    360
ctggccaatg cctggggcat cctcagcgtt ggcgccaagc agaagaagtg gaagcccttg    420
gagttcctgc tgtgtacgct cgcgccacc cacatgctaa atgtggccgt gcccatcgcc     480
acctactccg tggtgcagct gcggcggcag cgccccgact cgagtggaa tgagggtctc     540 tgcaaggtct tcgtgtccac cttctacacc ctcaccctgg ccacctgttt ctctgtcacc    600
tccctctcct accaccgcat gtggatggtc tgctggcctg tcaactaccg gctgagcaat    660
gccaagaagc aggcggtgca cacagtcatg ggtatctgga tggtgtcctt catcctgtcg    720
gccctgcctg ccgttggctg gcacgacacc agcgagcgct cctacaccca tggctgccgc    780
ttcatcgtgg ctgagatcgg cctgggcttt ggcgtctgct tcctgctgct ggtgggcggc    840
agcgtggcca tgggcgtgat ctgcacagcc atcgccctct tccagacgct ggccgtgcag    900
gtggggcgcc aggccgacca ccgcgccttc accgtgccca ccatcgtggt ggaggacgcg    960
cagggcaagc ggcgctcctc catcgatggc tcggagcccg ccaaaacctc tctgcagacc   1020
acgggcctcg tgaccaccat agtcttcatc tacgactgcc tcatgggctt ccctgtgctg   1080
gtggtgagct tcagcagcct gcgggccgac gcctcagcgc cctggatggc actctgcgtg   1140
ctgtggtgct ccgtggccca ggccctgctg ctgcctgtgt tcctctgggc ctgcgaccgc   1200
taccgggctg acctcaaagc tgtccgggag aagtgcatgg ccctcatggc caacgacgag   1260
gagtcagacg atgagaccag cctggaaggt ggcatctccc cggacctggt gttggagcgc   1320
tccctggact atggctatgg aggtgatttt gtggccctag ataggatggc caagtatgag   1380
atctccgccc tggagggggg cctgccccag ctctacccac tgcggcccct gcaggaggac   1440
aagatgcaat acctgcaggt cccgcccacg cggcgcttct cccacgacga tgcggacgtg   1500
tgggccgccg tcccgctgcc cgccttcctg ccgcgctggg gctccggcaa ggacctgtcc   1560
gccctggcgc acctggtgct gcctgccggg cccgagcggc ccgcgccag cctcctggcc    1620 ttcgcggagg acgcaccact gtcccgcgcg cgccgccgct cggccgagag cctgctgtcg   1680
ctgcggccct cggccgtgga tagcggcccg cggggagccc gcgactcgcc ccccggcagc   1740
ccgcgccgcc gccccgggcc cggccccgc tccgcctcgg cctcgctgct gcccgacgcc    1800
ttcgccctga ccgccttcga gtgcgagcca caggccctgc ccgccgccc cgggcccttc   1860 cccgctgcgc ccgccgcccc cgacggcgca gatcccggag aggccccgac gccccaagc    1920 agcgcccagc ggagcccagg gccacgcccc tctgcgcact cgcacgccgg ctctctgcgc   1980
cccggcctga gcgcgtcgtg gggcgagccc ggggggctgc gcgcggcggg cggcggcggc   2040
agcaccagca gcttcctgag ttccccctcc gagtcctcgg gctacgccac gctgcactcg   2100
gactcgctgg gctccgcgtc ctag                                         2124
```

<210> SEQ ID NO 44
<211> LENGTH: 942
<212> TYPE: DNA
<213> ORGANISM: Homo sapiens
<220> FEATURE:
<221> NAME/KEY: misc_feature
<223> OTHER INFORMATION: Incyte ID No: 7472001CB1

<400> SEQUENCE: 44

```
atggaaagaa tcaacagcac actgttgact gcgtttatcc tgacaggaat tccgtatcca    60
```

| | |
|---|---|
| ctcaggctaa ggacactctt ttttgtgttc ttttttctaa tctacatcct gactcagctg | 120 |
| ggaaacctgc ttattttaat cactgtctgg gcagacccaa ggctccatgc ccgccccatg | 180 |
| tacatctttc ttggtgttct ctcagtcatt gatatgagca tctcctccat cattgtccct | 240 |
| cgcctcatga tgaacttcac tttaggtgtc aaacccatcc catttggtgg ctgtgttgct | 300 |
| caactctatt tctatcactt cctgggcagc acccagtgct tcctctacac cctaatggcc | 360 |
| tatgacaggt acctggcaat atgtcagccc ctgcgctacc ctgtgctcat gactgctaag | 420 |
| ctgagcgcct tgcttgtggc tggagcctgg atggcaggat ccatccatgg ggctctccag | 480 |
| gccatcctaa ccttccgcct gccctactgt gggcccaatc aggtggatta cttcttctgt | 540 |
| gacatccctg cagtgttgag actggcctgt gctgacacaa cagtcaacga gctggtgacg | 600 |
| tttgtagaca ttggggtggt ggttgccagt tgcttctccc tgatcctcct ctcctacata | 660 |
| cagatcattc aggccatcct gagaatccac acagctgatg ggcggcgccg ggcttttca | 720 |
| acttgtggag cccatgtaac cgtggtcacc gtgtactatg tgccctgtgc cttcatctac | 780 |
| ctgaggcctg aaaccaacag ccccctggat ggggcagctg ccctagtccc cacggccatc | 840 |
| actccttttcc tcaaccccct tatctacact ctgcggaacc aagaggtgaa gctggccctg | 900 |
| aaaagaatgc tcagaagccc aagaactccg agtgaggttt ga | 942 |

<210> SEQ ID NO 45
<211> LENGTH: 1197
<212> TYPE: DNA
<213> ORGANISM: Homo sapiens
<220> FEATURE:
<221> NAME/KEY: misc_feature
<223> OTHER INFORMATION: Incyte ID No: 7472003CB1

<400> SEQUENCE: 45

| | |
|---|---|
| atgcacaccg tggctacgtc cggacccaac gcgtcctggg gggcaccggc caacgcctcc | 60 |
| ggctgcccgg gctgtggcgc caacgcctcg gacggcccag tcccttcgcc gcgggccgtg | 120 |
| gacgcctggc tcgtgccgct cttcttcgcg gcgctgatgc tgctgggcct ggtggggaac | 180 |
| tcgctggtca tctacgtcat ctgccgccac aagccgatgc ggaccgtgac caacttctac | 240 |
| atcgccaacc tggcggccac ggacgtgacc ttcctcctgt gctgcgtccc cttcacggcc | 300 |
| ctgctgtacc cgctgcccgg ctgggtgctg gcgacttca tgtgcaagtt cgtcaactac | 360 |
| atccagcagg tctcggtgca ggccacgtgt gccactctga ccgccatgag tgtggaccgc | 420 |
| tggtacgtga cggtgttccc gttgcgcgcc ctgcaccgcc gcacgccccg cctggcgctg | 480 |
| gctgtcagcc tcagcatctg gacaggctct gcggcggtgt ctgcgccggt gctcgccctg | 540 |
| caccgcctgt cacccgggcc gcgcgcctac tgcagtgagg ccttccccag ccgcgccctg | 600 |
| gagcgcgcct tcgcactgta caacctgctg gcgctgtacc tgctgccgct gctcgccacc | 660 |
| tgcgcctgct atgcggccat gctgcgccac ctgggccggg tcgccgtgcg ccccgcgccc | 720 |
| gccgatagcg ccctgcaggg gcaggtgctg gcagagcgcg caggcgccgt gcgggccaag | 780 |
| gtctcgcggc tggtggcggc cgtggtcctg ctcttcgccg cctgctgggg ccccatccag | 840 |
| ctgttcctgg tgctgcaggc gctggccccc gcgggctcct ggcacccacg cagctacgcc | 900 |
| gcctacgcgc ttaagacctg gctcactgc atgtcctaca gcaactccgc gctgaacccg | 960 |
| ctgctctacg ccttcctggg ctcgcacttc cgacaggcct tccgccgcgt ctgcccctgc | 1020 |
| gcgccgcgcc gccccgccg ccccgccgg cccggaccct cggaccccgc agccccacac | 1080 |
| gcggagctgc tccgcctggg gtcccacccg gcccccgcca gggcgcagaa gccagggagc | 1140 |

-continued

| | |
|---|---|
| agtgggctgg ccgcgcgcgg gctgtgcgtc ctgggggagg acaacgcccc tctctga | 1197 |

<210> SEQ ID NO 46
<211> LENGTH: 1110
<212> TYPE: DNA
<213> ORGANISM: Homo sapiens
<220> FEATURE:
<221> NAME/KEY: misc_feature
<223> OTHER INFORMATION: Incyte ID No: 7472004CB1

<400> SEQUENCE: 46

| | |
|---|---|
| atggctccca ctggtttgag ttccttgacc gtgaatagta cagctgtgcc cacaacacca | 60 |
| gcagcattta agagcctaaa cttgcctctt cagatcaccc tttctgctat aatgatattc | 120 |
| attctgtttg tgtctttcct tgggaacttg gttgtttgcc tcatggttta ccaaaaagct | 180 |
| gccatgaggt ctgcaattaa catcctcctt gccagcctag cttttgcaga catgttgctt | 240 |
| gcagtgctga acatgccctt tgccctggta actattctta ctaccgatg gattttaggg | 300 |
| aaattcttct gtagggtatc tgctatgttt ttctggttat ttgtgataga aggagtagcc | 360 |
| atcctgctca tcattagcat agataggttc cttattatag tccagaggca ggataagcta | 420 |
| aacccatata gagctaaggt tctgattgca gtttcttggg caacttcctt ttgtgtagct | 480 |
| tttcctttag ccgtaggaaa ccccgacctg cagatacctt cccgagctcc ccagtgtgtg | 540 |
| tttgggtaca caaccaatcc aggctaccag gcttatgtga ttttgatttc tctcatttct | 600 |
| ttcttcatac ccttcctggt aatactgtac tcatttatgg gcatactcaa caccccttcgg | 660 |
| cacaatgcct tgaggatcca tagctaccct gaaggtatat gcctcagcca ggccagcaaa | 720 |
| ctgggtctca tgagtctgca gagacctttc cagatgagca ttgacatggg cttaaaaaca | 780 |
| cgtgccttca ccactatttt gattctcttt gctgtcttca ttgtctgctg ggccccattc | 840 |
| accacttaca gccttgtggc aacattcagt aagcactttt actatcagca caactttttt | 900 |
| gagattagca cctggctact gtggctctgc tacctcaagt ctgcattgaa tccgctgatc | 960 |
| tactactgga ggattaagaa attccatgat gcttgcctgg acatgatgcc taagtccttc | 1020 |
| aagttttgc cgcagctccc tggtcacaca aagcgacgga tacgtcctag tgctgtctat | 1080 |
| gtgtgtgggg aacatcggac ggtggtgtga | 1110 |

<210> SEQ ID NO 47
<211> LENGTH: 582
<212> TYPE: DNA
<213> ORGANISM: Homo sapiens
<220> FEATURE:
<221> NAME/KEY: misc_feature
<223> OTHER INFORMATION: Incyte ID No: 7475687CT1

<400> SEQUENCE: 47

| | |
|---|---|
| atggcctatg acaggtacct ggcaatatgt cagcccctgc gctacccagt gctcatgaat | 60 |
| gggaggttat gcacagtcct tgtggctgga gcttgggtcg ccggctccat gcatgggtct | 120 |
| atccaggcca ccctgacctt ccgcctgccc tactgtgggc ccaatcaggt agattacttt | 180 |
| atctgtgaca tccccgcagt attgagactg gcctgtgctg acacaactgt caatgagctt | 240 |
| gtgacctttg tggacatcgg ggtagtggcc gccagttgct tcatgttaat tctgctctcg | 300 |
| tatgccaaca tagtaaatgc catcctgaag atacgcacca ctgatgggag gcgccgggcc | 360 |
| ttctccacct gtggctccca cctaatcgtg gtcacagtct actatgtccc ctgtatttc | 420 |
| atctacctta gggctggctc caaaggcccc ctggatgggg cagcggctgt gttttacact | 480 |
| gttgtcactc cattactgaa ccccctcatc tatacactga ggaaccagga agtgaagtct | 540 |

```
gccctgaaga ggataacagc aggccaggcg gatgtaaata ac                  582
```

<210> SEQ ID NO 48
<211> LENGTH: 519
<212> TYPE: DNA
<213> ORGANISM: Homo sapiens
<220> FEATURE:
<221> NAME/KEY: misc_feature
<223> OTHER INFORMATION: Incyte ID No: 7483029CT1

<400> SEQUENCE: 48

```
atgtacctgg tcaccgtgct cgggaacctg ctcatcatcc tggccacaat ctcagactcc   60
cacctccaca cccccatgta cttcttcctc tccaacctgt cctttgcaga catctgtttt  120
gtgtctacca ctgtcccaaa gatgctggtg aacatccaga cacagagcag agtcatcacc  180
tatgcagact gcatcaccca gatgtgcttt tttatactct ttgtagtgtt ggacagctta  240
ctcctgactg tgatggccta tgaccggttt gtggccatct gtcaccccct gcactacaca  300
gtcattatga actcctggct ctgtggactg ctggttctgg tgtcctggat cgtgagcatc  360
ctatattctc tgttacaaag cataatggca ttgcagctgt ccttctgtac agaattgaaa  420
atccctcatt ttttctgtga acttaatcag gtcatccacc ttgcctgttc cgacactttt  480
attaatgaca tgatgatgaa ttttacaagt gtgctgctg                         519
```

<210> SEQ ID NO 49
<211> LENGTH: 663
<212> TYPE: DNA
<213> ORGANISM: Homo sapiens
<220> FEATURE:
<221> NAME/KEY: misc_feature
<223> OTHER INFORMATION: Incyte ID No: 7477933CT1

<400> SEQUENCE: 49

```
cccatgtact tcttcctctc caacctgtgc tgggctgaca tcggtctcac ctcggccacg   60
gttcccaagg tgattctgga tatgcagtcg catagcagag tcatctctca tgtgggctgc  120
ctgacacaga tgtctttctt ggtccttttt gcatgtatag aaggcatgct cctgactgtg  180
atggcctatg gctgctttgt agccatctgt cgccctctgc actaccccagt catagtgaat  240
cctcacctct gtgtcttctt cgttttggtg tccttttttcc ttaacctgtt ggattcccag  300
ctgcacagtt ggattgtgtt acaattcacc atcatcaaga atgtggaaat ctctaatttt  360
ttctgtgacc cctctcagct tctcaaacctt gcctgttctg acagcgtcat caatagcata  420
ttcatatatt tcgatagtac tatgtttggt tttcttccca tttcagggat ccttttgtct  480
tactataaaa ttgtcccctc cattctaagg atgtcatcgt cagatgggaa gtataaagcc  540
ttctccacct atggctctca cctaggagtt gtttgctggt tttatggaac agtcattggc  600
atgtacctgg cttcagccgt gtcaccaccc cccaggaatg tgtggtggc atcagtgatg  660
tag                                                                663
```

<210> SEQ ID NO 50
<211> LENGTH: 911
<212> TYPE: DNA
<213> ORGANISM: Homo sapiens
<220> FEATURE:
<221> NAME/KEY: misc_feature
<223> OTHER INFORMATION: Incyte ID No: 7475164CT1

<400> SEQUENCE: 50

```
gggctgagtt tatcctggca ggcttgacac aacgcccaga acttcaactg ccactcttcc   60
```

-continued

| | |
|---|---|
| tcctgttcct tggaatatat gtggtcacag tggtggggaa cctgggcatg atcttcttaa | 120 |
| ttgctctcag ttctcaactt taccctccag tgtattattt tctcagtcat tgtctttca | 180 |
| ttgatctctg ctactcctct gtcattaccc ctaagatgct ggtgaacttt gttccagagg | 240 |
| agaacattat ctcctttctg gaatgcatta ctcaacttta tttcttcctt attttgtaa | 300 |
| ttgcagaagg ctaccttctg acagccatgg aatatgaccg ttatgttgct atctgtcgcc | 360 |
| cactgcttta caatattgtc atgtcccaca gggtctgttc cataatgatg ctgtggtat | 420 |
| actcactggg ttttctgtgg gccacagtcc atactacccg catgtcagtg ttgtcattct | 480 |
| gtaggtctca tacggtcagt cattattttt gtgatattct ccccttattg actctgtctt | 540 |
| gctccagcac ccacatcaat gagattctgc tgttcattat tggaggagtt aataccttag | 600 |
| caactacact ggcggtcctt atctcttatg ctttcatttt ctctagtatc cttggtattc | 660 |
| attccactga ggggcaatcc aaagcctttg gcacttgtag ctcccatctc ttggctgtgg | 720 |
| gcatcttttt tgggtctata acattcatgt atttcaagcc ccttccagc actactatgg | 780 |
| aaaaagagaa ggtgtcttct gtgttctaca tcacaataat ccccatgctg aatcctctaa | 840 |
| tctatagcct gaggaacaag gatgtgaaaa atgcactgaa gagatgact aggggaaggc | 900 |
| agtcatcctg a | 911 |

<210> SEQ ID NO 51
<211> LENGTH: 332
<212> TYPE: DNA
<213> ORGANISM: Homo sapiens
<220> FEATURE:
<221> NAME/KEY: misc_feature
<223> OTHER INFORMATION: Incyte ID No: 7473909CT1

<400> SEQUENCE: 51

| | |
|---|---|
| caggccccag gacagccagt ggctgtgtca tcatgatctg ctttgccctc actgtcctct | 60 |
| cttacatccg catcttggcc acagtggttc agatccgttc agcagccagc cgccggaagg | 120 |
| ccttctccac ctgttcttcc cacctgggca tggtgctcct gttctatggc accggcagct | 180 |
| ccacctacat gcgacccacc accgctact ccccgctgga agggcgcttg gctgctgtct | 240 |
| tctactccat cctcatcccc accctgaatc cgctcatcta cagcctgagg aaccaggaca | 300 |
| tgaagagagc cctgtggaag ctctatctcc ag | 332 |

<210> SEQ ID NO 52
<211> LENGTH: 538
<212> TYPE: DNA
<213> ORGANISM: Homo sapiens
<220> FEATURE:
<221> NAME/KEY: misc_feature
<223> OTHER INFORMATION: Incyte ID No: 7475252CT1

<400> SEQUENCE: 52

| | |
|---|---|
| agagccagag aatctcacag gtgtcttaga attcctgctc ctgggactcc cagatgatcc | 60 |
| agaactgcag cccgtcctct ttgggctgtt cctgtccatg tacctggtca tggtgctggg | 120 |
| gaacctgctc atcattctgg ccgtcagctc tgactcccat ctccacagcc ccatgtactt | 180 |
| cttcctctcc aacctgtcct ggctgacat cggttttgcc tctactactg tcccaagat | 240 |
| gattgtggac atccaggctc atagtagact catctcttac gtgggctgcc tgactcagat | 300 |
| gtcttttttg atctttttcg catgtatgga aagtctgctc ctgattgtga tggcctatga | 360 |
| ccggttcgtg gccatctgtc accccctgca ctaccaagtc atcatgagcc cacgactctg | 420 |

```
tggcttctta gttttggtgt cttttttttct tagccttttg gactctcagc tgcacaattt    480
gattgtgtta caacttacct gcttcaacga tgtggaaatc tctaattttt ttctgtga      538

<210> SEQ ID NO 53
<211> LENGTH: 279
<212> TYPE: DNA
<213> ORGANISM: Homo sapiens
<220> FEATURE:
<221> NAME/KEY: misc_feature
<223> OTHER INFORMATION: Incyte ID No: 7927572CT1

<400> SEQUENCE: 53
tcttttagat gcccagctgt acaatttgat tgccttacaa atgacctgct tcaaggatgt    60
ggaaattcct aatttcttct gtgacccttc tcaactcccc catcttgcat gttgtgacac    120
cttcaacaat aacataatcc tgtatttccc tgatgccata tttggttttc ttcccatctc    180
ggggacactt ttctcttacg ataaaattgt ttcctccatt ctgagggttt catcatcagg    240
tgggaagtat aaagccttct ccacctatgg gtctcacct                           279

<210> SEQ ID NO 54
<211> LENGTH: 291
<212> TYPE: DNA
<213> ORGANISM: Homo sapiens
<220> FEATURE:
<221> NAME/KEY: misc_feature
<223> OTHER INFORMATION: Incyte ID No: 7481257CT1

<400> SEQUENCE: 54
atggaggtaa ccacatttgc catgtgcctg attatagttc ttgttcctct tcttcttatt    60
cttgtgtcat atggtttcat tgctgtggct gtactcaaga tcaagtctgc agcaggaaga    120
caaaaagcat ttgggacctg ttcctcccat ctcgttgtgg tatccatctt ctgtgggaca    180
gttacataca tgtatataca gccaggaaac agtccaaatc agaatgaggg caaacttctc    240
agtatatttt actccattgt tactcccagc ttgaacccat taatttatac g             291

<210> SEQ ID NO 55
<211> LENGTH: 402
<212> TYPE: DNA
<213> ORGANISM: Homo sapiens
<220> FEATURE:
<221> NAME/KEY: misc_feature
<223> OTHER INFORMATION: Incyte ID No: 7485790CT1

<400> SEQUENCE: 55
aggatccaga actgcagccc atcctcgctg ggctgtccct gtccatgtat ctggtcacgg    60
tgctgaggaa cctcctcatc agcctggctg tcagctctga ctcccacctc cacacccaa    120 tgtgcttctt cctctccaac ctgtgctggg ctgacatcgg tttcacctcg gccacggttc    180
ccaagatgat tgtggacatg cggtcgcata gcggagtcat ctcttatgcg gactgcctga    240
cacggatgtc tttcttggtc cttttttgcat gtgtagaaga catgctcctg actgtgatgg    300
cctatgactg ttttgtagcc atctgtcgcc ctctgcacta cccagtcatc gtgaatcctc    360
acctctgtgt cttcttagtt tcggtgtcct tttccttagc ct                       402

<210> SEQ ID NO 56
<211> LENGTH: 639
<212> TYPE: DNA
<213> ORGANISM: Homo sapiens
<220> FEATURE:
<221> NAME/KEY: misc_feature
<223> OTHER INFORMATION: Incyte ID No: 7482993CT1
```

<400> SEQUENCE: 56

```
ggatcagagt gtctcctact ggcagcaatg gcatatgatc gttacattgc aatctgcaat      60
cctttaaggt attcagttat tctgagcaag gttctatgca atcaattagc agcctcatgc     120
tgggctgctg gtttccttaa ctcagtggtg catacagtgt tgacattctg cctgcccttc     180
tgtggcaaca atcagattaa ttacttcttc tgtgacatcc cccctttgct gatcttgtct     240
tgtggaaaca cttctgtcaa tgagttggca ctgctatcca ctggggtctt cattggttgg     300
actcctttcc tttgtatcgt actttcctac atttgcataa tctccaccat cttgaggatc     360
cagtcctcag agggaagacg aaaagccttt tctacatgtg cctcccacct ggccattgtc     420
tttctctttt atggcagcgc catctttaca tatgtacggc ccatctcaac ttactcatta     480
aagaaagata ggttggtttc agtgttgtac agtgttgtta cccccatgct aaaccctata     540
atttacacat tgaggaataa ggacatcaaa gaagctgtca aaactatagg gagcaagtgg     600
cagccaccaa tttcctcttt ggatagtaaa ctcacttat                             639
```

<210> SEQ ID NO 57
<211> LENGTH: 1370
<212> TYPE: DNA
<213> ORGANISM: Homo sapiens
<220> FEATURE:
<221> NAME/KEY: misc_feature
<223> OTHER INFORMATION: Incyte ID No: 2829053CB1

<400> SEQUENCE: 57

```
cggcaccaga aggatataac cagaattctc cagcaacatg aggaggaaaa gaagaaatgg      60
gcacaacagg tggagaagga aagggagcta gagctcgaga cagactggat gagcagcaaa     120
gggtcctgga aggaaagaat gaagaggccc tgcaagtcct ccgggcctca tatgaacagg     180
agaaagaagc gcttacccac tctttccggg aggccagttc tacccagcag agaccatag      240
acagactgac ctcacagctg gaggctttcc aggccaaaat gaagagggtg gaggagtcca     300
ttctgagccg aaactataag aaacatatcc aggattatgg gagccccagc cagttctggg     360
agcaggagct ggagagctta cactttgtca tcgagatgaa gaatgagcgt attcatgagc     420
tggacaagcg gctgatcctc atggaaacag tgaaagagaa aaatctgata ttggaggaaa     480
aaattacgac cctgcaacag gaaaatgagg acctccatgt ccgaagccgc aaccaggtgg     540
tcctgtcaag gcagctgtca gaagacctgc ttctcacgcg tgaggccctg agaaggagg      600
tgcagctgcg gcgacagctc cagcaggaga aggaggagct gttgtaccgg gtccttgggg     660
ccaatgcctc gcctgccttc cctctggccc ctgtcactcc cactgaggtc tctttcctcg     720
ccacataggg tgcagggcct gggcccacca cgacgcctga agtcacagct ccttccaagg     780
tttttctgga gaagacagca ggagcctctc agttcttttc caggaaggaa cgagggtggg     840
agcgagatgg agatcctggg tgtgtgccca gtgagccctg ggccttgag ttacatggaa      900
tcacccacag ggttttggag ccccgagaa gcgtcttccc ttgagttggc caagggaata     960
agcaagagga gacatttcct ccctgcccca gcactctgtc ccaatccgag aagttccgag    1020
gctttcccag gggcagtctg tgtcacgctg ccatttgac ataaaggaga cagccctgg     1080
tcccagcttg tcagctctgc tgccgacttg ctgacttatc aacttcctct aggtgttcc      1140
actccaccct ggcctgctca gagcctcagt ttacccctgc attaaaatgg tgggggact     1200
ggtcaaagga ctcttatgcc actgcagtgg cccattctag gattgtctga aggccagagt    1260
aggggttggg gggagtgtgg acaaaccccg caaatcagag tggggaaggt gagtggtaga    1320
```

```
gaggggggtct ctgaaggccc ttggggctga cagggccagg cagcctcccc          1370
```

<210> SEQ ID NO 58
<211> LENGTH: 1567
<212> TYPE: DNA
<213> ORGANISM: Homo sapiens
<220> FEATURE:
<221> NAME/KEY: misc_feature
<223> OTHER INFORMATION: Incyte ID No: 3068234CB1

<400> SEQUENCE: 58

```
gagggactgc gttctaatac ggagctccga ggatgttcac ttcttctcca caatgaatga    60
gtgtcactat gacaagcaca tggactttt ttataatagg agcaacactg atactgtcga   120
tgactggaca ggaacaaagc ttgtgattgt tttgtgtgtt gggacgtttt tctgcctgtt   180
tatttttttt tctaattctc tggtcatcgc ggcagtgatc aaaaacagaa aatttcattt   240
ccccttctac tacctgttgg ctaatttagc tgctgccgat ttcttcgctg gaattgccta   300
tgtattcctg atgtttaaca caggcccagt ttcaaaaact ttgactgtca accgctggtt   360
tctccgtcag gggcttctgg acagtagctt gactgcttcc ctcaccaact tgctggttat   420
cgccgtggag aggcacatgt caatcatgag gatgcgggtc catagcaacc tgaccaaaaa   480
gagggtgaca ctgctcattt tgcttgtctg ggccatcgcc atttttatgg gggcggtccc   540
cacactgggc tggaattgcc tctgcaacat ctctgcctgc tcttccctgg cccccattta   600
cagcaggagt taccttgttt tctggacagt gtccaacctc atggccttcc tcatcatggt   660
tgtggtgtac ctgcggatct acgtgtacgt caagaggaaa accaacgtct gtctccgca    720
tacaagtggg tccatcagcc gccggaggac acccatgaag ctaatgaaga cggtgatgac   780
tgtcttaggg gcgtttgtgg tatgctggac cccgggcctg gtggttctgc tcctcgacgg   840
cctgaactgc aggcagtgtg gcgtgcagca tgtgaaaagg tggttcctgc tgctggcgct   900
gctcaactcc gtcgtgaacc ccatcatcta ctcctacaag gacgaggaca tgtatggcac   960
catgaagaag atgatctgct gcttctctca ggagaaccca gagaggcgtc cctctcgcat  1020
cccctccaca gtcctcagca ggagtgacac aggcagccag tacatagagg atagtattag  1080
ccaaggtgca gtctgcaata aaagtacttc ctaaactctg gatgcctctc ggcccaccca  1140
ggcctcctct gggaaaagag ctgttaagaa tgattacctg tctctaacaa agcccatgta  1200
cagtgttatt tgaggtctcc attaatcact gctagatttc tttaaaaaat tttttttcat  1260
agtttaaaag catgggcagt aaagagagga cctgctgcat ttagagaaag cacagaaacg  1320
ggagaggttc ggcgggtccc tgcttgtcct atgaactgct cagagctcct gtcagtccag  1380
ctgggccttc tggggtctgg caccatttcg tagccattct ctttgtattt taaaaggacg  1440
ttatgaaagg gcttagacca aaataaatca taatgttact tgagccacct tatatagctg  1500
cttggagagt ctatgtagtt cttttctgcat gcattaaaaa tgtttagaaa tgcttcaaaa  1560
aaaaaaa                                                            1567
```

<210> SEQ ID NO 59
<211> LENGTH: 1321
<212> TYPE: DNA
<213> ORGANISM: Homo sapiens
<220> FEATURE:
<221> NAME/KEY: misc_feature
<223> OTHER INFORMATION: Incyte ID No: 5029478CB1

<400> SEQUENCE: 59

```
cagaccgctg cgggccgcag gcgccgggaa tgtcccctga atgcgcgcgg gcagcgggcg      60
acgcgccctt gcgcagcctg gagcaagcca accgcacccg ctttcccttc ttctccgacg     120
tcaagggcga ccaccggctg gtgctggccg cggtggagac aaccgtgctg gtgctcatct     180
ttgcagtgtc gctgctgggc aacgtgtgcg ccctggtgct ggtggcgcgc cgacgacgcc     240
gcggcgcgac tgcctgcctg gtactcaacc tcttctgcgc ggacctgctc ttcatcagcg     300
ctatccctct ggtgctggcc gtgcgctgga ctgaggcctg gctgctgggc cccgttgcct     360
gccacctgct cttctacgtg atgaccctga gcggcagcgt caccatcctc acgctggccg     420
cggtcagcct ggagcgcatg gtgtgcatcg tgcacctgca gcggcgcgtg cggggtcctg     480
ggcggcgggc gcgggcagtg ctgctggcgc tcatctgggg ctattcggcg gtcgccgctc     540
tgcctctctg cgtcttcttc cgagtcgtcc cgcaacggct ccccggcgcc gaccaggaaa     600
tttcgatttg cacactgatt tggcccacca ttcctggaga gatctcgtgg gatgtctctt     660
ttgttacttt gaacttcttg gtgccaggac tggtcattgt gatcagttac tccaaaattt     720
tacagatcac aaaggcatca aggaagaggc tcacggtaag cctggcctac tcggagagcc     780
accagatccg cgtgtcccag caggacttcc ggctcttccg caccctcttc ctcctcatgg     840
tctccttctt catcatgtgg agccccatca tcatcaccat cctcctcatc ctgatccaga     900
acttcaagca agacctggtc atctggccgt ccctcttctt ctgggtggtg gccttcacat     960 tgctaattc agccctaaac cccatcctct acaacatgac actgtgcagg aatgagtgga    1020
agaaaatttt tgctgcttc tggttcccag aaaagggagc catttaaca gacacatctg     1080 tcaaaagaaa tgacttgtcg attatttctg gctaattttt ctttatagca gagtttctca    1140
cacctggcga gctgtggcat gcttttaaac agagttcatt tccagtaccc tccatcagtg    1200
gcaccctgct ttaagaaaat gaacttatgc aaatagacat ccacagcgtc ggtaaattaa    1260
ggggtgatca ccaagtttca taatattttc cctttataaa aggatttgtt ggccaggtgc    1320
a                                                                   1321

<210> SEQ ID NO 60
<211> LENGTH: 1110
<212> TYPE: DNA
<213> ORGANISM: Homo sapiens
<220> FEATURE:
<221> NAME/KEY: misc_feature
<223> OTHER INFORMATION: Incyte ID No: 5102576CB1

<400> SEQUENCE: 60
atgttccttg tgagttgctc gcatccagca ttaagggctg gttttatct tttatttttc      60 caatcctctt tccttctcaa ggtgtccaag acacacggag ccacggaatc tcacaggtgt    120
ctgagaattc ctcctcctgg gactctcaga ggatccagaa ctgcagccgg ccctcgcttt    180
gctgtccctg tccctgtcca tgtatctggt cacggtgctg aggaacctgt tcagcatcct    240
ggctgtcagc tctgactgcc cctccacac ccccatgtac ttcttcctct ccaacctgtg     300
ctggcctgac atcggtttca cctcggccat ggttcccaag atgattgtgg acacgcagtc    360
gcatagcaga gtcatctctc atgcgggctg cctgacacag atgtctttcc tgctccttgt    420
tgcatgtata gaaggcatgc tcctgactgt gatggcctat gactgctttg tagccatctg    480
tcgccctctg cactacccag tcatcgtgaa tcctcacctc tgtgtctttt tcgttttggt    540
gtcctttttc cttagcctgt tggattccca gctgcacagt tggattgtgt tacaattaac    600
catcatcaag aatgtggaaa tctctaattt ggtctgtgac ccctctcaac ttctcaatct    660
```

```
tgcctgttct gacagcgtca tcaataacat attcatatat ttcgatagta ctatgtttgg      720
ttttcttccc atttcaggga tcttttttgtc ttactataaa attgtcccct ccattctaag      780
gatttcatcg tcagatggga agtataaagc cttctccacc tgtggctgtc atctagcagt      840
tgtttgctgg ttttatggaa caggcattgg catgtacctg acttcagctg tgtcaccacc      900
ccccaggaat ggtgtggtgg catcagtgat gtacgctgtg gtcaccccat gctgaacctt      960
ttcatctgca gcctgagaaa cagggacata caaagtgccc tgcggaggct gggcagcaga     1020
gcattcgaat ctcatgatct gttccatcct ttttcttgtg tgggtgagaa agggcaatca     1080
cattaaatct ctttatctgc aaaaaaaaaa                                     1110

<210> SEQ ID NO 61
<211> LENGTH: 1095
<212> TYPE: DNA
<213> ORGANISM: Homo sapiens
<220> FEATURE:
<221> NAME/KEY: misc_feature
<223> OTHER INFORMATION: Incyte ID No: 2200534CB1

<400> SEQUENCE: 61
atgaaggcca actacagcgc agaggagcgc tttctcctgc tgggtttctc cgactggcct       60
tccctgcagc cggtcctctt cgcccttgtc ctcctgtgct acctcctgac cttgacgggc      120
aactcggcgc tggtgctgct ggcggtgcgc gacccgcgcc tgcacacgcc catgtactac      180
ttcctctgcc acctggcctt ggtagacgcg ggcttcacta ctagcgtggt gccgccgctg      240
ctggccaacc tgcgcggacc agcgctctgg ctgccgcgca ccactgcac ggcccagctg      300 tgcgcatcgc tggctctggg ttcggccgaa tgcgtcctcc tggcggtgat ggctctggac      360 cgcgcggcc cagtgtgccg cccgctgcgc tatgcggggc tcgtctcccc cgcgcctatgt      420 cgcacgctgg ccagcgcctc ctggctaagc ggcctcacca actcggttgc gcaaaccgcg      480
ctcctggctg agcggccgct gtgcgcgccc gcctgctgg accacttcat ctgtgagctg      540
ccggcgttgc tcaagctggc ctgcggaggc gacggagaca ctaccgagaa ccagatgttc      600
gccgcccgcg tggtcatcct gctgctgccg tttgccgtca tcctggcctc ctacggtgcc      660
gtggcccgag ctgtctgttg catgcggttc agcggaggcc ggaggagggc ggtgggcacg      720
tgtgggtccc acctgacagc cgtctgcctg ttctacggct cggccatcta cacctacctg      780
cagcccgcgc agcgctacaa ccaggcacgg ggcaagttcg tatcgctctt ctacaccgtg      840
gtcacacctg ctctcaaccc gctcatctac accctcagga ataagaaagt gaaggggggca      900 gcgaggaggc tgctgcggag tctggggaga ggccaggctg ggcagtgagt agttggggag      960
gggagaaagt attaagccag aacccaagga tggaaatacc ccttagtgag tcagtttaga     1020
cttcaggctg ttcatttttg tatgataatc tgcaagattt gtcctaagga gtccaatggg     1080
ggatatgttt tcctc                                                     1095

<210> SEQ ID NO 62
<211> LENGTH: 1665
<212> TYPE: DNA
<213> ORGANISM: Homo sapiens
<220> FEATURE:
<221> NAME/KEY: misc_feature
<223> OTHER INFORMATION: Incyte ID No: 3275821CB1

<400> SEQUENCE: 62
ttcctacctt cactgattct ctgaaccttc ctgtcctcgc ctgtaaagta gattgtatga       60
ggactccatg aggtcatcca cttcaagtcc ttggcatagg ataattactc aaaaggtgat      120
```

-continued

| | |
|---|---|
| gacaatggcg cagggaggga tggtgacttg cctggagatg cacagcaccg tctctcccat | 180 |
| actcggtcat tcacaccatc attgattcac caggcaccca ctccgtgtcc agcaggactc | 240 |
| tggggacccc aaatggacac taccatggaa gctgacctgg gtgccactgg ccacaggccc | 300 |
| cgcacagagc ttgatgatga ggactcctac ccccaaggtg gctgggacac ggtcttcctg | 360 |
| gtggccctgc tgctccttgg gctgccagcc aatgggttga tggcgtggct ggccggctcc | 420 |
| caggcccggc atggagctgg cacgcgtctg gcgctgctcc tgctcagcct ggccctctct | 480 |
| gacttcttgt tcctggcagc agcggccttc cagatcctag atccggca tggggggacac | 540 |
| tggccgctgg ggacagctgc ctgccgcttc tactacttcc tatggggcgt gtcctactcc | 600 |
| tccggcctct tcctgctggc cgccctcagc ctcgaccgct gcctgctggc gctgtgccca | 660 |
| cactggtacc ctgggcaccg cccagtccgc ctgcccctct gggtctgcgc cggtgtctgg | 720 |
| gtgctggcca cactcttcag cgtgcccctgg ctggtcttcc ccgaggctgc cgtctggtgg | 780 |
| tacgacctgg tcatctgcct ggacttctgg gacagcgagg agctgtcgct gaggatgctg | 840 |
| gaggtcctgg ggggcttcct gccttttcctc ctgctgctcg tctgccacgt gctcacccag | 900 |
| gccacagcct gtcgcacctg ccaccgccaa cagcagcccg cagcctgccg ggcttcgcc | 960 |
| cgtgtggcca ggaccattct gtcagcctat gtggtcctga ggctgcccta ccagctggcc | 1020 |
| cagctgctct acctggcctt cctgtgggac gtctactctg gctacctgct ctgggaggcc | 1080 |
| ctggtctact ccgactacct gatcctactc aacagctgcc tcagccccttt cctctgcctc | 1140 |
| atggccagtg ccgacctccg gaccctgctg cgctccgtgc tctcgtcctt cgcggcagct | 1200 |
| ctctgcgagg agcggccggg cagcttcacg cccactgagc cacagaccca gctagattct | 1260 |
| gagggtccaa ctctgccaga gccgatggca gaggcccagt cacagatgga tcctgtggcc | 1320 |
| cagcctcagg tgaaccccac actccagcca cgatcggatc ccacagctca gccacagctg | 1380 |
| aaccctacgg cccagccaca gtcggatccc acagcccagc cacagctgaa cctcatggcc | 1440 |
| cagccacagt cagattctgt ggcccagcca caggcagaca ctaacgtcca gaccctgca | 1500 |
| cctgctgcca gttctgtgcc cagtccctgt gatgaagctt ccccaacccc atcctcgcat | 1560 |
| cctaccccag gggcccttga ggacccagcc acacctcctg cctctgaagg agaaagcccc | 1620 |
| agcagcaccc cgccagaggc ggccccgggc gcaggcccca cgtga | 1665 |

<210> SEQ ID NO 63
<211> LENGTH: 1609
<212> TYPE: DNA
<213> ORGANISM: Homo sapiens
<220> FEATURE:
<221> NAME/KEY: misc_feature
<223> OTHER INFORMATION: Incyte ID No: 3744167CB1

<400> SEQUENCE: 63

| | |
|---|---|
| tctccttttg ccgattagtg gacgtgacag agatgtgaat ggggcaggga tgtcctttga | 60 |
| tggcatcaag actttagctt ctggtgcgct gtgtcccagc tctgatttca gttgcagccg | 120 |
| tgatggacag ttgcatggaa gctgagactc tcactgacag tgaaaccctc aaatgaacac | 180 |
| aatccctgct ttcctgccaa ggatccttgt agggtccccc agcttcccca cttttttttct | 240 |
| gtgtcctgta ggcccagaag gatgtcggtc tgctaccgtc ccccagggaa cgagacactg | 300 |
| ctgagctgga agacttcgcg ggccacaggc acagccttcc tgctgctggc ggcgctgctg | 360 |
| gggctgcctg gcaacggctt cgtggtgtgg agcttggcgg gctggcggcc tgcacggggg | 420 |
| cgaccgctgg cggccacgct tgtgctgcac ctggcgctgg ccgacggcgc ggtgctgctg | 480 |

```
ctcacgccgc tctttgtggc cttcctgacc cggcaggcct ggccgctggg ccaggcgggc      540
tgcaaggcgg tgtactacgt gtgcgcgctc agcatgtacg ccagcgtgct gctcaccggc      600
ctgctcagcc tgcagcgctg cctcgcagtc acccgcccct tcctggcgcc tcggctgcgc      660
agcccggccc tggcccgccg cctgctgctg gcggtctggc tggccgccct gttgctcgcc      720
gtccggcccg ccgtctaccg ccacctgtgg agggaccgcg tatgccagct gtgccacccg      780
tcgccggtcc acgccgccgc ccacctgagc ctggagactc tgaccgcttt cgtgcttcct      840
ttcgggctga tgctcggctg ctacagcgtg acgctggcac ggctgcgggg cgcccgctgg      900
ggctccgggc ggcacggggc gcggtgggc cggctggtga gcgccatcgt gcttgccttc       960
ggcttgctct gggcccccta ccacgcagtc aaccttctgc aggcggtcgc agcgctggct     1020
ccaccggaag gggccttggc gaagctgggc ggagccggcc aggcggcgcg agcgggaact     1080
acggccttgg ccttcttcag ttctagcgtc aacccggtgc tctacgtctt caccgctgga     1140
gatctgctgc cccgggcagg tccccgtttc ctcacgcggc tcttcgaagg ctctggggag     1200
gcccgagggg gcggccgctc tagggaaggg accatggagc tccgaactac ccctcagctg     1260
aaagtggtgg ggcagggccg cggcaatgga gaccggggg gtgggatgga aaggacggt      1320 ccggaatggg accttgtgaca gcagacccta caacctgctg cccttccctg tcccttccca    1380 cccccaccc accctccaga ggtcagtgtt ctgggacatt tggggaccct tctttgacta     1440
gagtttggat ctggctgggt aggattacta tacacttggg gcaggcccag gctcctccaa     1500
actgagggat tatgagggtg gtgatggtcc ctgttaagga ctattgtgtg cttgcaagtt     1560
ggcatgtacc catgtgccag cattgcttac ttgttgccaa tagctgtta              1609

<210> SEQ ID NO 64
<211> LENGTH: 945
<212> TYPE: DNA
<213> ORGANISM: Homo sapiens
<220> FEATURE:
<221> NAME/KEY: misc_feature
<223> OTHER INFORMATION: Incyte ID No: 7472007CB1

<400> SEQUENCE: 64
atgtgggaaa actggacaat tgtcagtgaa tttgttctcg tgagcttctc agccctgtcc       60
actgagcttc aggctctact gtttctcctt ttcttgacca tttacttggt tactttaatg      120
ggcaatgtcc tcatcatcct ggtcactata gctgactctg cactacaaag tcctatgtac      180
ttcttcctca gaaacttgtc cttcctggag ataggtttca acttggtcat gtgcccaag      240 atgctgggga ccctgatcat tcaagacaca accatctcct tccttggatg tgccactcag      300
atgtatttct tcttcttttt tggggctgct gagtgctgcc tcctggccac catggcatat      360
gaccgctacg tggccatctg tgaccccttg cactacccag tcatcatggg ccacatatcc      420
tgtgcccagc tggcagctgc tcttggttc tcagggtttt cagtggccac tgtgcaaacc      480
acatggattt tcagtttccc ttttgtggc cccaacaggg tgaaccactt cttctgtgac      540
agccctcctg ttattgcact ggtctgtgct gacacctctg tgtttgaact ggaggctctg     600
acagccactg tcccattcat tctctttcct tcttgctga tcctgggatc ctatgtccgc      660
atcctctcca ctatcttcag gatgccgtca gctgagggga acatcaggc attctccacc      720 tgttccgccc acctcttggt tgtctctctc ttctatagca ctgccatcct cacgtatttc     780
cgaccccaat ccagtgcctc ttctgagagc aagaagctgc tgtcactctc ttccacagtg     840
gtgactccca tgttgaaccc catcatctac agctcaagga ataaagaagt gaaggctgca    900
```

```
ctgaagcggc ttatccacag gaccctgggc tctcagaaac tatga            945

<210> SEQ ID NO 65
<211> LENGTH: 1098
<212> TYPE: DNA
<213> ORGANISM: Homo sapiens
<220> FEATURE:
<221> NAME/KEY: misc_feature
<223> OTHER INFORMATION: Incyte ID No: 7472008CB1

<400> SEQUENCE: 65
atggagggat ctgttgaagc tacacctgaa attccagctc agatgaaatg tcatccttca     60
agacccagta cttttaaatca attatctttc tatggtgctg tgtcctcact aggaagaatg    120
catggtttag aaaccaaaag ctctgctgaa attagagctg gctgaagag atgtgataca    180 ctggtactag aggcatctac tttagaagga aatatggtca tagttcttgt gtccttgaag    240
gatccaaaac tccacatccc tatgtatttc tttctttcca acctttcctt ggtagacctc    300
tgtttgacca gcagctgtgt tccacagatg ttgattaact tctggggccc agaaaagacc    360
atcagctaca ttggctgtgc cattcaactc tatgtttttt tgtggcttgg ggccacggaa    420
tatgtccttc ttgttgtcat ggctgtggat tgttatgtag cagtgtgtca tccactgcaa    480
aataccatga tcatgcaccc aaaactttgt ctgcagctgg ctatcttggc atggggggact    540 ggcttggccc agtctctgat ccagtccccct gccaccctcc ggttacccctt ctgctcccag    600 cggatggtgg atgatgttgt ttgtgaagtc ccagctctga ttcagctctc cagtactgat    660
actacctaca gtgaaattca gatgtctatc gccagtgttg tcctcctggt gatgcccttg    720
atcattatcc tttcctcttc tggtgctatt gctaaggctg tgctgagaat taagtcaact    780
gcaggacaga agaaagcatt tggcacctgc atctctcacc ttcttgtggt ttctctctttt   840 tatggcactg tcacaggtgt ctaccttcaa ccaaaaaatc actatcctca tgaatggggc    900
aaatttctca ctctttttcta cactgtagta accccaactc ttaatcccct catctacact    960
ctaaggaaca aggagctcca tccttggcta aaagaggcca aggtacagac cgcttcagag   1020
agtgcaagcc ccaagcattg gcagcttcca catggtgttg gtcctgtggg tgtgcagaag   1080
acaagaactg agctttga                                                   1098

<210> SEQ ID NO 66
<211> LENGTH: 954
<212> TYPE: DNA
<213> ORGANISM: Homo sapiens
<220> FEATURE:
<221> NAME/KEY: misc_feature
<223> OTHER INFORMATION: Incyte ID No: 7472013CB1

<400> SEQUENCE: 66
atgagctttg cccctaatgc ttcacactct ccggtttttt tgctccttgg gttctcgaga     60
gctaacatct cctacactct cctcttcttc ctgttcctgg ctatttacct gaccaccata    120
ctggggaatg tgacactggt gctgctcatc tcctgggact ccagactgca ctcacccatg    180
tattatctgc ttcgtggcct ctctgtgata gacatggggc tatccacagt tacactgccc    240
cagttgctgg cccatttggt ctctcattac ccaaccattc ctgctgcccg ctgcttggct    300
cagttctttt tcttctatgc atttgggggt acagatacac ttgtcattgc tgtcatggct    360
ctggatcgct atgtggccat ctgtgacccc ctgcactatg ctttggtaat gaatcaccaa    420
cggtgtgcct gctactagc cttgagctgg gtggtgtcca tactgcacac catgttgcgt    480
```

```
gtgggactcg tcctgcctct ttgctggact ggggatgctg ggggcaacgt taaccttcct        540
cacttctttt gtgaccaccg gccacttctg cgagcctctc gttctgacat acattctaat        600
gagctggcca tattctttga gggtggcttc cttatgctgg gccccgtgtgc cctcattgta        660 ctctcttatg tccgaattgg ggccgctatt ctacgtttgc cttcagctgc tggtcgccgc        720
cgagcagtct ccacctgtgg atcccacctc accatggttg gtttcctcta cggcaccatc        780
atttgtgtct acttccagcc tcccttccag aactctcagt atcaggacat ggtggcttca        840
gtaatgtata ctgccattac acctttggcc aacccatttg tgtatagcct ccacaataag        900
gatgtcaagg gtgcactctg caggctgctt gaatgggtga aggtagaccc ctga             954

<210> SEQ ID NO 67
<211> LENGTH: 1008
<212> TYPE: DNA
<213> ORGANISM: Homo sapiens
<220> FEATURE:
<221> NAME/KEY: misc_feature
<223> OTHER INFORMATION: Incyte ID No: 7472015CB1

<400> SEQUENCE: 67
atggaatcat ctttctcatt tggagtgatc cttgctgtcc tggcctccct catcattgct         60
actaacacac tagtggctgt ggctgtgctg ctgttgatcc acaagaatga tggtgtcagt        120
ctctgcttca ccttgaatct ggctgtggct gacaccttga ttggtgtggc catctctggc        180
ctactcacag accagctctc cagcccttct cggcccacac agaagaccct gtgcagcctg        240
cggatggcat ttgtcacttc ctccgcagct gcctctgtcc tcacggtcat gctgatcacc        300
tttgacaggt accttgccat caagcagccc ttccgctact tgaagatcat gagtgggttc        360
gtggccgggg cctgcattgc cgggctgtgg ttagtgtctt acctcattgg cttcctccca        420
ctcggaatcc ccatgttcca gcagactgcc tacaaagggc agtgcagctt ctttgctgta        480 tttcacccctc acttcgtgct gaccctctcc tgcgttggct tcttcccagc catgctcctc        540
tttgtcttct tctactgcga catgctcaag attgcctcca tgcacagcca gcagattcga        600
aagatggaac atgcaggagc catggctgga ggttatcgat ccccacggac tcccagcgac        660
ttcaaagctc tccgtactgt gtctgttctc attgggagct ttgctctatc ctggaccccc        720
ttccttatca ctggcattgt gcaggtggcc tgccaggagt gtcacctcta cctagtgctg        780
gaacggtacc tgtggctgct cggcgtgggc aactccctgc tcaacccact catctatgcc        840
tattggcaga aggaggtgcg actgcagctc taccacatgg ccctaggagt gaagaaggtg        900
ctcacctcat tcctcctctt tctctcggcc aggaattgtg gcccagagag gcccagggaa        960
agttcctgtc acatcgtcac tatctccagc tcagagtttg atggctaa                   1008

<210> SEQ ID NO 68
<211> LENGTH: 930
<212> TYPE: DNA
<213> ORGANISM: Homo sapiens
<220> FEATURE:
<221> NAME/KEY: misc_feature
<223> OTHER INFORMATION: Incyte ID No: 7472016CB1

<400> SEQUENCE: 68
atgagggaaa ataaccagtc ctctacactg gaattcatcc tcctgggagt tactggtcag         60
caggaacagg aagatttctt ctacatcctc ttcctgttca tttaccccat cacattgatt        120
ggaaacctgc tcattgtcct agccatttgc tctgatgttc gccttcacaa ccccatgtat        180
tttctccttg ccaacctctc cttggttgac atcttcttct catcggtaac catccctaag        240
```

| | |
|---|---|
| atgctggcca accatctctt gggcagcaaa tccatctctt ttgggggatg cctaacgcag | 300 |
| atgtatttca tgatagcctt gggtaacaca gacagctata ttttggctgc aatggcatat | 360 |
| gatcgagctg tggccatcag ccacccactt cactacacaa caattatgag tccacggtct | 420 |
| tgtatctggc ttattgctgg gtcttgggtg attggaaatg ccaatgccct cccccacact | 480 |
| ctgctcacag ctagtctgtc cttcgtggc aaccaggaag tggccaactt ctactgtgac | 540 |
| attacccct tgctgaagtt atcctgttct gacatccact ttcatgtgaa gatgatgtac | 600 |
| ctaggggttg gcattttctc tgtgccatta ctatgcatca ttgtctccta tattcgagtc | 660 |
| ttctccacag tcttccaggt tccttccacc aagggcgtgc tcaaggcctt ctccacctgt | 720 |
| ggttcccacc tcacggttgt ctctttgtat tatggtacag tcatgggcac gtatttccgc | 780 |
| cctttgacca attatagcct aaaagacgca gtgatcactg taatgtacac ggcagtgacc | 840 |
| ccaatgttaa atcctttcat ctacagtctg agaaatcggg acatgaaggc tgccctgcgg | 900 |
| aaactcttca acaagagaat ctcctcgtaa | 930 |

<210> SEQ ID NO 69
<211> LENGTH: 711
<212> TYPE: DNA
<213> ORGANISM: Homo sapiens
<220> FEATURE:
<221> NAME/KEY: misc_feature
<223> OTHER INFORMATION: Incyte ID No: 7472017CB1

<400> SEQUENCE: 69

| | |
|---|---|
| atgggcatga ccaacagcag tgtcaaggga gacttcatcc tgctgctgtg gaacctaaaa | 60 |
| ggacctgaca aaacaatcac attcctgggt tgtgtcatcc agctctacat ctccctggca | 120 |
| ttgggctcca ctgagtgtgt cctcctggct gtaatggctt ttgatcgcta tgctgcagtt | 180 |
| tgcaaacctc tccactatac cgccgtaatg aaccctcagc tgtgccaggc tctggcaggg | 240 |
| gttgcgtggc tgagtggagt gggaaacact cttatccagg gcactgtcac cctctggctt | 300 |
| cctcgctgtg gacaccgatt gctccaacat ttcttccttg catgtgtgga catccatgat | 360 |
| aatgaggttc agctctttgt tgcttcactg gtcttgctcc tcttgccctt agtgctaata | 420 |
| ctgctgtcct atggacatat agccaaggtg gtcataagga tcaagtcagt ccaggcctgg | 480 |
| tgcaaaggcc tggggacatg tggatcccat ttgatagtag tgtccctctt ctgtgggacc | 540 |
| atcacagctg tctacatcca gtccaacagt tcttatgccc atgctcatgg gaagttcatc | 600 |
| tccctcttct atacagttgt gaccccgacc ctcaatcctc tcatctacac actgaggaat | 660 |
| aatgacgtga aggagcact gcgattattt aacagagact taggcacata a | 711 |

<210> SEQ ID NO 70
<211> LENGTH: 1092
<212> TYPE: DNA
<213> ORGANISM: Homo sapiens
<220> FEATURE:
<221> NAME/KEY: misc_feature
<223> OTHER INFORMATION: Incyte ID No: 7472018CB1

<400> SEQUENCE: 70

| | |
|---|---|
| atgggccccg gcgaggcgct gctggcgggt ctcctggtga tggtactggc cgtggcgctg | 60 |
| ctatccaacg cactggtgct gctttgttgc gcctacagcg ctgagctccg cactcgagcc | 120 |
| tcaggcgtcc tcctggtgaa tctgtctctg ggccacctgc tgctggcggc gctggacatg | 180 |
| cccttcacgc tgctcggtgt gatgcgcggg cggacaccgt cggcgcccgg cgcatgccaa | 240 |

-continued

```
gtcattggct tcctggacac cttcctggcg tccaacgcgg cgctgagcgt ggcggcgctg      300
agcgcagacc agtggctggc agtgggcttc ccactgcgct acgccggacg cctgcgaccg      360
cgctatgccg gcctgctgct gggctgtgcc tggggacagt cgctggcctt ctcaggcgct      420
gcacttggct gctcgtggct tggctacagc agcgccttcg cgtcctgttc gctgcgcctg      480
ccgcccgagc ctgagcgtcc gcgcttcgca gccttcaccg ccacgctcca tgccgtgggc      540
ttcgtgctgc cgctggcggt gctctgcctc acctcgctcc aggtgcaccg ggtggcacgc      600
agacactgcc agcgcatgga caccgtcacc atgaaggcgc tcgcgctgct cgccgacctg      660 cacccccagtg tgcggcagcg ctgcctcatc agcagaagc ggcgccgcca ccgcgccacc      720
aggaagattg gcattgctat tgcgaccttc ctcatctgct tgccccgta tgtcatgacc      780 aggctggcgg agctcgtgcc cttcgtcacc gtgaacgccc agtggggcat cctcagcaag      840
tgcctgacct acagcaaggc ggtggccgac ccgttcacgt actctctgct ccgccggccg      900
ttccgccaag tcctggccgg catggtgcac cggctgctga agagaacccc gcgcccagca      960
tccacccatg acagctctct ggatgtggcc ggcatggtgc accagctgct gaagagaacc     1020
ccgcgcccag cgtccaccca caacggctct gtggacacag agaatgattc ctgcctgcag     1080
cagacacact ga                                                         1092
```

```
<210> SEQ ID NO 71
<211> LENGTH: 927
<212> TYPE: DNA
<213> ORGANISM: Homo sapiens
<220> FEATURE:
<221> NAME/KEY: misc_feature
<223> OTHER INFORMATION: Incyte ID No: 7472019CB1

<400> SEQUENCE: 71
```

```
atggccatgg acaatgtcac agcagtgttt cagtttctcc ttattggcat ttctaactat       60
cctcaatgga gagacacgtt tttcacatta gtgctgataa tttacctcag cacattgttg      120
gggaatggat ttatgatctt tcttattcac tttgacccca acctccacac tccaatctac      180
ttcttcctta gtaacctgtc tttcttagac cttgttatg gaacagcttc catgccccag      240
gctttggtgc attgtttctc tacccatccc tacctctctt atccccgatg tttggctcaa      300
acgagtgtct ccttggcttt ggccacagca gagtgcctcc tactggctgc catggcctat      360
gaccgtgtgg ttgctatcag caatcccctg cgttattcag tggttatgaa tggcccagta      420
tgtgtctgct tggttgctac ctcatggggg acatcacttg tgctcactgc catgctcatc      480
ctatccctga ggcttcactt ctgtggggct aatgtcatca accattttgc ctgtgagatt      540
ctctccctca ttaagctgac ctgttctgat accagcctca tgaatttat gatcctcatc      600 accagtatct tcaccctgct gctaccattt gggtttgttc tcctctccta catacgaatt      660
gctatggcta tcataaggat tcgctcactc cagggcaggc tcaaggcctt taccacatgt      720
ggctctcacc tgaccgtggt gacaatcttc tatgggtcag ccatctccat gtatatgaaa      780
actcagtcca gtcctaccc tgaccaggac aagtttatct cagtgtttta tggagctttg      840
acacccatgt tgaacccct gatatatagc ctgagaaaaa aagatgttaa acgggcaata      900
aggaaagtta tgttgaaaag gacatga                                         927
```

```
<210> SEQ ID NO 72
<211> LENGTH: 1032
<212> TYPE: DNA
<213> ORGANISM: Homo sapiens
<220> FEATURE:
```

```
<221> NAME/KEY: misc_feature
<223> OTHER INFORMATION: Incyte ID No: 7472021CB1

<400> SEQUENCE: 72
atgcattttc ttcctactgt ctttggcttc ctaaacagag tcacacttgg tatcttcaga      60
gagactatgg tcaatttgac ttcaatgagt ggattccttc ttatggggtt ttctgatgag     120
cgtaagcttc agattttaca tgcattggta tttctggtga catacctgct ggccttgaca     180
ggcaacctcc tcattatcac catcattacc gtggaccgtc gtctccattc ccccatgtat     240
tacttttaa agcacctctc tcttctggac ctctgcttca tctctgtcac agtcccccag      300
tccattgcaa attcacttat gggcaacggt tacatttctc ttgttcagtg cattcttcag     360
gttttcttct tcatagctct ggcctcatca gaagtggcca ttctcacagt gatgtcttat     420
gacaggtacg cagcaatctg tcaaccactt cattatgaga ctattatgga tccccgtgcc     480
tgtaggcatg cagtgatagc tgtgtggatt gctgggggcc tctctgggct catgcatgct     540
gccattaact tctccatacc tctctgtggg aagagagtca ttcaccaatt cttctgtgat     600
gttcctcaga tgctgaaact agcctgttct tatgaattca ttaatgagat tgcactggct     660
gcattcacaa cgtctgcagc atttatctgt ttgatctcca ttgtgctctc ctacattcgc     720
atcttctcta cagtgctgag aatcccatca gctgagggcc ggaccaaggt cttctccacc     780
tgcctaccac acctatttgt agccaccttc tttctttcag ctgcaggctt tgagtttctc     840
agactgcctt ctgattcctc atcgactgtg gaccttgtat tctccgtatt ctatactgtg     900
ataccctcca cactcaatcc agtcatttat agcttacgga atgattccat gaaggcagca     960
ctgaggaaga tgctgtcaaa ggaagagctt cctcagagaa aaatgtgctt aaaagccatg    1020
tttaaactct ga                                                        1032

<210> SEQ ID NO 73
<211> LENGTH: 972
<212> TYPE: DNA
<213> ORGANISM: Homo sapiens
<220> FEATURE:
<221> NAME/KEY: misc_feature
<223> OTHER INFORMATION: Incyte ID No: 7472009CB1

<400> SEQUENCE: 73
atgtggcaga agaatcagac ctctctggca gacttcatcc ttgaggggct cttcgatgac      60
tcccttaccc accttttcct tttctccttg accatggtgg tcttcctta tgcggtgagt     120
ggcaacaccc tcaccattct cctcatctgc attgatcccc agcttcatac accaatgtat     180
ttcctgctca gccagctctc cctcatggat ctgatgcatg tctccacaac catcctgaag     240
atggctacca actacctatc tggcaagaaa tctatctcct tgtgggctg tgcaacccag      300
cacttcctct atttgtgtct aggtggtgct gaatgttttc tcttagctgt catgtcctat     360
gaccgctatg ttgccatctg tcatccactg cgctatgctg tgctcatgaa caagaaggtg     420
ggactgatga tggctgtcat gtcatggttg ggggcatccg tgaactccct aattcacatg     480
gcgatcttga tgcacttccc tttctgtggg cctcggaaag tctaccactt ctactgtgag     540
ttcccagctg ttgtgaagtt ggtatgtggc acatcactg tgtatgagac cacagtgtac     600
atcagcagca ttctcctcct cctccccatc ttcctgattt ctacatccta tgtcttcatc     660
cttcaaagtg tcattcagat gcgctcatct gggagcaaga gaaatgcctt gccacttgt      720
ggctcccacc tcacggtggt ttctctttgg tttggtgcct gcatcttctc ctacatgaga    780
cccaggtccc agtgcactct attgcagaac aaagttggtt ctgtgttcta cagcatcatt    840
```

```
acgcccacat tgaattctct gatttatact ctccggaata aagatgtagc taaggctctg      900
agaagagtgc tgaggagaga tgttatcacc cagtgcattc aacgactgca attgtggttg      960
ccccgagtgt ag                                                          972

<210> SEQ ID NO 74
<211> LENGTH: 900
<212> TYPE: DNA
<213> ORGANISM: Homo sapiens
<220> FEATURE:
<221> NAME/KEY: misc_feature
<223> OTHER INFORMATION: Incyte ID No: 7472010CB1

<400> SEQUENCE: 74
atggaactgg aaggagactt ccttggtagt gtgggagaat tgggccaagt gatccagacc       60
tgttctggga tctatgtgtt cactgtggtg ggcaacttgg gcttgatcac cttaattggg      120
ataaatccta gccttcacac ccccatgtac tttttcctct tcaacttgtc ctttatagat      180
ctctgttatt cctgtgtgtt tacccccaaa atgctgaatg actttgtttc agaaagtatc      240
atctcttatg tgggatgtat gactcagcta ttttttcttct gtttctttgt caattctgag      300
tgctatgtgt tggtatcaat ggcctatgat cgctatgtgg ccatctgcaa cccctgctc      360 tacatggtca ccatgtcccc aagggtctgc tttctgctga tgtttggttc ctatgtggta      420
gggtttgctg ggccatggc ccacactgga agcatgctgc gactgacctt ctgtgattcc      480
aacgtcattg accattatct gtgtgacgtt ctcccctct gcagctctc ctgcaccagc      540 acccatgtca gtgagctggt atttttcatt gttgttggag taatcaccat gctatccagc      600
ataagcatcg tcatctctta cgctttgata ctctccaaca tcctctgtat tccttctgca      660
gagggcagat ccaaagcctt tagcacatgg ggctcccaca taattgctgt tgctctgttt      720
tttgggtcag ggacattcac ctacttaaca acatctttc ctggctctat gaaccatggc      780
agatttgcct cagtctttta caccaatgtg gttcccatgc ttaacccttc gatctacagt      840
ttgaggaata aggatgataa acttgccctg ggcaaaaccc tgaagagagt gctcttctaa      900

<210> SEQ ID NO 75
<211> LENGTH: 924
<212> TYPE: DNA
<213> ORGANISM: Homo sapiens
<220> FEATURE:
<221> NAME/KEY: misc_feature
<223> OTHER INFORMATION: Incyte ID No: 7472011CB1

<400> SEQUENCE: 75
atggaaacag ggaacctcac gtgggtatca gactttgtct tcctggggct ctcgcagact       60
cgggagctcc agcgtttcct gtttctaatg ttcctgtttg tctacatcac cactgttatg      120
ggaaacatcc ttatcatcat cacagtgacc tctgattccc agctccacac acccatgtac      180
tttctgctcc gaaacctggc tgtcctagac ctctgtttct cttcagtcac tgctcccaaa      240
atgctagtgg acctcctctc tgagaagaaa accatctctt accagggctg catgggtcag      300
atcttcttct tccactttt gggaggtgcc atggtcttct tcctctcagt gatggccttt      360
gaccgcctca ttgccatctc ccggccccctc cgctatgtca ccgtcatgaa cactcagctc      420
tgggtggggc tggtggtagc cacctgggtg ggaggctttg tccactctat tgtccagctg      480
gctctgatgc tccccactgcc cttcgtggcc ccaacatttt ggataacttc tactgtgat      540 gttccccaag tactgagact tgcctgcact gacacctcac tgctggagtt cctcaagatc      600
```

```
tccaacagtg ggctgctgga tgtcgtctgg ttcttcctcc tcctgatgtc ctacttattc    660
atcctggtga tgctgaggtc acatccaggg gaggcaagaa ggaaggcagc ttccacctgc    720
accacccaca tcatcgtggt ttccatgatc ttcgttccaa gcatttacct ctatgcccgg    780
cccttcactc cattccctat ggacaagctt gtgtccatcg ccacacagt catgaccccc     840 atgctcaacc ccatgatcta taccctgagg aaccaggaca tgcaggcagc agtgagaaga    900
ttagggagac accggctggt ttga                                           924

<210> SEQ ID NO 76
<211> LENGTH: 945
<212> TYPE: DNA
<213> ORGANISM: Homo sapiens
<220> FEATURE:
<221> NAME/KEY: misc_feature
<223> OTHER INFORMATION: Incyte ID No: 7472012CB1

<400> SEQUENCE: 76
atggacaaca gcaactggac cagtgtgtcc catttgtgttc tcttgggcat ttccacccac    60
ccagaagagc aaatcccact cttccttgtt ttctcactca tgtacgcaat caatatttct    120
ggcaacttgg ccatcatcac actgattctc tctgctccac gcctccacat ccccatgtac    180
atcttcctca gtaacttggc cttgacagac atctgcttca cctccaccac ggtcccccaag   240 atgctgcaga ttattttctc ccctacaaag gtaatttcct acacaggctg tttagcccaa    300
acttatttct tcatttgctt cgccgtcatg gaaaacttca tcctggctgt gatggcctat    360
gacaggtaca ttgccatctg ccacccttc cactacacta tgatcctgac tagaatgctg     420
tgtgtgaaga tggtggtcat gtgccatgct ctctcccacc ttcatgccat gctgcatacc    480
tttctcatag ccaactaat cttctgtgca gataacagaa tcccccactt cttctgtgac     540
ctctacgctc tgatgaagat ctcctgcacc agcacctacc tcaacaccct tatgattcac    600
acagaaggtg ctgttgtaat cagtggagct ctggccttca ttactgcctc ctatgcctgc    660
atcatcctgg tggtcctccg gatcccctca gccaagggca ggtggaaaac cttttctacc    720
tgcggctccc acctcactgt ggtggccata ttctatggca ccctcagttg ggtctacttc    780
cggccccttt ccagctattc agtgaccaag ggtcgcatta taacagtcgt gtacacagtg    840
gtgactccca tgctgaaccc cttcatctac agcctgagga tgggggatgt caagggaggc    900
ttcatgaaat ggatgagcag aatgcagact tttttcttta gataa                    945

<210> SEQ ID NO 77
<211> LENGTH: 933
<212> TYPE: DNA
<213> ORGANISM: Homo sapiens
<220> FEATURE:
<221> NAME/KEY: misc_feature
<223> OTHER INFORMATION: Incyte ID No: 7472014CB1

<400> SEQUENCE: 77
atgggaagaa ataacctaac aagaccctct gaattcatcc tccttggact ctcctctcga    60
cctgaggatc agaagccgct ctttgctgtg ttcctcccca tctacctat cacagtgata    120 ggaaacctgc ttatcatcct ggccatccgc tcagacactc gtctccagac gcccatgtac    180
ttctttctaa gcatcctgtc ttttgttgac atttgctatg tgacagtcat tatccctaag    240
atgctggtga acttcttatc agagacaaag accatctctt acggtgagtg tctgacccag    300
atgtactttt tcttagcctt tggaaacaca gacagttacc tgctagcagc catggccatt    360
gaccgctatg tggccatatg taatcccttc cactacatca ccattatgag tcacagatgc    420
```

```
tgtgtcctgc ttctggttct ctccttctgc attccacatt ttcactccct cctgcacatt    480
cttctgacta atcagctcat cttctgtgcc tccaatgtca tccatcactt tttctgcgat    540
gatcaaccag tgctaaaatt gtcctgttcc tcccattttg tcaaagaaat cacagtaatg    600
acagaaggct tggctgtcat aatgacccg ttttcatgca tcatcatctc ttatttaaga     660
atcctcatca ctgttctgaa gattccttca gctgctggaa agcgtaaagc attttctacc    720
tgtggctctc atctcacagt ggtgaccctg ttttatggaa gcattagcta tgtctatttt    780
cagcccctgt ccaactatac tgtcaaggat caaatagcaa caattatcta caccgtactg    840
actcctatgc taaatccatt tatctatagt ctgaggaaca aagacatgaa gcagggtttg    900
gcaaagttga tgcacaggat gaaatgtcag taa                                 933

<210> SEQ ID NO 78
<211> LENGTH: 1080
<212> TYPE: DNA
<213> ORGANISM: Homo sapiens
<220> FEATURE:
<221> NAME/KEY: misc_feature
<223> OTHER INFORMATION: Incyte ID No: 7472020CB1

<400> SEQUENCE: 78
atgttcaaag ccatccttgg ccatgtgtgg cccaaagacc atgggttgga caagcttgtt     60
gtaaggtgtc caagacacac agagccatgg aatctcacag gtatctcaga attcctcctc    120
ctgggactct cagaggatcc agaactgcag cccgtcctcc ctgggctgtc cctgtccatg    180
tacctggtca cggtgctgag gaacctgctc atcatcctgg ctgtcagctc tgactcccac    240
ctccacaccc ccatgtgctt cttcctctcc aacctgtgct gggctgacat cggtttcacc    300
tcggccatgg ttcccaagat gattgtggac atgcagtcgc atagcagagt catctcttat    360
gcgggctgcc tgacacagat gtctttcttt gtccttttg catgtataga agacatgctc    420
ctgacagtga tggcctatga ccgatttgtg gccatctgtc acccctgca ctacccagtc    480 atcatgaatc ctcaccttgg tgtcttctta gttttggtgt cctttttcct cagcctgttg    540
gattcccagc tgcacagttg gattgtgtta caattcacct tcttcaagaa tgtggaaatc    600
tccaattttg tctgtgaccc atctcaactt ctcaaccttg cctgttctga cagtgtcatc    660
aatagcatat tcatatattt agatagtatt atgtttggtt tcttcccat ttcagggatc     720 cttttgtctt acgctaacaa tgtccctcc attctaagaa tttcatcatc agatagggag    780
tctaaagcct tctccacctg tggctctcac ctggcagttg tttgcttatt ttatggaaca    840
ggcattggcg tgtacctgac ttcagctgtg tcaccacccc ccaggaatgg tgtggtggca    900
tcagtgatgt acgctgtggt caccccatg ctgaaccctt tcatctacag cctgagaaat     960
agggacattc aaagtgccct gtggaggctg cgcagcagaa cagtcgaatc tcatgatctg   1020
ttatctcaag atctgctcca tccttttct tgtgtgggtg agaaaggtca accacattaa    1080
```